US012606853B2

(12) United States Patent　　　(10) Patent No.: US 12,606,853 B2

El Tahchy et al.　　　(45) Date of Patent: Apr. 21, 2026

(54) PRODUCTION OF SHORT CHAIN FATTY ACIDS

(71) Applicant: Nourish Ingredients PTY LTD, Mitchell (AU)

(72) Inventors: Anna El Tahchy, Moncrieff (AU); Dawar Hussain, Franklin (AU); Surinder Pal Singh, Downer (AU); Pushkar Shrestha, Lawson (AU); Rosangela Aparecida Devilla, Casey (AU); James Robertson Petrie, Goulburn (AU)

(73) Assignee: Nourish Ingredients PTY LTD, Mitchell (AU)

( * ) Notice: Subject to any disclaimer, the term of this patent is extended or adjusted under 35 U.S.C. 154(b) by 572 days.

(21) Appl. No.: 17/911,357

(22) PCT Filed: Mar. 12, 2021

(86) PCT No.: PCT/AU2021/050220

§ 371 (c)(1),
(2) Date: Sep. 13, 2022

(87) PCT Pub. No.: WO2021/179051

PCT Pub. Date: Sep. 16, 2021

(65) Prior Publication Data

US 2023/0127275 A1　　Apr. 27, 2023

(30) Foreign Application Priority Data

Mar. 13, 2020　(AU) ................................ 2020900780

(51) Int. Cl.
| | |
|---|---|
| *C12P 7/6463* | (2022.01) |
| *C11B 1/10* | (2006.01) |
| *C12N 9/10* | (2006.01) |
| *C12N 15/52* | (2006.01) |
| *C12N 15/81* | (2006.01) |

(52) U.S. Cl.
CPC ............ *C12P 7/6463* (2013.01); *C11B 1/106* (2013.01); *C12N 9/1029* (2013.01); *C12N 15/52* (2013.01); *C12N 15/81* (2013.01); *C12Y 203/0102* (2013.01); *C12N 2500/30* (2013.01)

(58) Field of Classification Search
CPC .. C12N 15/52; C12N 15/81; C12Y 203/0102; C12P 7/6464
See application file for complete search history.

(56) References Cited

U.S. PATENT DOCUMENTS

| | | | |
|---|---|---|---|
| 2013/0116462 A1 | 5/2013 | Durrett et al. | |
| 2018/0216144 A1 | 8/2018 | Rakitsky | |
| 2023/0127275 A1* | 4/2023 | El Tahchy | C12N 9/1029 435/159 |

FOREIGN PATENT DOCUMENTS

| | | |
|---|---|---|
| JP | 2018-531043 | 10/2018 |
| WO | WO2017058802 | 4/2017 |
| WO | WO2021050759 | 3/2021 |

OTHER PUBLICATIONS

Bansal et al., (2016) "Defining the extreme substrate specificity of Euonymus alatus diacylglycerol acetyltransferase, an unusual membrane-bound O-acyltransferase." Biosci. Rep., vol. 36, No. 6, e00406, 9 pages.

Durrett et al., (2010) "A distinct DGAT with sn-3 acetyltransferase activity that synthesizes unusual, reduced-viscosity oils in Euonymus and transgenic seeds." Proc. Natl. Acad. Sci., vol. 107, No. 20, pp. 9464-9469.

Ferreira Raphael et a., "Metabolic Engineering of *Saccharomyces cerevisiae* for Overproduction of Triacylglycerols", Metabolic Engineering Communications, vol. 6 Jun. 1, 2018 (Jun. 1, 2018), pp. 22-27.

Kim Young Hwan et al., "Identification of Triacylglycerols Containing Two Short-Chain Fatty Acids at SN-2 and SN-3 Positions from Bovine Udder by Fast Atom Bombardment Tandem Mass Spectrometry", Rapid Commun. Mass Spectrom., vol. 14, Jan. 1, 2000 (Jan. 1, 2000), pp. 2230-2237.

Leber Christopher et al., "Engineering of *Saccharomyces cerevisiae* for the Synthesis of Short Chain Fatty Acids", Biotechnology and Bioengineering, vol. 111, No. 2, Sep. 3, 2013 (Sep. 3, 2013) pp. 347-358.

Marshall M.O. et al., "Biosynthesis of Triacylglycerols containing short-chain fatty acids in lactating cow mammary gland", European Journal of Biochemistry, vol. 81, No. 2, Dec. 1, 1977 (Dec. 1, 1977), pp. 259-266.

Marshall M.O. et al., "Specificity of Diacylglycerol Acyltransferase from Bovine Mammary Gland, Liver and Adipose Tissue Towards Acyl-CoA esters", European Journal of Bioechmistry, Published by Springer-Verlag on Behalf of The Federation of European Biochemical Societies, Hoboken, USA, vol. 94, No. 1, Feb. 15, 1979 (Feb. 15, 1979), pp. 93-98.

Mitchell Tai et al., "Engineering the Push and Pull of Lipid Biosynthesis in Oleaginous Yeast Yarrowia Lipolytica for Biofuel Production", Metabolic Engineering, vol. 15, Jan. 1, 2013 (Jan. 1, 2013), pp. 1-9.

* cited by examiner

*Primary Examiner* — Tekchand Saidha

(74) *Attorney, Agent, or Firm* — Rudy J. Ng; Bozicevic, Field & Francis LLP

(57) ABSTRACT

The present invention relates to microbial cells comprising triacylglycerol (TAG) with short chain fatty acids (SCFA), as well as methods of using these cells to produce lipid comprising TAG with SCFAs.

9 Claims, 1 Drawing Sheet

Specification includes a Sequence Listing.

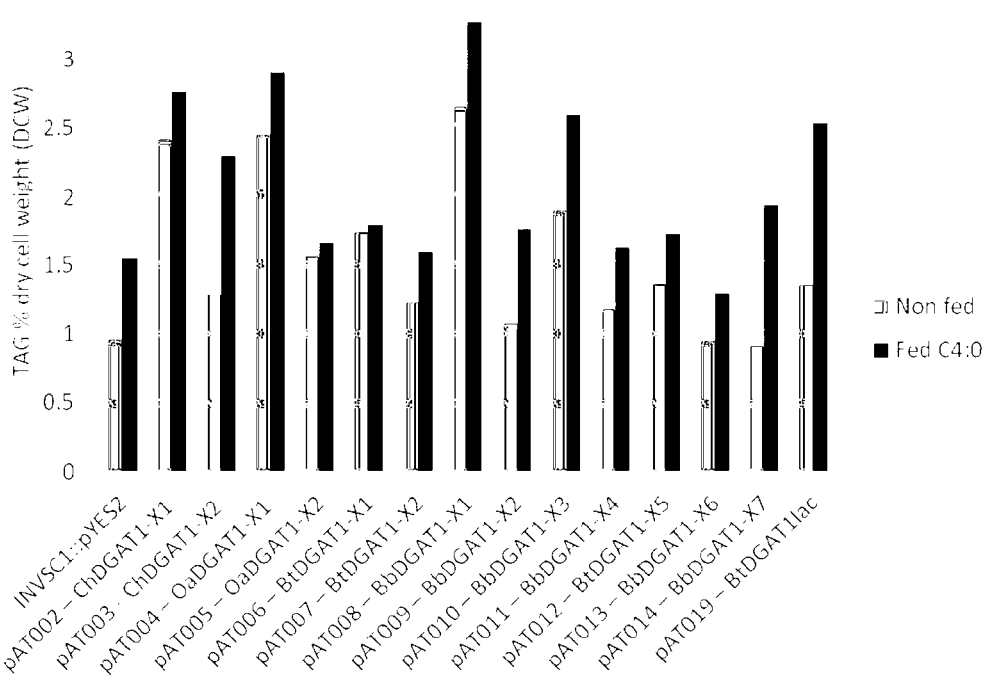

PRODUCTION OF SHORT CHAIN FATTY ACIDS

FIELD OF THE INVENTION

The present invention relates to microbial cells comprising triacylglycerol (TAG) with short chain fatty acids (SCFA), as well as methods of using these cells to produce lipid comprising TAG with SCFAs.

BACKGROUND OF THE INVENTION

As the global population surges towards a predicted 9.1 billion people by 2050, the demand for meat and dairy products for human nutrition is expected to continue to increase. However, meat and dairy production worldwide account for 70% of freshwater consumption, 38% of the total arable land use and contribute 19% of the world's greenhouse gas emissions. There is growing interest in finding alternative sources of protein and fat which have less of an environmental footprint. There is also a growing market worldwide for non-animal sources of high-quality protein and fat, for example from plant sources, which are seen as being more sustainable and environmentally friendly. Cultural and religious reasons have also contributed to growing markets for non-animal proteins. Sales of so-called plant milk, promoted as an alternative to dairy products, are predicted to surpass $34 billion globally by 2024. However, many current plant-based alternatives for meat and dairy products use fats made from blends of plant oils such as coconut, soy and palm oils which may give inadequate flavour and function. Fats and oils add flavour, lubricity and texture to foods and contribute to the feeling of satiety upon consumption, and therefore food and beverage products incorporating lipids from animal sources are often still preferred by consumers.

Bovine milk contains approximately 87% water, 4.6% lactose, 3.4% protein, 3.5-4.5% fat, 0.8% minerals and 0.1% vitamins (Mansson, 2008). The lipids in bovine milk are mainly present in globules as an oil-in-water emulsion. The fat component consists of approximately 97-98% triacylglycerols (TAG), about 2% diacylglycerol (DAG), 0.5% cholesterol, 0.1% phospholipids (PL) and free fatty acids (FFA), although the composition of milk and its fat varies with the breed of cattle, type of feed, lactation stage and season. Milk fat is unusual in its fatty acid composition and functional properties, comprising as many as 400 different fatty acids, making it the most complex of all natural fats. Saturated fatty acids make up about 70% by weight of the fatty acid content of the TAG, including palmitic acid (C16:0) at about 30% or more by weight of the total fatty acids. Myristate (C14:0) and stearate (C18:0) are each present at more than 10% of the total fatty acid content, and short chain fatty acids (SCFA; C2:0, C4:0, C6:0 and C8:0) are together present at about 6-8% of the total fatty acid content. Monounsaturated fatty acids, primarily oleic acid (C18:1Δ9) at up to about 22% but also including low levels of C14:1 and C16:1 make up most of the non-saturated fatty acid content. Milkfat generally contains only low levels (<2%) of polyunsaturated fatty acids (PUFA), present as linoleic acid (C18:2) and linolenic acid (C18:3). The short chain fatty acids butyric acid (C4:0) and caproic acid (C6:0) present in milkfat are esterified almost exclusively at the sn-3 position of TAG molecules.

There remains a need for alternative, non-animal sources of lipids that have animal-fat like composition and functional properties, for human nutrition.

SUMMARY OF THE INVENTION

The present inventors have produced microbial cells that comprise triacylglycerols (TAG), the TAG comprising short chain fatty acids (SCFA) esterified at the sn-1/3 position of TAG.

Thus, in one aspect the present invention provides a process for producing extracted lipid, comprising extracting lipid from microbial cells which comprise triacylglycerol (TAG) molecules, each TAG molecule having a fatty acid esterified at each of an sn-1 position, an sn-2 position and an sn-3 position, wherein at least some of the TAG molecules comprise a SCFA esterified at the sn-3 position, so as to thereby produce the extracted lipid. It is understood in this context that the sn-1, sn-2 and sn-3 positions refer to the sn-1, sn-2 and sn-3 positions of the glycerol component of the TAG molecule.

In an embodiment, the process comprises the steps of (a) obtaining microbial cells which comprise the TAG molecules, each TAG molecule having a fatty acid esterified at each of an sn-1 position, an sn-2 position and an sn-3 position, wherein at least some of the TAG molecules comprise a SCFA esterified at the sn-3 position, and (b) extracting lipid from the microbial cells, so as to thereby produce the extracted lipid.

In an embodiment, the esterified SCFA in the TAG molecules are one or more or all of butyric acid (C4:0), caproic acid (C6:0) and caprylic acid (C8:0).

In embodiments, the esterified SCFA in the TAG molecules comprise C4:0, or C4:0 and C6:0, preferably C4:0, C6:0 and C8:0. In a more preferred embodiment, the amount of C4:0 in the total fatty acid content of the TAG in the extracted lipid is greater than the amount of C6:0 or greater than the amount of C8:0, or both, most preferably greater than the sum of the amounts of C6:0 and C8:0, each amount being expressed as a percentage of the total fatty acid content of the TAG in the extracted lipid on a weight basis. It is understood that the same features may apply on a mol % basis.

In further embodiments (a), the extracted lipid comprises TAG molecules which comprise a SCFA esterified at their sn-2 position, wherein the ratio of the number of TAG molecules which comprise a SCFA esterified at the sn-2 position to the number of TAG molecules which comprise a SCFA esterified at their sn-3 position (SCFA ratio sn-2:sn-3) in the extracted lipid is less than about 0.50, less than about 0.30, less than about 0.20, less than about 0.10, less than about 0.05, less than about 0.04, less than about 0.03 or less than about 0.02. In preferred embodiments (b), the extracted lipid comprises TAG molecules which comprise C4:0 esterified at their sn-2 position, wherein the ratio of the number of TAG molecules which comprise C4:0 esterified at the sn-2 position to the number of TAG molecules which comprise C4:0 esterified at their sn-3 position (C4:0 ratio sn-2:sn-3) in the extracted lipid is less than about 0.50, less than about 0.30, less than about 0.20, less than about 0.10, less than about 0.05, less than about 0.04, less than about 0.03 or less than about 0.02. In further embodiments (c), the extracted lipid comprises TAG molecules which comprise C6:0 esterified at their sn-2 position, wherein the ratio of the number of TAG molecules which comprise C6:0 esterified at the sn-2 position to the number of TAG molecules which comprise C6:0 esterified at their sn-3 position (C6:0 ratio sn-2:sn-3) in the extracted lipid is less than about 0.50, less than about 0.30, less than about 0.20, less than about 0.10, less than about 0.05, less than about 0.04, less than about 0.03 or less than about 0.02. In further embodiments, both (a) and (b) apply, or (a) and (c) apply, or (b) and (c) apply.

In embodiments (a), the SCFA ratio sn-2:sn-3 is more than about 0.005, more than about 0.01, between about 0.005 and about 0.10, between about 0.01 and about 0.10, between about 0.005 and about 0.05 or between about 0.01 and about 0.05. In preferred embodiments (b), the C4:0 ratio sn-2:sn-3 is more than about 0.005, more than about 0.01, between about 0.005 and about 0.10, between about 0.01 and about 0.10, between about 0.005 and about 0.05 or between about 0.01 and about 0.05. In preferred embodiments (c), the C6:0 ratio sn-2:sn-3 is more than about 0.005, more than about 0.01, between about 0.005 and about 0.10, between about 0.01 and about 0.10, between about 0.005 and about 0.05 or between about 0.01 and about 0.05. In further embodiments, both (a) and (b) apply, or (a) and (c) apply, or (b) and (c) apply.

In embodiments, the SCFA comprises C4:0 and the sn-2: sn-3 ratio for C4:0 is more than about 0.01 or more than about 0.02.

In an embodiment, more of the TAG molecules in the extracted lipid have only one SCFA esterified in the TAG molecule than two SCFA esterified in the TAG molecule. In an embodiment, more of the TAG molecules in the extracted lipid have only one C4:0 esterified in the TAG molecule than two C4:0 fatty acids esterified in the TAG molecule. In an embodiment, more of the TAG molecules in the extracted lipid have only one C6:0 esterified in the TAG molecule than two C6:0 fatty acids esterified in the TAG molecule.

In embodiments, at least 1% by weight or by mol %, or both, of the total fatty acid content of the extracted lipid is SCFA, preferably at least 1% C4:0, or at least 1% for the sum of C4:0 and C6:0.

In embodiments, at least 10%, at least 15%, at least 20%, at least 25% or at least 30% by weight of the total fatty acid content of the extracted lipid is C16:1, preferably to a maximum of 50%.

In embodiments, the TAG molecules of the extracted lipid comprise more C16:1 esterified at the sn-2 position than any other fatty acid esterified at the sn-2 position, preferably wherein at least 30% or at least 40% of the fatty acids esterified at the sn-2 position of the TAG molecules are C16:1.

In embodiments, the microbial cells comprise fungal cells, bacterial cells or algal cells, or any mixture thereof, preferably yeast cells, more preferably *Saccharomyces cerevisiae* cells. In an embodiment, the microbial cells are one or more or all of (i) suitable for fermentation, (ii) oleaginous cells, and (iii) heterotrophic cells.

In an embodiment, the fungal cells comprise yeast cells. Examples include, but are not limited to *Saccharomyces cerevisiae, Yarrowia lipolytica, Trichoderma* spp., *Pichia pastoris, Candida rugose, Aspergillus niger, Cryptheco-dinium cohnii* and any mixture thereof.

In an embodiment, the microbial cells comprise algal cells selected from the group consisting of *Prototheca morifor-mis, Thraustochytrium* spp., *Chlorella protothecoides, Schizochytrium* sp. such as strain FCC-1324, and any mixture thereof. In an embodiment, the microbial cells are *Mortierella alpina*.

In an embodiment, the cells comprise one or more exogenous polynucleotide(s) encoding a fatty acid acyltransferase or more than one fatty acid acyltransferase, wherein at least one acyltransferase has activity on SCFA-CoA molecules as a substrate, preferably at least butyryl-CoA as a substrate or at least butyryl-CoA and caproyl-CoA as substrates, and wherein each exogenous polynucleotide is operably linked to one or more promoters that are capable of directing expression of said polynucleotide in the cells.

In an embodiment, the exogenous polynucleotide is integrated into the genome of the cell, preferably the nuclear genome of the cell. In an embodiment, the cell comprises exogenous polynucleotides which are integrated into the nuclear genome of the cell, which are either integrated at a single site in the genome or at least one exogenous polynucleotide is integrated at one site and at least one other exogenous polynucleotide is integrated at a second site. More than 2 integration sites are also contemplated. Alternatively, the exogenous polynucleotide(s) is comprised in an autonomously replicating vector in the cell.

In an embodiment, at least one of the fatty acid acyltransferases is a mammalian acyltransferase or a variant thereof, preferably a ruminant acyltransferase or a variant thereof.

In an embodiment, at least one of the acyltransferases is a diacylglycerol O-acyltransferase (DGAT), preferably a 1,2-diacyl-sn-glycerol:acetyl-CoA acetyltransferase (DAcT) or a DGAT1. In an embodiment, the DGAT is a mammalian DGAT or a variant thereof, preferably a ruminant DGAT or a variant thereof.

In embodiments, the DGAT comprises amino acids whose sequence is set forth as any one of SEQ ID NOs:1, 3, 5, 7, 9, 11, 13, 15, 17, 19, 21, 23, 25, 27 or 29, or an amino acid sequence which is at least 30% identical along the full length of any one or more of SEQ ID NOs:1, 3, 5, 7, 9, 11, 13, 15, 17, 19, 21, 23, 25, 27 or 29.

In embodiments, the exogenous polynucleotide encoding the DGAT comprises nucleotides whose sequence is set forth as any one of SEQ ID NOs:2, 4, 6, 8, 10, 12, 14, 16, 18, 20, 22, 24, 26, 28 or 30, or a nucleotide sequence which is at least 30% identical along the full length of any one or more of SEQ ID NOs: 2, 4, 6, 8, 10, 12, 14, 16, 18, 20, 22, 24, 26, 28 or 30.

The lipid can be extracted by any means known in the art such as, but not limited to, exposing the cells to an organic solvent, pressing the cells or treating the cells with microwave irradiation, ultrasonication, high-speed homogenization, high-pressure homogenization, bead beating, autoclaving, thermolysis or any combination thereof.

In an embodiment, the method further comprises culturing the cells, preferably yeast cells, more preferably *Saccharomyces cerevisiae* cells.

In an embodiment, the cells are cultured in a medium comprising butyrate (C4:0), preferably at a concentration in the range of about 1 to about 20 g/L in the medium.

In an embodiment, the method further comprises modifying or purifying the lipid, for example by degumming, deodorizing or distilling or fractionating the lipid. In a preferred embodiment, the lipid has not been treated by transesterification. In an embodiment (a), the amount of SCFA, preferably C4:0, expressed as a percentage of the total fatty acid content of the extracted lipid, has not been changed by more than 10% on a relative basis after the extraction from the microbial cells. For example, if the amount of SCFA in the initially extracted lipid was 8% on a weight basis, the modified or purified lipid has between 7.2% and 8.8% SCFA. In an embodiment (b), the SCFA sn-2:sn-3 ration has not been changed by more than 10% by the modifying or purifying process. Both (a) and (b) may apply.

In another aspect, the present invention provides extracted microbial lipid produced by the process of the invention or produced from the cells of the invention, preferably extracted yeast lipid, more preferably extracted *Saccharomyces cerevisiae* lipid. In an embodiment, the extracted microbial lipid comprises triacylglycerol (TAG) molecules, each TAG molecule having a fatty acid esterified at each of an sn-1 position, an sn-2 position and an sn-3 position, wherein at least some of the TAG molecules comprise a short chain fatty acid (SCFA) esterified at the sn-3 position of the TAG molecule.

The cells or lipid may comprise any feature outlined for the above process aspect, singly or in every possible combination.

In an embodiment, the SCFAs esterified at the sn-3 position of the TAG molecules are one or more or all of C4:0, C6:0 and C8:0.

In an embodiment, the SCFAs esterified at the sn-3 position of the TAG molecules comprise C4:0, or C4:0 and C6:0, preferably C4:0, C6:0 and C8:0. In a preferred embodiment, the amount of C4:0 in the total fatty acid content of the TAG in the extracted lipid is greater than the amount of C6:0 or greater than the amount of C8:0, or both, more preferably greater than the sum of the amounts of C6:0 and C8:0, each amount being expressed as a percentage of the total fatty acid content of the TAG in the extracted lipid on a weight basis. It is understood that the same features may apply on a mol % basis.

In embodiments (a), the extracted lipid comprises TAG molecules which comprise a SCFA esterified at their sn-2 position, wherein the ratio of the number of TAG molecules which comprise a SCFA esterified at the sn-2 position to the number of TAG molecules which comprise a SCFA esterified at their sn-3 position (SCFA ratio sn-2:sn-3) in the extracted lipid is less than about 0.50, less than about 0.30, less than about 0.20, less than about 0.10, less than about 0.05, less than about 0.04, less than about 0.03 or less than about 0.02. In preferred embodiments (b), the extracted lipid comprises TAG molecules which comprise C4:0 esterified at their sn-2 position, wherein the ratio of the number of TAG molecules which comprise C4:0 esterified at the sn-2 position to the number of TAG molecules which comprise C4:0 esterified at their sn-3 position (C4:0 ratio sn-2:sn-3) in the extracted lipid is less than about 0.50, less than about 0.30, less than about 0.20, less than about 0.10, less than about 0.05, less than about 0.04, less than about 0.03 or less than about 0.02. In further embodiments (c), the extracted lipid comprises TAG molecules which comprise C6:0 esterified at their sn-2 position, wherein the ratio of the number of TAG molecules which comprise C6:0 esterified at the sn-2 position to the number of TAG molecules which comprise C6:0 esterified at their sn-3 position (C6:0 ratio sn-2:sn-3) in the extracted lipid is less than about 0.50, less than about 0.30, less than about 0.20, less than about 0.10, less than about 0.05, less than about 0.04, less than about 0.03 or less than about 0.02. In further embodiments, both (a) and (b) apply, or (a) and (c) apply, or (b) and (c) apply.

In embodiments (a), the SCFA ratio sn-2:sn-3 of the extracted lipid is more than about 0.005, more than about 0.01, between about 0.005 and about 0.10, between about 0.01 and about 0.10, between about 0.005 and about 0.05 or between about 0.01 and about 0.05. In preferred embodiments (b), the C4:0 ratio sn-2:sn-3 is more than about 0.005, more than about 0.01, between about 0.005 and about 0.10, between about 0.01 and about 0.10, between about 0.005 and about 0.05 or between about 0.01 and about 0.05. In preferred embodiments (c), the C6:0 ratio sn-2:sn-3 is more than about 0.005, more than about 0.01, between about 0.005 and about 0.10, between about 0.01 and about 0.10, between about 0.005 and about 0.05 or between about 0.01 and about 0.05. In further embodiments, both (a) and (b) apply, or (a) and (c) apply, or (b) and (c) apply.

In an embodiment, the SCFA comprises C4:0 and the sn-2:sn-3 ratio for C4:0 is more than about 0.01 or more than about 0.02.

In an embodiment, more of the TAG molecules in the extracted lipid have only one SCFA esterified in the TAG molecule than two SCFA esterified in the TAG molecule. In an embodiment, more of the TAG molecules in the extracted lipid have only one C4:0 esterified in the TAG molecule than two C4:0 fatty acids esterified in the TAG molecule. In an embodiment, more of the TAG molecules in the extracted lipid have only one C6:0 esterified in the TAG molecule than two C6:0 fatty acids esterified in the TAG molecule.

In an embodiment (a), at least 1% by weight or by mol %, or both, of the total fatty acid content of the extracted lipid is SCFA, preferably at least 1% C4:0, or at least 1% for the sum of C4:0 and C6:0.

In embodiments (b), at least 10%, at least 15%, at least 20%, at least 25% or at least 30% by weight of the total fatty acid content of the extracted lipid is C16:1, preferably to a maximum of 50% or 45%.

In embodiments (c), the TAG molecules of the extracted lipid comprise more C16:1 esterified at the sn-2 position than any other fatty acid esterified at the sn-2 position, preferably wherein at least 30% or at least 40% of the fatty acids esterified at the sn-2 position of TAG are C16:1. The combinations (a) and (b), (a) and (c), (b) and (c), and all three of (a), (b) and (c) are contemplated.

In an embodiment, the amount of total saturated fatty acids in the extracted microbial lipid, expressed as a percentage of the total fatty acid content of the extracted lipid, is less than the amount in milk fat, preferably at least 10% or at least 20% less on a relative basis. In an embodiment, the amount of total saturated fatty acids in the extracted microbial lipid is between 30% and 50% or between 50% and 70%, on a weight basis. In an embodiment, the amount of C16:0 or C18:0, or the sum of both, in the extracted microbial lipid is less than the amount in milk fat preferably at least 10% or at least 20% less on a relative basis.

In an embodiment, the extracted lipid is a liquid at room temperature (25° C.) i.e. it is an oil. In an embodiment, the extracted lipid is a solid at room temperature (25° C.), i.e. it is a fat. The lipid may also be a mixture of liquid and solid at room temperature.

In a further aspect, the present invention provides a microbial cell, or microbial cells, preferably yeast cells, more preferably *Saccharomyces cerevisiae* cells, comprising triacylglycerol (TAG) molecules, each TAG molecule having a fatty acid esterified at each of an sn-1 position, an sn-2 position and an sn-3 position, wherein at least some of the TAG molecules comprise a short chain fatty acid (SCFA) esterified at the sn-3 position of the TAG molecule.

A microbial cell of the invention may comprise any feature outlined for the above process or extracted lipid aspects, singly or in any possible combination of features.

In a further aspect, the present invention provides a microbial cell, or microbial cells, preferably yeast cells, more preferably *Saccharomyces cerevisiae* cells, comprising one or more exogenous polynucleotide(s) encoding a fatty acid acyltransferase or more than one fatty acid acyltransferase, wherein at least one acyltransferase has activity on SCFA-CoA molecules as a substrate, preferably at least butyryl-CoA as a substrate or at least butyryl-CoA and caproyl-CoA as substrates, and wherein each exogenous polynucleotide is operably linked to one or more promoters that are capable of directing expression of said polynucleotide in the cells.

In embodiments (a), at least one of the fatty acid acyltransferases is a mammalian acyltransferase or a variant thereof, preferably a ruminant acyltransferase or a variant thereof, or at least one of the acyltransferases is a diacylglycerol O-acyltransferase (DGAT), preferably a 1,2-diacyl-sn-glycerol:acetyl-CoA acetyltransferase (DAcT) or a DGAT1, or the DGAT is a mammalian DGAT or a variant thereof, preferably a ruminant DGAT or a variant thereof.

In further embodiments (b), the DGAT comprises amino acids whose sequence is set forth as any one of SEQ ID NOs:1, 3, 5, 7, 9, 11, 13, 15, 17, 19, 21, 23, 25, 27 or 29, or an amino acid sequence which is at least 30% identical along the full length of any one or more of SEQ ID NOs:1, 3, 5, 7, 9, 11, 13, 15, 17, 19, 21, 23, 25, 27 or 29.

In further embodiments (c), the exogenous polynucleotide encoding the DGAT comprises nucleotides whose sequence is set forth as any one of SEQ ID NOs:2, 4, 6, 8, 10, 12, 14, 16, 18, 20, 22, 24, 26, 28 or 30, or a nucleotide sequence which is at least 30% identical along the full length of any one or more of SEQ ID NOs: 2, 4, 6, 8, 10, 12, 14, 16, 18, 20, 22, 24, 26, 28 or 30.

In an embodiment (d), the microbial cell(s) comprise TAG molecules, wherein at least some of the TAG molecules comprise a short chain fatty acid (SCFA) esterified at the sn-3 position of the TAG molecule. In further embodiments, both (a) and (b) apply, or (a) and (c) apply, or (a) and (d) apply, or (b) and (d) apply, or (c) and (d) apply.

In an embodiment, the microbial cell(s) comprise an increased amount of TAG relative to a corresponding microbial cell lacking the one or more exogenous polynucleotides, cultured under the same conditions. In a preferred embodiment, the increased amount is at least 1% on an absolute basis, e.g. from 1% to at least 2% on a weight basis, or at least 20% on a relative basis, for example increased between 20% and 200% or 250% i.e. between 1.2-fold and 3.0-fold or 3.5-fold increased. In preferred embodiments, this feature of increased TAG content is combined with any of the features (a), (b), (c) or (d) above or features described for a process of the invention or the extracted lipid of the invention.

A microbial cell of the invention may comprise any feature outlined for the above process or extracted lipid aspects, singly or in any possible combination of features.

In another aspect, the present invention provides a process for culturing microbial cells, preferably yeast cells, more preferably *Saccharomyces cerevisiae* cells, the process comprising (a) obtaining a microbial cell which produces TAG molecules, each TAG molecule having a fatty acid esterified at each of an sn-1 position, an sn-2 position and an sn-3 position, wherein at least some of the TAG molecules comprise a short chain fatty acid (SCFA) esterified at the sn-3 position of the TAG molecule, and/or
(b) obtaining a microbial cell which comprises one or more exogenous polynucleotide(s) encoding a fatty acid acyltransferase or more than one fatty acid acyltransferase, wherein at least one acyltransferase has activity on SCFA-CoA molecules as a substrate, preferably at least butyryl-CoA as a substrate or at least butyryl-CoA and caproyl-CoA as substrates, and wherein each exogenous polynucleotide is operably linked to one or more promoters that are capable of directing expression of said polynucleotide in the cells, and
(c) increasing the number of the cells by culturing the cells in a suitable medium.

In an embodiment, the medium comprises butyrate (C4: 0), preferably at a level of between 1 and 20 g/L at some time during the culturing, more preferably throughout most of the time of culturing.

In another aspect, the present invention provides a process for producing a microbial cell which produces TAG molecules, the process comprising a step of introducing one or more exogenous polynucleotides encoding one or more fatty acid acyltransferases as defined herein. The acyltransferases may be characterised by both (a) and (b) above, or (a) and (c), or (a) and (d), or (b) and (d), or (c) and (d) as applied to the microbial cells.

In an embodiment, the process comprises a step of one or more or all of (i) producing progeny cells from the cell comprising the introduced exogenous polynucleotides,
(ii) selecting a progeny cell which has one or more of the features of a cell or lipid defined herein.

In another aspect, the present invention provides a process for selecting or identifying a microbial cell of the invention, or which comprises one or more of the features defined herein, the process comprising steps of (i) analysing lipid from microbial cells comprising one or more exogenous polynucleotides as defined herein, and
(ii) selecting or identifying the microbial cell.

Also provided is a composition comprising one or more of the lipid of the invention or the microbial cell(s) of the invention.

In an embodiment, the composition comprises at least one other lipid from a source other than a cell of the invention. In an embodiment, the lipid from the other source does not comprise SCFA esterified in the form of TAG. In an embodiment, the ratio of the amounts of the extracted microbial lipid of the invention to the lipid from the other source is between 10:1 and 1:10.

In a further aspect, the present invention provides a food, feedstuff or beverage ingredient, or a food, feedstuff or beverage, comprising one or more of extracted lipid of the invention, the microbial cell(s) of the invention, or the composition of the invention, and least one other food, feedstuff or beverage ingredient. Preferably, the amount of the extracted lipid of the invention, the microbial cell(s) of the invention, or the composition of the invention in the food or feedstuff is at least 1% on a dry weight basis, preferably between 1% and 20%. Preferably, the amount of the extracted lipid of the invention, the microbial cell(s) of the invention, or the composition of the invention in the beverage is at least 0.5% on a weight basis, preferably between 0.5% and 5% on a weight basis.

In an embodiment, the food, feedstuff or beverage ingredient, or food, feedstuff or beverage has no components derived from an animal.

In another aspect, the present invention provides a method of producing a food, feedstuff or beverage ingredient, or food, feedstuff or beverage, the method comprising mixing one or more of extracted lipid of the invention, the microbial cell of the invention, or the composition of the invention, with at least one other food, feedstuff or beverage ingredient, and/or processing the extracted lipid of the invention, the microbial cell of the invention or the composition of the invention.

In another aspect, the present invention provides for the use of one or more of extracted lipid of the invention, the microbial cell of the invention, or the composition of the invention to produce a food, feedstuff or beverage ingredient, or food, feedstuff or beverage.

In another aspect, the present invention provides a process for producing extracted lipid, comprising (a) obtaining microbial cells which comprise triacylglycerol (TAG) molecules, each TAG molecule having a fatty acid esterified at each of an sn-1 position, an sn-2 position and an sn-3 position, wherein at least some of the TAG molecules comprise a SCFA esterified at the sn-3 position, and (b) extracting lipid from the microbial cells, so as to thereby produce the extracted lipid. It is understood in this context that the sn-1, sn-2 and sn-3 positions refer to the sn-1, sn-2 and sn-3 positions of the glycerol component of the TAG molecule.

In an embodiment, the esterified SCFA in the TAG molecules are one or more or all of butyric acid (C4:0), caproic acid (C6:0) and caprylic acid (C8:0).

In another embodiment, the esterified SCFA in the TAG molecules comprise C4:0, or C4:0 and C6:0.

In a further embodiment, the extracted lipid comprises TAG molecules which comprise a SCFA esterified at their sn-2 position, wherein the ratio of the number of TAG molecules which comprise a SCFA esterified at the sn-2 position to the number of TAG molecules which comprise a SCFA esterified at their sn-3 position (SCFA ratio sn-2:sn-3) in the extracted lipid is less than about 0.50, less than about 0.30, less than about 0.20, less than about 0.10, less than about 0.05, less than about 0.04, less than about 0.03 or less than about 0.02.

In an embodiment, the SCFA ratio sn-2:sn-3 is more than about 0.005, more than about 0.01, between about 0.005 and about 0.10, between about 0.01 and about 0.10, between about 0.005 and about 0.05 or between about 0.01 and about 0.05.

In an embodiment, the SCFA is C4:0 and the SCFA ratio sn-2:sn-3 is more than about 0.01 or more than about 0.02.

In an embodiment, more of the TAG molecules in the extracted lipid have only one SCFA esterified in the TAG molecule than two SCFA esterified in the TAG molecule.

In an embodiment, at least 1% by weight or by mol %, or both, of the total fatty acid content of the extracted lipid is SCFA, preferably C4:0, or C4:0 and C6:0.

In an embodiment, at least 10%, at least 15%, at least 20%, at least 25% or at least 30% by weight of the total fatty acid content of the extracted lipid is C16:1, preferably to a maximum of 50%.

In an embodiment, the TAG molecules of the extracted lipid comprise more C16:1 esterified at the sn-2 position than any other fatty acid esterified at the sn-2 position, preferably wherein at least 30% or at least 40% of the fatty acids esterified at the sn-2 position of the TAG molecules are C16:1.

In an embodiment, the TAG molecules of the extracted lipid comprise more C16:0 esterified at the sn-2 position than any other fatty acid esterified at the sn-2 position of the TAG molecules.

In an embodiment, the microbial cells comprise fungal cells, bacterial cells or algal cells, or any misture thereof In an embodiment, the microbial cells are one or more or all of (i) suitable for fermentation, (ii) oleaginous cells, and (iii) heterotrophic cells.

In an embodiment, the fungal cells comprise yeast cells. Examples include, but are not limited to Saccharomyces cerevisiae, Yarrowia lipolytica, Trichoderma spp., Pichia pastoris, Candida rugose, Aspergillus niger, Cryptheco-dinium cohnii and any mixture thereof.

In an embodiment, the microbial cells comprise algal cells selected from the group consisting of Prototheca moriformis, Thraustochytrium spp., Chlorella protothecoides, Schizochytrium sp. such as strain FCC-1324, and any mixture thereof. In an embodiment, the microbial cells are Mortierella alpina.

In an embodiment, the cells comprise one or more exogenous polynucleotide(s) encoding a fatty acid acyltransferase or more than one fatty acid acyltransferase, wherein at least one acyltransferase has activity on SCFA-CoA molecules as a substrate, preferably at least butyryl-CoA as a substrate or at least butyryl-CoA and caproyl-CoA as substrates, and wherein each exogenous polynucleotide is operably linked to one or more promoters that are capable of directing expression of said polynucleotide in the cells.

In an embodiment, the exogenous polynucleotide is intergrated into the genome of the cell.

In an embodiment, at least one of the fatty acid acyltransferases is a mammalian acyltransferase or a variant thereof, preferably a ruminant acyltransferase or a variant thereof.

In an embodiment, at least one of the acyltransferases is a diacylglycerol O-acyltransferase (DGAT).

In an embodiment, the DGAT is a 1,2-diacyl-sn-glycerol: acetyl-CoA acetyltransferase (DAcT).

In an embodiment, the DGAT is a DGAT1. In an embodiment, the DGAT is a mammalian DGAT or a variant thereof, preferably a ruminant DGAT or a variant thereof.

In an embodiment, the DGAT comprises amino acids whose sequence is set forth as any one of SEQ ID NOs:1, 3, 5, 7, 9, 11, 13, 15, 17, 19, 21, 23, 25, 27 or 29, or an amino acid sequence which is at least 30% identical along the full length of any one or more of SEQ ID NOs:1, 3, 5, 7, 9, 11, 13, 15, 17, 19, 21, 23, 25, 27 or 29.

In an embodiment, the exogenous polynucleotide encoding the DGAT comprises nucleotides whose sequence is set forth as any one of SEQ ID NOs:2, 4, 6, 8, 10, 12, 14, 16, 18, 20, 22, 24, 26, 28 or 30, or a nucleotide sequence which is at least 30% identical along the full length of any one or more of SEQ ID NOs: 2, 4, 6, 8, 10, 12, 14, 16, 18, 20, 22, 24, 26, 28 or 30.

The lipid can be extracted by any means known in the art such as, but not limited to, exposing the cells to an organic solvent, pressing the cells or treating the cells with microwave irradiation, ultrasonication, high-speed homogenization, high-pressure homogenization, bead beating, autoclaving, thermolysis or any combination thereof.

In an embodiment, the method further comprises culturing the cells.

In an embodiment, the cells are cultured in a medium comprising butyrate (C4:0), preferably at a concentration in the range of about 1 to about 20 g/L in the medium.

In an embodiment, the method further comprises modifying or purifying the lipid, for example by degumming, deodorizing or distilling or fractionating the lipid. In a preferred embodiment, the lipid has not been treated by transesterification.

In another aspect, the present invention provides extracted microbial lipid comprising triacylglycerol (TAG) molecules, each TAG molecule having a fatty acid esterified at each of an sn-1 position, an sn-2 position and an sn-3 position, wherein at least some of the TAG molecules comprise a short chain fatty acid (SCFA) esterified at the sn-3 position of the TAG molecule.

The cells or lipid may comprise any feature outlined for the above process aspect.

In an embodiment, the SCFAs esterified at the sn-3 position of the TAG molecules are one or more or all of C4:0, C6:0 and C8:0.

In an embodiment, the SCFAs esterified at the sn-3 position of the TAG molecules comprise C4:0, or C4:0 and C6:0.

In an embodiment, the extracted lipid comprises TAG molecules which comprise a SCFA esterified at their sn-2 position, wherein the ratio of the number of TAG molecules which comprise a SCFA esterified at the sn-2 position to the number of TAG molecules which comprise a SCFA esterified at their sn-3 position (SCFA ratio sn-2:sn-3) in the extracted lipid is less than about 0.50, less than about 0.30, less than about 0.20, less than about 0.10, less than about 0.05, less than about 0.04, less than about 0.03 or less than about 0.02.

In an embodiment, the SCFA ratio sn-2:sn-3 is more than about 0.005, more than about 0.01, between about 0.005 and about 0.10, between about 0.01 and about 0.10, between about 0.005 and about 0.05 or between about 0.01 and about 0.05.

In an embodiment, the SCFA is C4:0 and the SCFA ratio sn-2:sn-3 is more than about 0.01 or more than about 0.02.

In an embodiment, more of the TAG molecules in the extracted lipid have only one SCFA esterified in the TAG molecule than two SCFA esterified in the TAG molecule.

In an embodiment, at least 1% by weight or by mol %, or both, of the total fatty acid content of the extracted lipid is SCFA, preferably C4:0, or C4:0 and C6:0.

In an embodiment, at least 10%, at least 15%, at least 20%, at least 25% or at least 30% by weight of the total fatty acid content of the extracted lipid is C16:1, preferably to a maximum of 50% or 45%.

In an embodiment, the TAG molecules of the extracted lipid comprise more C16:1 esterified at the sn-2 position than any other fatty acid esterified at the sn-2 position, preferably wherein at least 30% or at least 40% of the fatty acids esterified at the sn-2 position of TAG are C16:1.

In an embodiment, the TAG molecules of the extracted lipid comprise more C16:0 esterified at the sn-2 position than any other fatty acid esterified at the sn-2 position.

In an embodiment, the extracted lipid is a liquid at room temperature (25° C.) i.e. it is an oil. In an embodiment, the extracted lipid is a solid at room temperature (25° C.), i.e. it is a fat. The lipid may also be a mixture of liquid and solid at room temperature.

In a further aspect, the present invention provides a microbial cell comprising triacylglycerol (TAG) molecules, each TAG molecule having a fatty acid esterified at each of an sn-1 position, an sn-2 position and an sn-3 position, wherein at least some of the TAG molecules comprise a short chain fatty acid (SCFA) esterified at the sn-3 position of the TAG molecule.

A microbial cell of the invention may comprise any feature outlined for the above process or extracted lipid aspects.

In another aspect, the present invention provides a process for culturing microbial cells, the process comprising (a) obtaining a microbial cell which produces TAG molecules, each TAG molecule having a fatty acid esterified at each of an sn-1 position, an sn-2 position and an sn-3 position, wherein at least some of the TAG molecules comprise a short chain fatty acid (SCFA) esterified at the sn-3 position of the TAG molecule, and

(b) increasing the number of the cells by culturing the cells in a suitable medium.

In an embodiment, the medium comprises butyrate (C4:0).

In another aspect, the present invention provides a process for producing a microbial cell which produces TAG molecules, the process comprising a step of introducing one or more exogenous polynucleotides as defined herein.

In an embodiment, the process comprises a step of one or more or all of (i) producing progeny cells from the cell comprising the introduced exogenous polynucleotides, (ii) selecting a progeny cell which has one or more of the features of a cell or lipid defined herein.

In another aspect, the present invention provides a process for selecting or identifying a microbial cell of the invention, or which comprises one or more of the features defined herein, the process comprising steps of (i) analysing lipid from microbial cells comprising one or more exogenous polynucleotides as defined herein, and (ii) selecting or identifying the microbial cell.

Also provided is a composition comprising one or more of the lipid of the invention or the microbial cell of the invention.

In an embodiment, the composition comprises at least one other lipid from a source other than a cell of the invention.

In a further aspect, the present invention provides a food or feedstuff comprising one or more of extracted lipid of the invention, the microbial cell of the invention, or the composition of the invention, and least one other food ingredient.

In an embodiment, the food or feedstuff has no components derived from an animal.

In another aspect, the present invention provides a method of producing a food or feedstuff, the method comprising mixing one or more of extracted lipid of the invention, the microbial cell of the invention, or the composition of the invention, with at least one other food ingredient.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Oil content of *S. cerevisiae* cells transformed with DGAT genes.

KEY TO THE SEQUENCE LISTING

SEQ ID NO:1—Amino acid sequence of *Euonymus alatus* 1,2-diacyl-sn-glycerol:acetyl-CoA acetyltransferase (EaDAcT).

SEQ ID NO:2—Nucleotide sequence of the protein coding region of *Euonymus alatus* 1,2-diacyl-sn-glycerol: acetyl-CoA acetyltransferase (EaDAcT) in pAT001, codon optimised for expression in yeast.

SEQ ID NO:3—Amino acid sequence of *Capra hircus* (goat) diacylglycerol O-acyltransferase 1 isoform X1 (ChDGAT1-X1).

SEQ ID NO:4—Nucleotide sequence of the protein coding region of *Capra hircus* (goat) diacylglycerol O-acyltransferase 1 isoform X1 (ChDGAT1-X1) in pAT002, codon optimised for expression in yeast.

SEQ ID NO:5—Amino acid sequence of *Capra hircus* (goat) diacylglycerol O-acyltransferase 1 isoform X2 (ChDGAT1-X2).

SEQ ID NO:6—Nucleotide sequence of the protein coding region of *Capra hircus* (goat) diacylglycerol O-acyltransferase 1 isoform X2 (ChDGAT1-X2) in pAT003, codon optimised for expression in yeast.

SEQ ID NO:7—Amino acid sequence of *Ovis aries* (sheep) diacylglycerol O-acyltransferase 1 isoform X1 (OaDGAT1-X1).

SEQ ID NO:8—Nucleotide sequence of the protein coding region of *Ovis aries* (sheep) diacylglycerol O-acyltransferase 1 isoform X1 (OaDGAT1-X1) in pAT004, codon optimised for expression in yeast.

SEQ ID NO:9—Amino acid sequence of *Ovis aries* (sheep) diacylglycerol O-acyltransferase 1 isoform X2 (OaDGAT1-X2).

SEQ ID NO:10—Nucleotide sequence of the protein coding region of *Ovis aries* (sheep) diacylglycerol O-acyltransferase 1 isoform X2 (OaDGAT1-X2) in pAT005, codon optimised for expression in yeast.

SEQ ID NO:11—Amino acid sequence of *Bos taurus* (cattle) diacylglycerol O-acyltransferase 1 isoform X1 (BtDGAT1-X1).

SEQ ID NO:12—Nucleotide sequence of the protein coding region of *Bos taurus* (cattle) diacylglycerol O-acyltransferase 1 isoform X1 (BtDGAT1-X1) in pAT006, codon optimised for expression in yeast.

SEQ ID NO:13—Amino acid sequence of *Bos taurus* (cattle) diacylglycerol O-acyltransferase 1 isoform X2 (BtDGAT1-X2).

SEQ ID NO:14—Nucleotide sequence of the protein coding region of *Bos taurus* (cattle) diacylglycerol O-acyltransferase 1 isoform X2 (BtDGAT1-X2) in pAT007, codon optimised for expression in yeast.

SEQ ID NO:15—Amino acid sequence of *Bubulus bubulis* (water buffalo) diacylglycerol O-acyltransferase 1 isoform X1 (BbDGAT1-X1).

SEQ ID NO:16—Nucleotide sequence of the protein coding region of *Bubulus bubulis* (water buffalo) diacylglycerol O-acyltransferase 1 isoform X1 (BbDGAT1-X1) in pAT008, codon optimised for expression in yeast.

SEQ ID NO:17—Amino acid sequence of *Bubulus bubulis* (water buffalo) diacylglycerol O-acyltransferase 1 isoform X2 (BbDGAT1-X2).

SEQ ID NO:18—Nucleotide sequence of the protein coding region of *Bubulus bubulis* (water buffalo) diacylglycerol O-acyltransferase 1 isoform X2 (BbDGAT1-X2) in pAT009, codon optimised for expression in yeast.

SEQ ID NO:19—Amino acid sequence of *Bubulus bubulis* (water buffalo) diacylglycerol O-acyltransferase 1 isoform X3 (BbDGAT1-X3).

SEQ ID NO:20—Nucleotide sequence of the protein coding region of *Bubulus bubulis* (water buffalo) diacylglycerol O-acyltransferase 1 isoform X3 (BbDGAT1-X3) in pAT010, codon optimised for expression in yeast.

SEQ ID NO:21—Amino acid sequence of *Bubulus bubulis* (water buffalo) diacylglycerol O-acyltransferase 1 isoform X4 (BbDGAT1-X4).

SEQ ID NO:22—Nucleotide sequence of the protein coding region of *Bubulus bubulis* (water buffalo) diacylglycerol O-acyltransferase 1 isoform X4 (BbDGAT1-X4) in pAT011, codon optimised for expression in yeast.

SEQ ID NO:23—Amino acid sequence of *Bubulus bubulis* (water buffalo) diacylglycerol O-acyltransferase 1 isoform X5 (BbDGAT1-X5).

SEQ ID NO:24—Nucleotide sequence of the protein coding region of *Bubulus bubulis* (water buffalo) diacylglycerol O-acyltransferase 1 isoform X5 (BbDGAT1-X5) in pAT012, codon optimised for expression in yeast.

SEQ ID NO:25—Amino acid sequence of *Bubulus bubulis* (water buffalo) diacylglycerol O-acyltransferase 1 isoform X6 (BbDGAT1-X6).

SEQ ID NO:26—Nucleotide sequence of the protein coding region of *Bubulus bubulis* (water buffalo) diacylglycerol O-acyltransferase 1 isoform X6 (BbDGAT1-X6) in pAT013, codon optimised for expression in yeast.

SEQ ID NO:27—Amino acid sequence of *Bubulus bubulis* (water buffalo) diacylglycerol O-acyltransferase 1 isoform X7 (BbDGAT1-X7).

SEQ ID NO:28—Nucleotide sequence of the protein coding region of *Bubulus bubulis* (water buffalo) diacylglycerol O-acyltransferase 1 isoform X7 (BbDGAT1-X7) in pAT014, codon optimised for expression in yeast.

SEQ ID NO:29—Amino acid sequence of *Bos taurus* (cattle) diacylglycerol O-acyltransferase 1 lactation isoform X1 (BtDGAT1lac).

SEQ ID NO:30—Nucleotide sequence of the protein coding region of *Bos taurus* (cattle) diacylglycerol O-acyltransferase 1 lactation isoform X1 (BtDGAT1lac) in pAT019, codon optimised for expression in yeast.

DETAILED DESCRIPTION OF THE INVENTION

General Techniques and Standard Definitions

Unless specifically defined otherwise, all technical and scientific terms used herein shall be taken to have the same meaning as commonly understood by one of ordinary skill in the art (e.g., in cell culture, fermentation, molecular genetics, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−20%, more preferably +/−10%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

As used herein, a "lipid" is any of a class of organic compounds that are or comprise fatty acids, which may be esterified or non-esterified, or their derivatives and are insoluble in water but soluble in organic solvents, for example in chloroform. As used herein, the term "extracted lipid" refers to a lipid composition which has been extracted from a microbial cell. The extracted lipid can be a relatively crude composition obtained by, for example, lysing the cells, or a more purified composition where most, if not all, of one or more or each of the water, nucleic acids, proteins and carbohydrates derived from the cells have been removed. Examples of purification methods are described below. In an embodiment, the extracted lipid comprises at least about 60%, at least about 70%, at least about 80%, at least about 90%, or at least about 95% (w/w) lipid by weight of the composition. The lipid may be solid or liquid at room temperature (25° C.), or a mixture of the two; when liquid it is considered to be an oil, when solid it is considered to be a fat. In an embodiment, extracted lipid of the invention has not been blended with another lipid produced by another source (for example, animal lipid). Alternatively, the extracted lipid may be blended with a different lipid, not comprising SCFA at the sn-3 position of TAG, such as for example plant oils such as soybean oil, canola oil, cornseed oil, palm oil, coconut oil, cottonseed oil or any combination thereof. In an embodiment, following extraction the ratio of SCFAs to other fatty acids has not been significantly altered (for example, no greater than a 10% or 5% alteration) when compared to the ratio in the cell, and/or the lipid has not been treated in a way to modify the positional distribution of the SCFA in the TAG molecules, for example by interesterification or transesterification. In another embodiment, the extracted lipid has not been exposed to a procedure, such as hydrogenation or fractionation, which may alter the ratio of SCFAs to other fatty acids when compared to the ratio in the intact cell or which alters the degree of saturation of the total fatty acid content of the lipid. In an embodiment, the lipid is essentially free of trans fatty acids, for example <0.5% by weight of the total fatty acid content are trans fatty acids. When the extracted lipid of the invention is comprised in an oil, the oil may further comprise non-fatty acid molecules such as sterols. In an embodiment, the lipid is essentially free of cholesterol, for example <0.5% or <0.25% by weight of the lipid is cholesterol.

As used herein, the term "non-polar lipid" refers to fatty acids and derivatives thereof which are soluble in organic solvents but insoluble in water and which are not charged at pH of 5-7. Non-polar lipids do not include phospholipids, galactolipids and sphingolipids, which are types of polar lipids. Typically, non-polar lipids are not soluble or very sparingly soluble in ethanol. The fatty acids may be free fatty acids and/or in an esterified form. Examples of esterified forms include, but are not limited to, triacylglycerol (TAG), diacylglycerol (DAG), monoacylglycerol (MAG). Non-polar lipids also include sterols, sterol esters and wax esters. Non-polar lipids are also known as "neutral lipids" or in some contexts referred to as "oils". Non-polar lipid may be a liquid at room temperature, or a solid, depending on the degree of unsaturation of the fatty acids in the non-polar lipid. Typically, the more saturated the fatty acid content, the higher the melting temperature of the lipid.

As used herein, an "oil" is a composition comprising predominantly lipid and which is a liquid at room temperature. For instance, oil of the invention preferably comprises at least 75%, at least 80%, at least 85% or at least 90% lipid by weight. Typically, a purified oil comprises at least 90% triacylglycerols (TAG) by weight of the lipid in the oil, preferably at least 95%, at least 96%, at least 97%, at least 98% TAG by weight. Minor components of an oil such as diacylglycerols (DAG), free fatty acids (FFA), phospholipid and sterols may be present as described herein.

As used herein, the term "fatty acid" refers to a carboxylic acid (or organic acid), often with a long aliphatic tail, either saturated or unsaturated. Unsaturated fatty acids include monounsaturated fatty acids and polyunsaturated fatty acids (PUFA). A fatty acid may be a free fatty acid (FFA) or esterified to a glycerol or glycerol-phosphate molecule, CoA molecule or other headgroup as known in the art, preferably esterified as part of a TAG molecule.

As used herein, the term "short chain fatty acid" or "SCFA" refers to fatty acids that have a carbon-carbon bonded chain of 2, 4, 6, or 8 carbon atoms in length, such as C2:0, C4:0, C6:0 and C8:0. Typically, the SCFA in the lipids of the invention are saturated i.e. do not have any carbon-carbon double bonds in their acyl chain, and have an unbranched acyl chain. SCFA as used herein do not include fatty acids having 9 or more carbon atoms in their acyl chain. As used herein, the term "medium chain fatty acid" or "MCFA" refers to fatty acids that have a carbon-carbon bonded chain of between 10 and 14 carbon atoms in length, such as C10:0, C12:0, C12:1, C14:0 and C14:1, typically a mixture of C10, C12 and C14 fatty acids is present in the lipid of the invention. Typically, the MCFA in the lipids of the invention are either saturated or monounsaturated, or preferably the lipid of the invention comprises both saturated and monounsaturated MCFA, and have an unbranched acyl chain. MCFA as used herein do not include fatty acids having less than 10 or more than 14 carbon atoms in their acyl chain. As used herein, the term "long chain fatty acid" or "LCFA" refers to fatty acids that have a carbon-carbon bonded chain of between 15 and 19 carbon atoms in length, such as C15:0, C16:0, C16:1, C17:0, C18:0, C18:1, C18:2 and C18:3 fatty acids. Typically, the LCFA in the lipid of the invention comprise both saturated and monounsaturated LCFA and have unbranched acyl chains. Typically, the lipid of the invention comprises some long chain PUFA (LC-PUFA), mainly C18:2, preferably less than 5% of the total fatty acid content, more preferably less than 3% or less than 2% of the total fatty acid content of the lipid is LC-PUFA. LCFA as used herein do not include fatty acids having less than 15 or more than 18 carbon atoms in their acyl chain.

"Saturated fatty acids" do not contain any double bonds or other functional groups along the chain. The term "saturated" refers to hydrogen, in that all carbons (apart from the carboxylic acid [—COOH] group) contain as many hydrogens as possible.

"Unsaturated fatty acids" are of similar form to saturated fatty acids, except that one or more alkene functional groups exist along the chain, with each alkene substituting a singly-bonded "—CH2—CH2—" part of the chain with a doubly-bonded "—CH=CH—" portion (that is, a carbon double bonded to another carbon). The two next carbon atoms in the chain that are bound to either side of the double bond can occur in a cis or trans configuration, preferably in the cis configuration.

As used herein, the term "monounsaturated fatty acid" refers to a fatty acid which comprises at least 12 carbon atoms in its carbon chain and only one alkene group (carbon-carbon double bond) in the chain. Monounsaturated fatty acids include C12:1Δ9, C14:1Δ9, C16:1Δ9, C18:1Δ9 and C18:1Δ11, each of which may be present in the TAG molecules of the lipid of the invention. As used herein, the terms "polyunsaturated fatty acid" or "PUFA" refer to a fatty acid which comprises at least 12 carbon atoms in its carbon chain and at least two alkene groups (carbon-carbon double bonds). PUFA include C18:2Δ9,12 and C18:3Δ9,12,15, each of which may be present in the TAG molecules of the lipid of the invention.

As used herein, "C4:0" refers to butyric acid, either esterified or non-esterified.

As used herein, "C6:0" refers to caproic acid, either esterified or non-esterified.

As used herein, "C8:0" refers to caprylic acid, either esterified or non-esterified.

As used herein, "C10:0" refers to capric acid, either esterified or non-esterified.

As used herein, "C12:0" refers to lauric acid, either esterified or non-esterified.

As used herein, "C14:0" refers to myristic acid, either esterified or non-esterified.

As used herein, "C15:0" refers to n-pentadecanoic acid, either esterified or non-esterified.

As used herein, "C16:1" refers to palmitoleic acid, or-hexadec-9-enoic acid, either esterified or non-esterified. which is an omega-7 monounsaturated fatty acid.

As used herein, "C16:0" refers to palmitic acid, either esterified or non-esterified.

As used herein, the term "total fatty acid (TFA) content" or variations thereof refers to the total amount of fatty acids in the cell on a weight basis, as a percentage of the weight of the cell. Unless otherwise specified, the weight of the cell is the dry weight. TFA content is measured by conversion of the fatty acids to FABE and measurement of the amount of FABE by GC, using addition of a known amount of a distinctive fatty acid standard as a quantitation standard in the GC (see Example 1). TFA therefore represents the weight of just the fatty acids, not the weight of the fatty acids and their linked moieties in the lipid.

"Triacylglyceride" or "TAG" is a glyceride in which the glycerol is esterified with three fatty acids which may be the same (e.g. as in tri-olein) or, more commonly, different. All three of the fatty acids may be different, or two of the fatty acids may be the same and the third is different. In the Kennedy pathway of TAG synthesis, DAG is formed as described above, and then a third acyl group is esterified to the glycerol backbone by the activity of DGAT.

"Diacylglyceride" or "DAG" is glyceride in which the glycerol is esterified with two fatty acids which may be the same or, preferably, different. As used herein, DAG comprises a hydroxyl group at a sn-1,3 or sn-2 position, and therefore DAG does not include phosphorylated molecules such as PA or PC. In the Kennedy pathway of DAG synthesis, the precursor sn-glycerol-3-phosphate (G3P) is esterified to two acyl groups, each coming from a fatty acid coenzyme A ester, in a first reaction catalysed by a glycerol-3-phosphate acyltransferase (GPAT) at position sn-1 to form LysoPA, followed by a second acylation at position sn-2 catalysed by a lysophosphatidic acid acyltransferase (LPAAT) to form phosphatidic acid (PA). This intermediate is then de-phosphorylated by PAP to form DAG.

"Monoacylglyceride" or "MAG" is glyceride in which the glycerol is esterified with one fatty acid. As used herein, MAG comprises a hydroxyl group at an sn-1/3 (also referred to as sn-1 MAG or 1-MAG or 1/3-MAG) or a sn-2 position (also referred to herein as 2-MAG), and therefore MAG does not include phosphorylated molecules such as PA or PC.

As used herein, the term "triacylglycerol (TAG) content" or variations thereof refers to the amount of TAG in the cell or in the extracted lipid, according to the context. TAG content can be calculated using techniques known in the art such as the sum of glycerol and fatty acyl moieties using a relation: % TAG by weight=100× ((41× total mol FAME/3)+(total g FAME−(15× total mol FAME)))/g, where 41 and 15 are molecular weights of glycerol moiety and methyl group, respectively (where FAME is fatty acid methyl esters).

As used herein, the term "fatty acid acyltransferase" refers to a protein which is capable of transferring an acyl group from acyl-CoA, PC or acyl-ACP, preferably acyl-CoA or PC, onto a substrate to form TAG, DAG or MAG. These acyltransferases include DGAT, such as DGAT1, DGAT2 and DAcT, and LPAAT. Other acyltransferases are PDAT, LPCAT and MGAT.

As used herein, the term "diacylglycerol acyltransferase" (EC 2.3.1.20; DGAT) refers to a protein which transfers a fatty acyl group from acyl-CoA to a diacylglycerol substrate to produce a triacylglycerol. The acyl-CoA and DAG molecules are therefore substrates of the DGAT, and TAG is one of the products of the DGAT. Thus, the term "diacylglycerol acyltransferase activity" refers to the transfer of acyl-CoA to diacylglycerol to produce triacylglycerol. There are three known types of DGAT referred to as DGAT1, DGAT2 and DGAT3 respectively. Amino acid sequences of DGAT enzymes include those disclosed herein and variants thereof.

As used herein, the term "1,2-diacyl-sn-glycerol:acetyl-CoA acetyltransferase" or "DAcT" refers to a sub-class of DGATs which are able to transfer an acetyl group to the sn-3 position of DAG to thereby form TAG. The DAcT may also be able to transfer the acyl groups from other acyl-CoA molecules, such as for example C4:0-CoA and/or C6:0-CoA.

As used herein, an "oleaginous" cell is one that is capable of storing large amounts of TAG, such as to 10% to 70% or 20% to 70% of their cell mass on a dry weight basis. The TAG content may depend on culture conditions, as is known in the art.

As used herein, a "heterotrophic" cell is one that is capable of utilizing organic materials as a carbon source for metabolism and growth. Heterotrophic organisms may also be able to grow autotrophically under suitable conditions.

As used herein, "fermentation" refers to a metabolic process that produces chemical changes in organic substrates through the action of enzymes in the cells, under conditions either lacking oxygen or having reduced levels of oxygen relative to air. In microorganisms, fermentation is the primary means of producing adenosine triphosphate (ATP) by the degradation of organic nutrients anaerobically.

Microbial Cells

A wide variety of different microbial cells can be used in the present invention. In an embodiment the microbial cells exist as single celled organisms, however such cells may clump together. Examples of microbial cells of the invention include fungal cells, bacterial cells and algal cells. Eukaryotic microbes are preferred over bacterial (prokaryotic) microbes. As used herein, the terms "microbial cell", "microbe" and "microorganism" mean the same thing.

In an embodiment, the microbial cells are suitable for fermentation. In another embodiment, the microbial cells are oleaginous cells. In another embodiment, microbial cells are heterotrophic cells. The microbial cells are preferably at least two of these, more preferably are characterised by all three of these features.

In an embodiment, the fungal cells are yeast cells. Examples of yeast cells useful for the invention include, but are not limited to, *Saccharomyces* sp. such as *Saccharomyces cerevisiae, Yarrowia* sp. such as *Yarrowia lipolytica, Pichia* sp. such as *Pichia pastoris, Candida* sp. such as *Candida rugosa, Aspergillus* sp. such as *Aspergillus niger, Cryptococcus* sp. such as *Cryptococcus curvatus, Lipomyces* sp. such as *Lipomyces starkeyi, Rhodosporidium* sp. such as *Rhodosporidium toruloides* Y4, *Rhodotorula* sp. such as *Rhodotorula glutinis* and *Trichosporon* sp. such as *Trichosporon fermentans.*

In an embodiment, the fungal cells are mold cells. Examples of mold cells useful for the invention include, but are not limited to, *Cunninghamella* sp. such as *Cunninghamella echinulate, Mortierella* sp. such as *Mortierella isabellina* or *Mortierella alpina, Mucorales* sp. such as *Mucorales fungi* and *Trichoderma* sp. such as *Trichoderma harzianum* Q2-37.

In an embodiment, the cells are bacterial cells. Examples of bacterial cells useful for the invention include, but are not limited to, *Acinetobacter* such as *Acinetobacter baylyi* ADP1(MT), *Alcanivorax* sp. such as *Alcanivorax borkumensis* SK2, *Gordonia* sp. such as DG, *Mycobacterium* sp. such as *Mycobacterium tuberculosis* H37Rv, *Nocardia* sp. such as *Nocardia globerula* 432, *Rhodococcus* sp. such as *Rhodococcus opacus* PD630, and *Streptomyces* sp. such as *Streptomyces coelicolor* TR0958 or TR0123.

In an embodiment, the cells are algal cells such as microalgal, or Bacillariophyceae, cells. Examples of algal cells useful for the invention include, but are not limited to, *Prototheca* sp. such as *Prototheca moriformis, Thraustochytrium* spp., *Chlorella* sp. such as *Chlorella protothecoides, Chlorella vulgaris* or *Chlorella ellipsoidea* YSR03, *Schizochytrium* sp. such as *Schizochytrium* strain FCC-1324, *Dunaliella* sp., *Haematococcus* sp. such as *Haematococcus pluvialis, Neochloris* sp. such as *Neochloris oleabundans* such as strain UTEX #1185, *Pseudochlorococcum* sp., *Scenedesmus* sp. such as *Scenedesmus obliquus, Tetraselmis* sp. such as *Tetraselmis chui* or *Tetraselmis tetrathele, Chaetoceros* sp. such as *Chaetoceros calcitrans* CS 178, *Chaetoceros gracilis* or *Chaetoceros muelleri, Nitzschia* sp. such as *Nitzschia* cf. *pusilla* YSR02, *Phaeodactylum* sp. such as *Phaeodactylum tricornutum* F&M-M40, *Skeletonema* sp. such as strain CS 252, *Thalassiosira* sp. such as *Thalassiosira pseudonana* CS 173, *Cryptecodinium* sp. such as *Crypthecodinium cohnii, Isochrysis* sp. such as *Isochrysis zhangjiangensis, Nannochloropsis* sp. such as *Nannochloropsis oculata* such as strain NCTU-3, *Pavlova* sp. such as *Pavlova salina* CS 49, *Rhodomonas* sp. and *Thalassiosira* sp. such as *Thalassiosira weissflogii.*

Polypeptides

The terms "polypeptide" and "protein" are generally used interchangeably.

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over the entire length of the reference amino acid sequence. The polypeptide or class of polypeptides may have the same enzymatic activity as, or a different activity than, or lack the activity of, the reference polypeptide. Preferably, the polypeptide has an enzymatic activity of at least 10%, at least 50%, at least 75% or at least 90%, of the activity of the reference polypeptide.

A polynucleotide defined herein may encode a biologically active fragment of an enzyme such as an acyl transferase. As used herein a "biologically active" fragment is a portion of a polypeptide defined herein which maintains a defined activity of a full-length reference polypeptide, for example possessing desaturase and/or elongase activity or other enzyme activity. Biologically active fragments as used herein exclude the full-length polypeptide. Biologically active fragments can be any size portion as long as they maintain the defined activity. Preferably, the biologically active fragment maintains at least 10%, at least 50%, at least 75% or at least 90%, of the activity of the full length protein.

With regard to a defined polypeptide or enzyme, it will be appreciated that % identity figures higher than those provided herein will encompass preferred embodiments. Thus, where applicable, in light of the minimum % identity figures, it is preferred that the polypeptide/enzyme comprises an amino acid sequence which is at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO. In an embodiment, for each of the ranges listed above, the % identity does not include 100% i.e. the amino acid sequence is different to the nominated SEQ ID NO.

Amino acid sequence variants/mutants of the polypeptides of the defined herein can be prepared by introducing appropriate nucleotide changes into a nucleic acid defined herein, or by in vitro synthesis of the desired polypeptide. Such variants/mutants include, for example, deletions, insertions or substitutions of residues within the amino acid sequence. A combination of deletion, insertion and substitution can be made to arrive at the final construct, provided that the final peptide product possesses the desired enzyme activity.

Mutant (altered) peptides can be prepared using any technique known in the art. For example, a polynucleotide defined herein can be subjected to in vitro mutagenesis or DNA shuffling techniques as broadly described by Harayama (1998). Products derived from mutated/altered DNA can readily be screened using techniques described herein to determine if they possess, for example, desaturase or elongase activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites which are not conserved amongst naturally occurring desaturases or elongases. These sites are preferably substituted in a relatively conservative manner in order to maintain enzyme activity. Such conservative substitutions are shown in Table 1 under the heading of "exemplary substitutions".

In a preferred embodiment a mutant/variant polypeptide has only, or not more than, one or two or three or four conservative amino acid changes when compared to a naturally occurring polypeptide. Details of conservative amino acid changes are provided in Table 3. As the skilled person would be aware, such minor changes can reasonably be predicted not to alter the activity of the polypeptide when expressed in a recombinant cell.

Polynucleotides

The invention also provides for the use of polynucleotides which may be, for example, a gene, an isolated polynucleotide, a chimeric genetic construct such as a chimeric DNA. It may be DNA or RNA of genomic or synthetic origin, double-stranded or single-stranded, and combined with carbohydrate, lipids, protein or other materials to perform a particular activity defined herein. The term "polynucleotide" is used interchangeably herein with the term "nucleic acid molecule".

In an embodiment, the polynucleotide is non-naturally occurring. Examples of non-naturally occurring polynucleotides include, but are not limited to, those that have been codon optimised for expression in microbial cell, those that have been mutated (such as by using methods described herein), and polynucleotides where an open reading frame encoding a protein is operably linked to a promoter to which it is not naturally associated (such as in the constructs described herein).

TABLE 1

| Exemplary substitutions. | |
| --- | --- |
| Original Residue | Exemplary Substitutions |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| He (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

As used herein, a "chimeric DNA" or "chimeric genetic construct" or similar refers to any DNA molecule that is not a native DNA molecule in its native location, also referred to herein as a "DNA construct". Typically, a chimeric DNA or chimeric gene comprises regulatory and transcribed or protein coding sequences that are not found operably linked together in nature i.e. that are heterologous with respect to each other. Accordingly, a chimeric DNA or chimeric gene may comprise regulatory sequences and coding sequences that are derived from different sources, or regulatory sequences and coding sequences derived from the same source, but arranged in a manner different than that found in nature.

The term "exogenous" in the context of a polynucleotide refers to the polynucleotide when present in a cell in an altered amount compared to its native state. In one embodiment, the cell is a cell that does not naturally comprise the polynucleotide. However, the cell may be a cell which comprises a non-endogenous polynucleotide resulting in an altered amount of production of the encoded polypeptide. An exogenous polynucleotide includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide operably linked to a promoter suitable of driving transcription of the open reading frame in a cell of interest.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO. In an embodiment, for each of the ranges listed above, the % identity does not include 100% i.e. the nucleotide sequence is different to the nominated SEQ ID NO.

Polynucleotides may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above). It is thus apparent that polynucleotides can be either from a naturally occurring source or recombinant. Preferred polynucleotides are those which have coding regions that are codon-optimised for translation in microbial cells, as is known in the art.

Recombinant Vectors

Recombinant expression can be used to produce recombinant cells of the invention. Recombinant vectors contain heterologous polynucleotide sequences, that is, polynucleotide sequences that are not naturally found adjacent to polynucleotide molecules defined herein that preferably are derived from a species other than the species from which the polynucleotide molecule(s) are derived. The vector can be either RNA or DNA and typically is a plasmid. Plasmid vectors typically include additional nucleic acid sequences that provide for easy selection, amplification, and transformation of the expression cassette in prokaryotic cells, e.g., pYES-derived vectors, pUC-derived vectors, pSK-derived vectors, pGEM-derived vectors, pSP-derived vectors, or pBS-derived vectors. Suitable yeast expression vectors include the pPIC series of vectors, yeast integrating plasmids (YIp), yeast replicating plasmids (YRp), yeast centromere plasmids (YCp), and yeast episomal plasmids (YEp). Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of microbial cells. The recombinant vector may comprise more than one polynucleotide defined herein, for example three, four, five or six polynucleotides defined herein in combination, preferably a chimeric genetic construct described herein, each polynucleotide being operably linked to expression control sequences that are operable in the cell.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance. For example, an intron in a 5' UTR sequence or towards the 5' end of a protein coding region can contain a transcriptional enhancer, providing an increased expression level, for example an FBAIN promoter region.

To facilitate identification of transformants, the nucleic acid construct desirably comprises a selectable or screenable marker gene as, or in addition to, the foreign or exogenous polynucleotide. By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., ($\beta$-glucuronidase, luciferase, GFP or other enzyme activity not present in untransformed cells). The marker gene and the nucleotide sequence of interest do not have to be linked. The actual choice of a marker is not crucial as long as it is functional (i.e., selective) in combination with the cells of choice.

Examples of selectable markers are markers that confer antibiotic resistance such as ampicillin, erythromycin, chloramphenicol or tetracycline resistance, preferably kanamycin resistance.

Recombinant yeast of the invention may comprise a reporter gene which either encodes a galactosidase or a selectable growth marker.

The "galactosidase" may be any enzyme which cleaves a terminal galactose residue(s) from a variety of substrates, and which is able to also cleave a substrate to produce a detectable signal. In an embodiment, the galactosidase is a $\beta$-galactosidase such as bacterial (for instance from E. coli) LacZ. In an alternate embodiment, the galactosidase is an $\alpha$-galactosidase such as yeast (for instance S. cerevisiae) Mel-1. $\beta$-galactosidase activity may be detected using substrates for the enzyme such as X-gal (5-bromo-4-chloro-indolyl-$\beta$-D-galactopyranoside) which forms an intense blue product after cleavage, ONPG (o-nitrophenyl galactoside) which forms a water soluble yellow dye with an absorbance maximum at about 420 nm after cleavage, and CPRG (chlorophenol red-$\beta$-D-galactopyranoside) which yields a water-soluble red product measurable by spectrophotometry after cleavage. a-galactosidase activity may be detected using substrates for the enzyme such as o-nitrophenyl $\alpha$-D-galactopyranoside which forms an indigo dye after cleavage, and chlorophenol red-$\alpha$-D-galactopyranoside which yields a water-soluble red product measurable by spectrophotometry after cleavage. Kits for detecting galactosidase expression in yeast are commercially available, for instance the $\beta$-galactosidase (LacZ) expression kit from Thermo Scientific.

Preferably, the selectable growth marker is a nutritional marker or antibiotic resistance marker.

Typical yeast selectable nutritional markers include, but are not limited to, LEU2, TRP1, HIS3, HIS4, URA3, URA5, SFA1, ADE2, MET15, LYS5, LYS2, ILV2, FBA1, PSE1, PDI1 and PGK1. Those skilled in the art will appreciate that any gene whose chromosomal deletion or inactivation results in an unviable host, so called essential genes, can be used as a selective marker if a functional gene is provided on the, for example, plasmid, as demonstrated for PGK1 in a pgk1 yeast strain. Suitable essential genes can be found within the Stanford Genome Database (SGD) (http://db-.yeastgenome.org). Any essential gene product (e.g. PDI1, PSE1, PGK1 or FBA1) which, when deleted or inactivated, does not result in an auxotrophic (biosynthetic) requirement, can be used as a selectable marker on a, for example, plasmid in a yeast host cell that, in the absence of the plasmid, is unable to produce that gene product, to achieve increased plasmid stability without the disadvantage of requiring the cell to be cultured under specific selective conditions. By "auxotrophic (biosynthetic) requirement" we include a deficiency which can be complemented by additions or modifications to the growth medium.

Expression

Expression vectors can direct gene expression in microbial cells. As used herein, an expression vector is a vector that is capable of transforming a host cell and of effecting expression of one or more specified polynucleotide molecule(s). Expression vectors useful for the invention contain regulatory sequences such as transcription control sequences, translation control sequences, origins of replication, and other regulatory sequences that are compatible with the recombinant cell and that control the expression of polynucleotide molecules of the present invention. In particular, polynucleotides or vectors useful for the present invention include transcription control sequences. Transcription control sequences are sequences which control the initiation, elongation, and termination of transcription. Particularly important transcription control sequences are those which control transcription initiation, such as promoter and enhancer sequences. Suitable transcription control sequences include any transcription control sequence that can function in at least one of the recombinant cells of the present invention. The choice of the regulatory sequences used depends on the target microbial cell. A variety of such transcription control sequences are known to those skilled in the art.

Yeast cells are typically transformed by chemical methods (e.g., as described by Rose et al., 1990, Methods in Yeast Genetics, Cold Spring Harbor Laboratory Press, Cold Spring Harbor, N.Y., and in Kawai et al., 2010). The cells are typically treated with lithium acetate to achieve transformation efficiencies of approximately $10^4$ colony-forming units (transformed cells)/μg of DNA. Other standard procedures for transforming yeast include i) the spheroplast method which, as the name suggests, relies on the production of yeast spheroplasts, ii) the biolistic method where DNA coated metal microprojectiles are shot into the cells, and iii) the glass bead methods which relies on the agitation of the yeast cells with glass beads and the DNA to be delivered to the cell. Of course, any suitable means of introducing nucleic acids into yeast cells can be used.

It is well known that transformation of organisms, such as yeast, with exogenous plasmids can lead to clonal differences in the penetrance of the transformed gene, due to differences in copy number or other factors. It is therefore advisable to screen two or more independent clonal isolates for each transformed receptor in order to maximise the likelihood of identifying suitable receptor=ligand pairs during screening. Different clonal isolates may be screened independently or may be combined into a single well for screening. The latter option may be particularly convenient where a nutritional reporter is used rather than a colorimetric reporter.

"Constitutive promoter" refers to a promoter that directs expression of an operably linked transcribed sequence in the cell without the need to be induced by specific growth conditions. Examples of constitutive promoters useful for yeast cells of the invention include, but are not limited to, a yeast PGK (phosphoglycerate kinase) promoter, a yeast ADH-1 (alcohol dehydrogenase) promoter, a yeast ENO (enolase) promoter, a yeast glyceraldehyde 3-phosphate dehydrogenase promoter (GPD) promoter, a yeast PYK-1 (pyruvate kinase) promoter, a yeast translation-elongation factor-1-alpha promoter (TEF) promoter and a yeast CYC-1 (cytochrome c-oxidase promoter) promoter. In a preferred embodiment, a yeast promoter is a *S. cerevisiae* promoter. In another embodiment, the constitutive promoter may not have been derived from yeast. Examples of such promoters useful for the invention include, but are not limited to, the cauliflower mosaic virus 35S promoter, the glucocorticoid response element, and the androgen response element. The constitutive promoter may be the naturally occurring molecule or a variant thereof comprising, for example, one, two or three nucleotide substitutions which do not abolish (and preferably enhance) promoter function.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules defined herein include, but are not limited to, integration of the polynucleotide molecule into one or more host cell chromosomes, addition of stability sequences to mRNAs, substitutions or modifications of transcription control signals (e.g., promoters, operators, enhancers), substitutions or modifications of translational control signals (e.g., ribosome binding sites, Shine-Dalgarno sequences), modification of polynucleotide molecules to correspond to the codon usage of the host cell, and the deletion of sequences that destabilize transcripts.

Any method can be used to introduce a nucleic acid molecule into a microbial cell and many such methods are well known. For example, transformation and electroporation are common methods for introducing nucleic acid into yeast cells (See, e.g., Gietz et al., 1992; Ito et al., 1983; and Becker et al., 1991).

In an embodiment, the integration of a gene of interest into a specific chromosomal site in a microbial cell occurs via homologous recombination. According to this embodiment, an integration cassette containing a module comprising at least one marker gene and/or the gene to be integrated (internal module) is flanked on either side by DNA fragments homologous to those of the ends of the targeted integration site (recombinogenic sequences). After transforming the microbial cell with the cassette by appropriate methods, a homologous recombination between the recombinogenic sequences may result in the internal module replacing the chromosomal region in between the two sites of the genome corresponding to the recombinogenic sequences of the integration cassette (Orr-Weaver et al., 1981).

In an embodiment, the integration cassette for integration of a gene of interest into a microbial cell includes the heterologous gene under the control of an appropriate promoter together with a selectable marker flanked by recombinogenic sequences for integration of a heterologous gene into the microbial cell chromosome. In an embodiment, the heterologous gene includes any of the acyltransferase genes described herein.

Where deletion of an endogenous gene is desired, the integration cassette can comprise a selectable marker (without any other heterologous gene sequence) flanked by DNA fragments homologous to those of the ends (and/or neighbouring sequences) of the endogenous gene targeted for deletion. Other methods suitable for deleting or mutating endogenous genes (e.g., using site-specific or RNA-guided nucleases) are described below.

The selectable marker gene can be any marker gene used in microbial cells, including but not limited to, HIS3, TRP1, LEU2, URA3, bar, ble, hph, and kan. The recombinogenic sequences can be chosen at will, depending on the desired integration site suitable for the desired application.

In another embodiment, integration of a gene into the chromosome of the microbial cell may occur via random integration (Kooistra et al., 2004).

Additionally, in an embodiment, certain introduced marker genes are removed from the genome using techniques well known to those skilled in the art. For example, URA3 marker loss can be obtained by plating URA3 containing cells in FOA (5-fluoro-orotic acid) containing medium and selecting for FOA resistant colonies (Boeke et al., 1984).

The exogenous nucleic acid molecule contained within a microbial cell of the disclosure can be maintained within that cell in any form. For example, exogenous nucleic acid molecules can be integrated into the genome of the cell or maintained in an episomal state that can stably be passed on ("inherited") to daughter cells. Such extra-chromosomal genetic elements (such as plasmids, mitochondrial genome, etc.) can additionally contain selection markers that ensure the presence of such genetic elements in daughter cells. Moreover, the microbial cells can be stably or transiently transformed. In addition, the microbial cells described herein can contain a single copy, or multiple copies of a particular exogenous nucleic acid molecule as described above.

Cell Culture

Effective culture conditions are known to those skilled in the art and include, but are not limited to, suitable media, bioreactor, temperature, pH and oxygen conditions that permit lipid production. A suitable medium refers to any medium in which a cell is cultured to produce lipid defined herein. Such medium typically comprises an aqueous medium having assimilable carbon, nitrogen and phosphate sources, and appropriate salts, minerals, metals and other nutrients, such as vitamins. Cells defined herein can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Lipid Extraction

Extraction of the lipid from microbial cell of the invention uses analogous methods to those known in the art for lipid extraction from oleaginous microorganisms (such as described in Patel et al., 2018). In one embodiment, the extraction is performed by solvent extraction where an organic solvent (e.g., hexane) is mixed with at least the biomass, preferably after the biomass is dried and ground, but it can also be performed under wet conditions. The solvent dissolves the lipid in the cells, which solution is then separated from the biomass by a physical action (e.g., ultra sonication). Ultrasonication is one of the most extensively used pretreatment method to disrupt the cellular integrity of microbial cells. Other pretreatment methods can include microwave irradiation, high-speed homogenization, high-pressure homogenization, bead beating, autoclaving, and thermolysis. The organic solvent can then be separated from the non-polar lipid (e.g., by distillation). This second separation step yields non-polar lipid from the cells and can yield a re-usable solvent if one employs conventional vapor recovery.

In solvent extraction, an organic solvent (e.g., hexane) is mixed with at least the biomass of the microbial cell, preferably after the biomass is dried and ground. The solvent dissolves the lipid in the biomass and the like, which solution is then separated from the biomass by mechanical action (e.g., with the processes above). This separation step can also be performed by filtration (e.g., with a filter press or similar device) or centrifugation etc. The organic solvent can then be separated from the non-polar lipid (e.g., by distillation). This second separation step yields non-polar lipid from the microbial cell and can yield a re-usable solvent if one employs conventional vapor recovery.

The lipid extracted from the microbial cells of the invention may be subjected to normal oil processing procedures. As used herein, the term "purified" when used in connection with lipid of the invention typically means that that the extracted lipid has been subjected to one or more processing steps to increase the purity of the lipid component. Such processing steps may, for example, remove one or more other cellular components from the extracted lipid. A purification step may comprise one or more or all of the group consisting of: degumming, deodorising, decolourising, drying and/or fractionating the extracted oil. However, as used herein, the term "purified" does not include a transesterification process or other process which alters the fatty acid composition of the lipid or oil of the invention so as to change the fatty acid composition of the total fatty acid content. Expressed in other words, in a preferred embodiment the fatty acid composition of the purified lipid is essentially the same as that of the unpurified lipid.

Degumming

Degumming is an early step in the refining of lipids in a liquid form (oil) and its primary purpose is the removal of most of the phospholipids from the oil, which may be present as approximately 1-2% of the total extracted lipid. Addition of ~2% of water, typically containing phosphoric acid, at 70-80° C. to the crude oil results in the separation of most of the phospholipids accompanied by trace metals and pigments. The insoluble material that is removed is mainly a mixture of phospholipids and is also known as lecithin. Degumming can be performed by addition of concentrated phosphoric acid to the crude extracted lipid to convert non-hydratable phosphatides to a hydratable form, and to chelate minor metals that are present. Gum is separated from the oil by centrifugation.

Alkali Refining

Alkali refining is one of the refining processes for treating lipid in the form of an oil, sometimes also referred to as neutralization. It usually follows degumming and precedes bleaching. Following degumming, the oil can treated by the addition of a sufficient amount of an alkali solution to titrate all of the fatty acids and phosphoric acids, and removing the soaps thus formed. Suitable alkaline materials include sodium hydroxide, potassium hydroxide, sodium carbonate, lithium hydroxide, calcium hydroxide, calcium carbonate and ammonium hydroxide. This process is typically carried out at room temperature and removes the free fatty acid fraction. Soap is removed by centrifugation or by extraction into a solvent for the soap, and the neutralised oil is washed with water. If required, any excess alkali in the oil may be neutralized with a suitable acid such as hydrochloric acid or sulphuric acid.

Bleaching

Bleaching is a refining process in which oils are heated at 90-120° C. for 10-30 minutes in the presence of a bleaching earth (0.2-2.0%) and in the absence of oxygen by operating with nitrogen or steam or in a vacuum. This step in oil processing is designed to remove unwanted pigments and the process also removes oxidation products, trace metals, sulphur compounds and traces of soap.

Deodorization

Deodorization is a treatment of oils and fats at a high temperature (200-260° C.) and low pressure (0.1-1 mm Hg). This is typically achieved by introducing steam into the oil at a rate of about 0.1 ml/minute/100 ml of oil. After about 30 minutes of sparging, the oil is allowed to cool under vacuum. The oil is typically transferred to a glass container and flushed with argon before being stored under refrigeration. This treatment improves the colour of the oil and removes a majority of the volatile substances or odorous compounds including any remaining free fatty acids, monoacylglycerols and oxidation products.

Transesterification

As used herein, "transesterification" means a process that exchanges the fatty acids within and between TAGs (inter-esterification) or transfers the fatty acids to another alcohol to form an ester. This may initially involve releasing fatty acids from the TAGs as free fatty acids or it may directly produce fatty acid esters, preferably fatty acid methyl esters or ethyl esters. In a transesterification reaction of the TAG with an alcohol such as methanol or ethanol, the alkyl group of the alcohol forms an ester linkage with the acyl groups (including the SCFA) of the TAG. When combined with a fractionation process, transesterification can be used to modify the fatty acid composition of lipids (Marangoni et al., 1995). Transesterification can use either chemical (e.g. strong acid or base catalysed) or enzymatic means, the latter using lipases which may be position-specific (sn-1/3 or sn-2 specific) for the fatty acid on the TAG, or having a preference for some fatty acids over others (Speranza et al, 2012). The fatty acid fractionation to increase the concentration of LC-PUFA in an oil can be achieved by any of the methods known in the art, such as, for example, freezing crystallization, complex formation using urea, molecular distillation, supercritical fluid extraction, counter current chromatography and silver ion complexing. Complex formation with urea is a preferred method for its simplicity and efficiency in reducing the level of saturated and monounsaturated fatty acids in the oil (Gamez et al., 2003). Initially, the TAGs of the oil are split into their constituent fatty acids, often in the form of fatty acid esters, by hydrolysis under either acid or base catalysed reaction conditions, whereby one mol of TAG is reacted with at least 3 mol of alcohol (e.g. ethanol for ethyl esters or methanol for methyl esters) with excess alcohol used to enable separation of the formed alkyl esters and the glycerol that is also formed, or by lipases. These free fatty acids or fatty acid esters, which are usually unaltered in fatty acid composition by the treatment, may then be mixed with an ethanolic solution of urea for complex formation. The saturated and monounsaturated fatty acids easily complex with urea and crystallize out on cooling and may subsequently be removed by filtration. The non-urea complexed fraction is thereby enriched with LC-PUFA.

Food and Feedstuffs

The present invention includes compositions which can be used as a food or beverage for human consumption or a feedstuff for animal consumption, preferably at least a food for human consumption. For purposes of the present invention, a food, beverage or feedstuff is a preparation for human or animal consumption which when taken into the body (a) serve to nourish or build up tissues or supply energy; and/or (b) maintain, restore or support adequate nutritional status or metabolic function. Food and beverages of the invention includes nutritional compositions for babies and/or young children such as, for example, infant formula.

A food, beverage or feedstuff of the invention comprises, for example, extracted lipid of the invention, the microbial cell of the invention, or the composition of the invention.

The food, beverage or feedstuff of the present invention comprises an oil, fatty acid ester, or fatty acid produced directly or indirectly by use of the methods, cells disclosed herein. The composition may either be in a solid or liquid form. Additionally, the composition may include edible macronutrients, protein, carbohydrate, vitamins, and/or minerals in amounts desired for a particular use. The amounts of these ingredients will vary depending on whether the composition is intended for use with normal individuals or for use with individuals having specialized needs, such as individuals suffering from metabolic disorders and the like.

Examples of suitable ingredients with nutritional value include, but are not limited to, macronutrients such as edible fats, carbohydrates and proteins. Examples of such edible fats include, but are not limited to, coconut oil, borage oil, fungal oil, black current oil, soy oil, and mono- and diglycerides. Examples of such carbohydrates include (but are not limited to): glucose, edible lactose, and hydrolyzed starch. Additionally, examples of proteins which may be utilized in the nutritional composition of the invention include (but are not limited to) soy proteins, electrodialysed whey, electrodialysed skim milk, milk whey, or the hydrolysates of these proteins.

With respect to vitamins and minerals, the following may be added to the food/feedstuff of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

Additional ingredients include food-grade oils such as canola, corn, sunflower, soybean, olive or coconut oil, seasoning agents such as edible salts (e.g., sodium or potassium chloride) or herbs (e.g., rosemary, thyme, basil, sage, or mint), flavouring agents, proteins (e.g., soy protein isolate, wheat glutin, pea vicilin, and/or pea legumin), protein concentrates (e.g., soy protein concentrate), emulsifiers (e.g., lecithin), gelling agents (e.g., k-carrageenan or gelatin), fibers (e.g., bamboo filer or inulin), or minerals (e.g., iodine, zinc, and/or calcium).

Foods, beverages and feedstuffs of the invention also can include a natural coloring agent such as turmeric or beet juice, or an artificial coloring agent such as azo dyes, triphenylmethanes, xanthenes, quinines, indigoids, titanium dioxide, red #3, red #40, blue #1, or yellow #5.

Foods, beverages and feedstuffs of the invention also can include shelf life extenders such as carbon monoxide, nitrites, sodium metabisulfite, Bombal, vitamin E, rosemary extract, green tea extract, catechins and other anti-oxidants.

The components utilized in the food, beverage or feedstuff compositions of the present invention can be of semi-purified or purified origin. By semi-purified or purified is meant a material which has been prepared by purification of a natural material or by de novo synthesis.

A food, beverage or feedstuff composition of the present invention may also be added to food even when supplementation of the diet is not required. For example, the composition may be added to food of any type, including (but not limited to): margarine, modified butter, cheeses, milk, yogurt, chocolate, candy, snacks, salad oils, cooking oils, cooking fats, meats, fish and beverages.

In some embodiments, the food, beverage or feedstuff ingredient or food, beverage or feedstuff is a dairy substitute. In some embodiments, the food, beverage or feedstuff is dairy-free. In one embodiment, the food or feedstuff is a dairy-free milk, a dairy-free butter, a dairy-free cheese, or a dairy-free yoghurt.

In an embodiment, the food, beverage or feedstuff has no components derived from an animal. Thus, in a preferred embodiment, at least some of the ingedients are plant material or material derived from a plant. In some embodiments, the food, beverage or feedstuff can be lactose free, soy-free, wheat-free, yeast-free, MSG-free, and/or free of protein hydrolysis products.

Furthermore, feedstuffs of the invention can be used in aquaculture of fish or crustaceans such as, for example, prawns for human or animal consumption. Preferred fish are salmon.

Foods, beverages and feedstuffs described herein can be assessed using trained human panelists. The evaluations can involve eyeing, feeling, chewing, smelling and/or tasting of the product to judge product appearance, color, integrity, texture, flavour, and mouth feel, etc. Panelists can be served samples under red or under white light. A scale can be used to rate the overall acceptability or quality of the food or specific quality attributes such dairy-likeness, texture, and flavour.

EXAMPLES

Example 1. Materials and Methods

Microbial Strains and Cloning Vectors

*Saccharomyces cerevisiae* strain INVSc1 was used as a host strain with the pYES2 plasmid as the base vector for testing various lipid modification genes in yeast. The strain and plasmid were obtained from Invitrogen (Catalog No. V825-20, Invitrogen). The genotype of INVSc1 was: MATa his3Δ1 leu2 trp1-289 ura3-52/MATα his3Δ1 leu2 trp1-289 ura3-52, and its phenotype was: His-, Leu-, Trp-, Ura-. The pYES2 vector had unique HindIII and XhoI restriction enzyme sites which were used for insertion of DNA fragments encoding various proteins as described below. The pYES2 expression vector contained a URA3 gene as a selectable marker gene for introduction into yeast strains that were Ura-, a 2μ origin of replication for high copy maintenance, and a Gal1 promoter for expression of the protein coding regions in yeast. The plasmid also contained an ampicillin resistance gene for selection in *E. coli* during cloning experiments.

Two strains of *Yarrowia lipolytica* were obtained from the American Type Culture Collection (Manassas VA, USA): Strain JM23 (ATCC 90812) having the genotype leu235 lys512 ura318 xpr2::LYS5B, and strain IFP29 (ATCC 20460) having the genotype leu235 lys512 ura318 xpr2:: LYS5B.

Recombinant DNA Methods

Derivatives of pYES2 having single genes inserted for testing in yeast were made by inserting protein coding regions between the unique HindIII and XhoI sites or other restriction enzyme sites in the plasmid as appropriate by standard cloning methods. The *E. coli* strain DH5α was used for cloning and plasmid propagation and DNA preparation according to standard methods.

The GoldenGate (GG) method (Larroude et al., 2018) allows for rapid and efficient combinatorial assembly of multiple expression cassettes in a single vector and was therefore used to make multigene constructs for testing in *S. cerevisiae* or *E lipolytica*. GG DNA parts and donor vectors, also called L0 vectors, were obtained from Celinska et al. (2017) and Larroude et al. (2018) and Addgene, USA. The DNA parts included promoters (GGE146, GGE151 and GGE294), terminators (GGE014, GGE015, GGE080, GGE020 and GGE021) and the backbone assembly vector (destination vector) was GGE114.

Protein coding regions for insertion into the vectors by GG assembly were codon optimised for *S. cerevisiae* or *Y. lipolytica* using Twist Bioscience and GeneArt online software (Twist Bioscience: www.twistbioscience.com/products/genes; ThermoFisher/GeneArt: www.thermofisher. com/au/en/home/life-science/cloning/gene-synthesis/geneart-gene-synthesis.html) and synthesised either by Twist Bioscience or GeneArt (ThermoFisher, USA), or in the lab. Internal BsaI restriction enzyme sites were avoided in the codon optimised nucleotide sequences of the protein coding regions as BsaI sites were used in the GG assembly method. NotI restriction enzyme sites were also avoided within the nucleotide sequences as NotI was used for linearizing the genetic constructs for transformation of *Y. lipolytica*. When one, two or three genes were to be inserted into a single vector, the individual components were designed with 4-nucleotide overhangs immediately 5' of each translation start codon (ATG) and 3' of the translation stop codon, with the sequence of each 4-nucleotide overhang depending on the position of the component in the backbone vector GGE114, according to Table 2. The external BsaI site with the appropriate 4-nt overhang was added to the 5' end of each DNA strand.

TABLE 2

| Nucleotide sequences of overhangs used in GoldenGate cloning method | | |
|---|---|---|
| Position | 5' overhang | 3' overhang |
| One gene insertion | | |
| Promoter 1 | ACGG | AATG |
| Gene 1 | AATG | TCTA |
| Terminator 1 | TCTA | GAGT |

TABLE 2-continued

| Nucleotide sequences of overhangs used in GoldenGate cloning method | | |
| --- | --- | --- |
| Position | 5' overhang | 3' overhang |
| Two gene insertion | | |
| Promoter 1 | ACGG | AATG |
| Gene 1 | AATG | TCTA |
| Terminator 1 | TCTA | GCTT |
| Promoter 2 | GCTT | ACAA |
| Gene 2 | ACAA | GGAT |
| Terminator 2 | GGAT | GAGT |
| Three gene insertion | | |
| Promoter 1 | ACGG | AATG |
| Gene 1 | AATG | TCTA |
| Terminator 1 | TCTA | GCTT |
| Promoter 2 | GCTT | ACAA |
| Gene 2 | ACAA | GGAT |
| Terminator 2 | GGAT | GTCA |
| Promoter 3 | GTCA | CCAC |
| Gene 3 | CCAC | GTAT |
| Terminator 3 | GTAT | GAGT |

The protein coding regions were synthesised in a cloning vector having a kanamycin selection marker gene to avoid any false positives when performing the GG reaction with the GG backbone vector GGE114 which had an ampicillin selectable marker gene. The *E. coli* strain DH5α was used for cloning and plasmid propagation according to standard methods. Antibiotics were used as appropriate for selecting transformed cells, for example ampicillin was added at 100 μg/mL for selection of constructs having an ampicillin selectable marker gene.

The destination vector GGE114 contained the red fluorescence protein (RFP) chromophore, which acts as a colour-based visual marker for negative cloning in *E. coli,* as described by Larroude et al. (2018). The vector GGE114 was a preassembled destination vector that, in addition to the bacterial replicon, contained popular bricks ZETA sequences in the place of InsUp and InsDown fragments and the URA3 marker with a view to reducing the number of fragments to assemble when employing this combination, into the backbone vector pYES2 which contained a 2μ origin for high-copy maintenance. In this case, the RFP was between the URA3 marker and the ZETA down. In the presence of BsaI enzyme, the RFP was released and the one, two or three transcription units (TU; promoter-protein coding region-terminator) were inserted.

The GG assembly reaction mixes contained equimolar quantities (50 ng) of the GG backbone vector such as GGE114 and other DNA components (donor vectors) in a final volume of 7.5 μl, by adding 0.75 μl 10× T4 ligase buffer, 0.75 μl 10× BSA (bovine serum albumin), 0.75 μl BsaI HF-V2 (NEB), 0.5 μl T4 ligase (NEB). The reaction mixtures were incubated with 25 cycles of 37° C. for 3 min followed by 16° C. for 4 min, then 1 cycle of 50° C. for 5 min and 80° C. for 5 min. Samples of 2-3 μl were introduced into competent cells of *E. coli* strain DH5α by standard methods. Colonies lacking the RFP were confirmed to contain the desired genetic inserts by colony PCR with the appropriate primers and verified with restriction digests. Glycerol stocks were made and stored at −80° C.

Transformation of *Saccharomyces Cerevisiae*

A rapid method was used for introduction into *S. cerevisiae* of genetic constructs based on pYES2 which did not use competent cells. A loop full of *S. cerevisiae* cells was scraped off a fresh plate and the cells resuspended in 100 μl of transformation buffer (Sigma Aldrich, Catalog No. T0809). About 1 μg of plasmid DNA with 10 μl of 10 mg/ml salmon testes DNA which had been boiled for 5 min prior to use were added to the cell suspension along with 600 μl of plate buffer (Sigma Aldrich, Catalog No. P8966) and mixed well. The mixture was incubated at room temperature in a rotor wheel at the lowest speed for 16 hours. The mixture was then heat shocked for 15 min at 42° C., spun at 3500 rpm for 3 min, and the pellet of cells resuspended in 200 μl of sterile water. Aliquots of up to 100 μl were plated out onto synthetic drop-out selection media lacking uracil (SD-URA, Sigma Aldrich, Catalog No. Y1501) for selection of transformants. The plates were incubated at 28° C. for 3 days or until colonies appeared. Two or more colonies were picked from each plate and tested for the presence of the genetic construct by colony PCR to identify transformants.

Transformation of *Y. lipolytica* for Integration of Expression Cassettes

DNA of genetic constructs which included the expression cassettes (transcription units) for insertion into *Y. lipolytica* by homologous recombination was digested with NotI to release the expression cassette. The linearised DNA was introduced into competent cells of *Y. lipolytica* strain JM23, prepared using the Frozen-EZ Yeast Transformation II kit (Zymo Research, California, USA). Briefly, 5 μl (2 ug) of the NotI digested and linearised expression vector was mixed with 50 μl competent cells and 500 μl of EZ3 solution from the kit and mixed thoroughly. A negative control transformation included competent cells without any DNA of the genetic construct. The mixtures were incubated at 28° C. for two hours and then 100 μl spread on a SD-Ura plate. The plates were incubated for two days at 28° C. As the host strain JM23 was an auxotroph lacking a functional URA3 gene, only transformants having received the vector with the URA gene grew on these plates. Many colonies were observed in the *Y. lipolytica* transformations. Ura+ colonies were picked from the selection plates and confirmed as transformed by colony PCR for the introduced vector.

Growth of *S. cerevisiae* and *Y. lipolytica* Cultures for Analysis of Lipid Contents Small-scale cultures of transgenic and control *S. cerevisiae* cells were grown from glycerol stocks in 5 ml of SD-Ura medium containing 2% raffinose (w/v) (MP Chemicals, USA, Catalog No. 4010022) overnight at 28° C. with shaking for aeration. The cells were inoculated as a suspension into 10 ml of SD-Ura medium containing 2% (w/v) raffinose and 1% tergitol (v/v) (NP-40; Sigma Aldrich Catalog No. NP40S) medium to an optical density at 600 nm (OD600) of 0.1 in a 50 ml tube or a 250 ml flask and grown in a shaker incubator at 28° C. at 200 rpm for aeration. The OD600 was checked at time intervals of 15 or 30 min. When the OD600 reached 0.3, exogenous compounds as potential substrates (if any) were added along with 2% galactose for induction of the transgene from the GAL1 promoter.

Larger scale cultures of *S. cerevisiae* cells at a volume of 3 L were grown for transformants such as INVSc1::pAT003 or pYES2. These were inoculated from glycerol stocks. Starter cultures were grown in 10 ml SD-Ura medum containing 2% (w/v) raffinose for two overnights. The cells were transferred into 3 L of SD-Ura medium containing 2% (w/v) raffinose and 1% tergitol (NP-40) to an OD600 of 0.1 and grown at 28° C. with shaking at 200 rpm. The OD600 was checked at time intervals of 15 and 30 min. When the OD600 reached 0.3, galactose was added to a final concentration of 2% (w/v) to induce the transgene. When desired, sodium butyrate was added to cultures to a final concentration of 2 mg/ml. The flasks were then closed loosely with sterile aluminium foil. The cultures were grown in the incubator for 48 hours before harvesting the cells by centrifugation.

Cultures of transgenic and control *Y. lipolytica* strains were grown from glycerol stocks in 10 ml YPD medium, which contained 10 g Yeast Extract (Sigma Aldrich, Catalog No. Y1625), 20 g Peptone (Sigma Aldrich, Catalog No. P0556) and 20 g Dextrose (sigma Aldrich, Catalog No. G7021) per litre, for 48 hours. The cultures were used to inoculate 250 ml conical flasks containing 50 ml of the defined cell culture medium containing 1.7 g/l yeast nitrogen base lacking amino acids and ammonium sulfate, 80 g/l glucose and 2.2 g/l ammonium sulfate (Qiao et al., 2015). When desired, additional compounds as potential carbon sources such as oils were added at 48 hours.

When compounds were added as potential carbon sources (feeding assays), the following compounds were obtained from Sigma Aldrich: butyric acid (Catalog No. B103500), sodium butyrate (Catalog No. B5887), tributyrin (Catalog No. W222305) or palmitic acid (Catalog No. 76119). Butyric acid dissolved in water was provided to *S. cerevisiae* to a final concentration of up to 2 mg/ml. When provided to *Y. lipolytica* cultures, butyric acid (Sigma Aldrich, Catalog No. B103500) was prepared in 50% glycerol and added to the cultures to a final concentration of 2 mg/ml.

Oil preparations were also provided to some *Y. lipolytica* cultures: castor oil (Aussie Soap Supplies, AU, Catalog No. SKU: CB100), tributyrin (Sigma Aldrich, Catalog No. W222305) and long chain polyunsaturated fatty acids (GreenOMEGA 3 Capsules, Green nutritionals, AU). These oils were emulsified in 70% NP40 and added to the medium at a final concentration of 2 mg/ml. In this case the NP40 final concentration was 7% (v/v).

Cell Harvesting, Washing and Freeze Drying

When a fatty acid such as butyrate or palmitate was added to the growth medium, cells were harvested by centrifugation in 50 ml tubes at 3500 rpm for 5 min. Cell pellets were washed successively with 1 ml of 1% tergitol (v/v), 1 ml of 0.5% tergitol and a final wash with 1 ml water to remove any remaining compound from the exterior of the cells. During the final wash, pellets were transferred to pre-weighed 2 ml Eppendorf tubes and freeze-dried before weighing and lipid extraction.

When an oil was added to the growth medium, cells were harvested by centrifugation as above but cell pellets were washed successively with 5 ml of 10% tergitol (v/v), 5 ml of 5% tergitol, 5 ml of 1% tergitol, 5 ml of 0.5% tergitol and a final wash with 5 ml water to remove any remaining oil from the exterior of the cells. In some cases, microscopic observation after staining with Bodipy confirmed the absence of oil stained at the cell walls. With the final wash, pellets were transferred to pre-weighed 2 ml Eppendorf tubes and freeze-dried before weighing and lipid extraction.

Total Lipid Extraction

Total lipid was extracted from the pellet using a method modified from Bligh and Dyer, (1959) as follows. Briefly, 0.5 g of zirconium beads and 0.6 ml of chloroform:methanol (2:1 v:v) were added to the cell pellet. The cells were crushed in a bullet blender (speed 7 for 5 min). The cells were then sonicated in an ultrasonication water bath for 5 min and 0.3 ml of 0.1 M KCl in water was added. The mixture was shaken for 10 min and centrifuged for 5 min at 10,000 rpm, which separated a lower organic phase containing the lipid from the upper aqueous phase. The lower phase was transferred to a 2 ml glass vial. Additionally, 0.3 ml chloroform was added to the remaining aqueous mixture in the tube, and homogenised again in the bullet blender for 5 min. This mixture is centrifuged for 5 min and the lower organic phase collected and combined with the first extract in the same glass vial. The solvent was completely evaporated under a flow of nitrogen and the lipid dissolved in 60 µl of chloroform.

Lipid Fractionation on Thin Layer Chromatography

To separate different lipid types such as TAG, DAG, free fatty acid and polar lipids such as phospholipids (PL), total lipids were fractionated on thin layer chromatography (TLC) plates (Silica gel 60; Catalog No. 1.05626.0001, MERCK, Darmstadt, Germany) using hexane:diethylether:acetic acid (70:30:1 v:v:v) as the solvent system. The plates were then sprayed with a primuline (Sigma, Catalog No. 206865, Taufkirchen, Germany) solution prepared at a concentration of 5 mg/100 ml in acetone:water (80:20 v/v) and lipid bands visualised under UV light. Lipid standards such as Triheptadecanoin (Nuchek, USA, Catalog No. T-155) and triglyceride mix C2-C10 containing equal amounts of triacetin (TAG 6:0), tributyrin (TAG 12:0), tricaprillin (TAG 18:0) and tridecanoin (TAG 30:0) (Sigma Aldrich, Catalog No 17810-1AMP-S) were run in adjacent lanes to identify the TAG lipid spots. Lipid fractions were extracted from the silica for derivatisation using either methylation, propylation or butylation.

Lipid Derivatisation to Methyl Esters

Fatty acid methyl esters (FAME) were prepared from total extracted lipid or the purified TAG or PL fractions by treatment with 0.7 ml 1N methanolic-HCl (Sigma Aldrich, Catalog No. 90964) in a 2 ml glass vial having a PTTE-lined screw cap at 80° C. for 2 h together with a known amount of heptadecanoin (Nu-Chek PREP, Inc., Catalog No. N-7-A, Waterville, MN, USA) as an internal standard for quantification. After the vials were cooled, 0.3 ml of 0.9% NaCl (w/v) and 0.1 ml hexane were added and the mixtures vortexed for 5 minutes. The mixture was centrifuged at 1700 g for 5 min and the upper phase containing the FAME was analysed by GC.

Saponification of Triacylglycerols

Free fatty acids were released from TAG by incubating 1 mg TAG in 0.2 ml 3M KOH for 3 min at 80° C. After cooling the sample to room temperature, 100 µl hexane was added to the mixture. The mixture was vortexed for 5 min, centrifuged at 1700 g for 5 min and the upper organic phase collected for GC analysis.

Lipid Derivatisation to Ethyl Esters or Propyl Esters

To convert the fatty acids in TAG to fatty acid ethyl esters (FAEE), 2 mg of TAG was incubated in 1N HCl/ethanol solution at 80° C. for 2 h. After cooling the sample to room temperature, 100 µl hexane was added to the mixture. The mixture was vortexed for 5 min, centrifuged at 1700 g for 5 min and the upper organic phase collected for GC analysis. To convert the fatty acids in TAG to fatty acid propyl esters, 2 mg of TAG was incubated in 1N HCl/propanol rather than 1N HCl/ethanol and otherwise processed the same.

Derivatisation of Fatty Acids in TAG to Butyl Esters

TAG fractions were extracted from the silica of the TAG spots on TLC plates as follows: 0.6 ml chloroform:methanol (2:1, v/v) was added to silica scraped from the TLC plate. The mixture was shaken and centrifuged for 5 min at 10,000 g. Then, 0.3 ml of 0.1M KCl was added and the mixture shaken for 5 min. The mixture was centrifuged for 5 min at 10,000 g and the lower, organic phase collected in a 2 ml GC vial. The silica/aqueous phase was extracted a second time, this time with 0.3 ml chloroform, mixing for 10 min followed by centrifugation at 10,000 g for 5 min. The lower, organic phase was again collected and pooled into the same GC vial as the first extract. The pooled extract containing the TAG was filtered through a 0.2 μm micro-spin filter (Chromservis, EU, Catalog No. CINY-02) to remove traces of silica particles. The filtered TAG extract was then transferred into GC vial with flat insert and completely dried under a stream of nitrogen.

The purified TAG was then derivatised to butyl esters using 60 μl of butanolic:1N HCl (Sigma Aldrich, Catalog No. 87472) as described by Mannion et al., 2018, with some modifications. Valeric acid (C5:0) (Sigma Aldrich, Catalog No. 75054) was added as internal standard at an amount of 23.25 μg for SCFA and MCFA quantification and 5 μg of heptanoic acid (Nu-Chek PREP, Inc., Catalog No. N-7-A Waterville, MN, USA) as internal standard for LCFA quantification. The mixture was vortexed and heated for 2 h at 80° C. The reaction was then stopped by adding 0.03 ml of water and 0.03 ml of hexane, and thoroughly mixed for 10 min. After centrifugation at 1700 g for 5 min, the upper, organic phase was transferred into a new tube with flat insert containing 0.1 ml of saturated NaCl for a second wash to remove traces of butanol. The mixture was mixed for 5 min, centrifuged at 1700 g for 5 min and the organic phase transferred into a new GC vial with conical insert, capped quickly for GC-FID analysis as described below.

Analysis and Quantification of Methyl Esters

This method was suitable for the determination of the fatty acid composition of lipids, particularly for medium chain fatty acids (MCFA, C10-C14) and long chain fatty acids (LCFA, C16-C18) or longer chain fatty acids, including for purified TAG preparations. The method was less preferred for quantitation of SCFA due to volatility of the methyl esters of the SCFA. The lipids were derivatised to produce FAMEs as described above. The FAMEs were quantified by GC using an Agilent 7890A GC with a 30 m BPX70 column (0.25 mm inner diameter, 0.25 μm film thickness, SGE). The column temperature was programmed for 150° C. for 1 min, increasing to 210° C. at 3° C./min, holding for 2 min and reaching 240° C. at 50° C./min, then holding for 0.4 min. The injector temperature was set at 240° C. and the detector at 280° C. Helium was used as the carrier gas at a constant flow of 1.0 ml/min. FAME peaks were identified based on retention times of FAME standards (GLC-411, GLC-674; NuChek INC., USA). Peaks were integrated with Agilent Technologies ChemStation software (Rev B.04.03 (16)). The resultant data provide the fatty acid composition on a weight basis, with percentages of each fatty acid (weight %) in a total fatty acid content of 100%. These percentages on a weight basis could readily be converted to percentages on a molar basis (mol %) based on the known molecular weight of each fatty acid.

Analysis and Quantification of Butyl Esters

This method was suitable for the quantitation of short chain fatty acids (SCFA, C2-C8) as well as medium (MCFA, C10-C14) and long chain fatty acids (LCFA, C16-C18) in lipid samples, including in purified TAG preparations. It was the preferred method for quantitation of SCFA. FABEs prepared as described above were analysed on an Agilent 7890A GC using a 30 m BPX70 Column (0.25-mm inner diameter, 0.25-μm film thickness, SGE, Australia). The column temperature was set for 1 min at 40° C., followed by raising the temperature at a rate of 3° C./min to 210° C., which was held for 2 min. The column temperature was further raised to 240° C. at a rate of 100° C./min and held at this temperature for 0.5 min. Helium was used as a carrier gas at a flow rate of 1.031 ml/min. The injector temperature was programmed at 240° C. with 11.8 psi inlet pressure. The samples were injected in the split mode with a ratio of 50:1. The FID detector temperature was 280° C. with a flow of 40 ml/min hydrogen gas, 400 ml/min of air and 25 ml/min make-up gas (He). FABE peaks were identified based on retention times of FABE standard mix prepared with equal amounts of analytical grade C4-C18:1 fatty acids. Peak areas of the FABE mix were used to determine the response factors for individual FABE peaks in the GC and were applied to correct the area percentages of the FABE peaks.

In a variation of the GC method for quantitation of FABE, referred to herein as the "C8C24 method", some column parameters were adjusted. The column temperature was set for 13 min at 40° C., followed by raising the temperature at a rate of 320° C./min to 210° C., which was held for 2 min. The column temperature was further raised to 240° C. at a rate of 10° C./min and held at this temperature for 0.53 min. The injector temperature, FID detector temperature and helium flow were as before.

Peak Identity by GC-MS

To confirm the identity of fatty acid peaks, samples were run on a Gas Chromatography Mass Spectrometry (GC-MS) operating in the Electron Ionization mode at 70 eV to confirm peak identities and to identify possible extra peaks corresponding to solvents, degradation products or reagent signals. A Shimadzu GC-MS QP2010 Plus system coupled to an HTX-Pal liquid auto-sampler was used with the following parameters: 1 or 2 μl injection volume using a split/splitless inlet at a 15:1 split, at a temperature of 250° C. The oven temperature program started at 60° C. for 1 min, then increased 5° C./min to 200° C. and 10° C./min to 250° C., holding for 5 min at 250° C. MS ion source and interface temperatures were 200° C. and 250° C., respectively. Data were collected at a scan speed of 1000 and scan range from 40 to 500 m/z. Peak separation was provided by a Stabilwax® (Restek) capillary column (30 m×0.25 mm i.d., 0.25 μm film thickness) using He as a carrier gas at 30 cm/sec. Mass spectra correlations were performed using a NIST library and matching retention time of authentic SCFA standards. Identified SCFA was set to be present when SN ratio were above 10:1. Instrument blanks and procedural blanks were run for quality control purposes.

Short chain fatty acids (SCFA) in the form of methyl esters which were relatively volatile were also identified using a Head Space Solid Phase Micro Extraction (HS-SPME) technique coupled with GC-MS. Short chain FAME content in the headspace of methylated lipid extracts or methylated TLC fractions were analysed with a HTX-Pal autosampler using a DVB/CAR/PDMS fibre (Supelco, USA) and a heater agitator set at 30° C. The autosampler program was set for a headspace extraction time of 60 min under agitation using 10 ml headspace vials. The fibre containing the analytes was desorbed in a splitless inlet during 3 min with injector temperature of 250° C. VFA methyl esters were analysed with a Stabilwax® (Restek) capillary column (30 m×0.25 mm i.d., 0.25 μm film thickness) with a temperature program starting at 45° C. for 5.5 min, increasing 3° C./min to 170° C. and 7° C./min to 250° C., holding for 2 min at 250° C. MS ion source and interface temperatures were 200° C. and 270° C., respectively. Helium was the carrier gas at a linear velocity of 30 cm/sec at the initial ramping program. Data were collected at a scan speed of 1000 and scan range from 35 to 350 m/z. Spectral library matching, retention indices and VFA methyl esters standards were used for identification.

Peak Identity by LC-MS Method

Lipid extracts were reconstituted in 80 µl of methanol (MeOH):isopropanol (IPA) (1:1, v/v) and filtered through a 0.2 µm micro-spin filter (Chromservis, EU, Catalog No. CINY-02) following the supplier's instructions. For untargeted lipid identification experiments, a Q-Exactive Orbitrap mass spectrometer (Thermo Fisher, CA, USA) was used equipped with a heated electrospray ionization (HESI) probe. Separation of lipid extracts was achieved using a UPLC Vanquish System with a Zorbax Eclipse Plus C18 2.1 mm×50 mm, 1.8 µm RRHD column coupled to a UPLC guard-column. The column compartment was set at a temperature of 40° C. The binary solvent system consisted of mobile phase A (60:40 v/v acetonitrile/water and mobile phase B containing 90:10 v/v IPA/acetonitrile, both A and B containing 10 mM ammonium acetate and 0.1% formic acid. The samples were eluted with a linear gradient ranging from 40% B to 100% B over 40 min and returned to initial gradient for re-equilibration. The flow rate was 200 µl/min and the injection volume was 1 µl. Samples were kept at 10° C. in the autosampler tray. The data were acquired in positive ionization mode with full scan data dependent MS/MS acquisition at ranges of m/z 200 to 1000. The full scan and fragment spectra were collected at a resolution of 70000 and 17500, respectively. The ion source parameters were as follow: spray voltage of 3.8 kV, vaporizer 350° C., ion transfer tube of 320° C., s-Lens RF level 50%, sheath gas 35, Auxiliary gas 5 and sweep gas of 1. Data analysis and lipid identification were performed using the Freestyle Software (Thermo Fisher, CA). TAG Lipids were identified using the information of retention time and characteristic product ions, with MS1 mass error<5 ppm.

Gene Expression Analysis

Expression of transgenes was analysed using a DNase RQ1 kit (Promega Catalog No. M6101) and a Qiagen column (Qiagen RNAse-free DNAse) to purify RNA from the cells, and oligo dT primer (200-500 ng), dNTPs (10 mM), Superscript III reverse transcriptase and 0.1 M DTT for reverse transcription using standard methods.

Example 2. Expression of Acyltransferases in Yeast Cells

Candidate Gene Identification

Triacylglycerols (TAG) in the milkfat of ruminant mammals contains short chain fatty acids (SCFA), including C4:0 and C6:0, which are esterified mostly at the sn-3 position of the TAG molecules. The TAG molecules are synthesized de novo in the mammary gland of ruminant mammals by the glycerol phosphate pathway where the acyl groups of the SCFA are incorporated at the sn-3 position by specific DGAT enzymes (Marshall and Knudsen 1979). For example, the C4:0 in milkfat TAG is almost entirely esterified at the sn-3 position of TAG as a result of acylation by the these DGATs (Jensen, 2002). Although Marshall and Knudsen (1979) identified DGAT enzymes as responsible for incorporating the SCFA, the genes encoding these DGATs were not cloned, and there were multiple DGAT sequences in mammalian genomes which might be responsible for production of these TAG molecules. Therefore, the present inventors identified a variety of DGAT amino acid sequences from mammalian sources, including goat, sheep, cow and water buffalo, for testing as candidate DGATs (see SEQ ID NOs: 1, 3, 5, 7, 9, 11, 13, 15, 17, 19, 21, 23, 25, 27 or 29).

Another of the selected enzymes was the *Euonymus alatus* 1,2-diacyl-sn-glycerol:acetyl-CoA acetyltransferase (EaDAcT). The EaDAcT enzyme transfers acetyl groups from acetyl-CoA to DAG to produce TAG, resulting in an acetyl group at the sn-3 position of the TAG molecule. DAcT enzymes are members of the MBOAT family of acyltransferases that include DGAT enzymes. Bansal and Durrett (2016) described the substrate specificity of the EaDAcT, which was shown to have a strong substrate preference for transferring acetyl groups but could also transfer butyryl (C4:0) and hexanoyl (C6:0) groups but not C8 groups. The EaDAcT enzyme was encoded by the genetic construct pAT001, SEQ ID NO:2 (see below).

Production of Genetic Constructs and Introduction into *S. cerevisiae*

The genetic constructs pAT001-020 were designed and made by inserting protein coding regions into the yeast plasmid vector pYES2. The inserted nucleotide sequences encoded the candidate DGAT enzymes for testing, see the even-numbered SEQ ID NOs between SEQ ID NOs:1-30 which provide the inserted nucleotide sequences of the coding regions, and the odd-numbered SEQ ID NOs between SEQ ID NOs:1-30 which provide the amino acid sequences of the enzymes. The pYES2 vector contained a 2µ replicon for autonomous replication in yeast cells and a URA selectable marker gene to enable selection of transformants in a URA⁻ genetic background. Each construct contained a gene encoding a single DGAT enzyme, or the EaDAcT protein in the case of pAT001, for expression of the fatty acid acyltransferase gene in *S. cerevisiae*. Yeast *S. cerevisiae* strain INVSc1 was transformed with pAT001-014 and pAT019 constructs, selecting for URA⁺ cells on SD-Ura medium. Cultures (10 ml, 50 ml or 3 L) of the transformed cells were grown as described in Example 1. Cultures were grown either in the presence or absence of added butyric acid (final concentration 2 mg/ml) for the 10 ml cultures or sodium butyrate (2 mg/ml) for the 50 ml cultures as a potential carbon source. Cells produced with the exogenous substrate are referred to herein as "fed C4:0 cells", cells produced in the absence of butyrate are referred to as "non-fed cells". *S. cerevisiae* cells transformed with the pYES2 vector lacking acyltransferase genes were grown under the same conditions, with or without butyrate, as control cultures. All of the cultures received 2% (w/v) galactose during active growth phase, as inducer of transcription of the candidate acyltransferase genes from the GAL1 promoter.

TAG Content of Transformed Cells

To calculate the TAG content of cells, TAG was purified from the extracted lipid preparations, which had been extracted from measured weights of dry cellular biomass. Samples of each TAG fraction were mixed with a known amount of triheptadecanoin as an internal standard and the fatty acids in each mixture were converted to FAME as described in Example 1. The FAME were quantitiated by GC-FID. On the basis of the weight of internal standard used and the peak area observed for heptadecanoyl-FAME in the GC analysis, the weight of each individual FAME in the TAG was calculated. When the contents of all FAME of the TAG were summed, this provided the amount of total TAG in the cells on a dry weight basis. The control pYES2 cells were grown under the same conditions and analysed in the same way for comparison.

Expression of the genes encoding the candidate DGAT enzymes in the transformed cell cultures resulted in an increase in total TAG content, an increase of up to 3.3% on a weight basis compared to the empty vector control, a 2.6-fold increase (INVSC1::pYES2) (FIG. 1). This represented an increase of up to about 160% on a relative basis compared to the control cells lacking the genetic construct expressing DGAT when grown under the same conditions. Additionally, further increases in TAG content were observed with addition of butyrate to the growth medium for the cells fed with C4:0. It was concluded that expression of a DGAT enzyme was able to increase the TAG content of the cells even without the addition of the exogenous butyrate, and that the combination of the addition of butyrate with expression of the DGAT enzymes was able to further increase the TAG content of the cells.

Fatty Acid Composition of TAG Produced in *S. cerevisiae* Transformed with DGAT Genes Experiments were carried out to assay the biochemical activity of the selected DGAT enzymes in the *S. cerevisiae* transformants containing pAT001-pAT014 and pAT019. As mentioned above, the growth medium either included or lacked 2 mg/ml butyrate as an added compound, as an additional carbon source and as a potential substrate for TAG synthesis. Initial cultures were of 10 ml; later cultures were of 50 ml volume. Total lipid was extracted from the cells and the TAG and PL fractions isolated by TLC, as described in Example 1, and the fatty acid composition determined for each transformed strain. TAG and PL were derivatised to FAME and analysed by GC-FID and SPME-GCMS. Initial experiments used conversion of the fatty acids esterified in TAG to methyl esters (FAME). Later experiments used conversion to propyl esters (FAPE) or butyryl esters (FABE) due to the volatility of the FAME of SCFA, particularly of C4:0 methyl ester. In one experiment, FAME were analysed through SPME-GCMS as described in Example 1, which provided confirmation of the presence and molecular identity of C4:0, C6:0 and C8:0 in the TAG from the extracted lipid.

Data from an analysis using conversion to FAME is shown in Table 3. The presence of at least one of C4:0, C6:0 and C8:0 fatty acids was confirmed in the TAG fraction of extracted lipid from cells transformed with pAT001-pAT014 and pAT019, even though the levels were low. The identity of these fatty acids was confirmed by GC-MS. C4:0 and C6:0 were not detected in the TAG produced by *S. cerevisiae* (control) cells transformed with the pYES2 vector, and C8:0 was only detected in the C4:0 fed pYES2-transformed cells (Table 3). The presence of C4:0 in TAG was most clearly demonstrated for the cultures fed with butyrate. It was also observed that in some instances the cells transformed with the DGAT constructs exhibited slightly increased levels of the MCFAs C10:0 and C12:0 and the LCFAs C14:0 and C16:0 in the TAG. It was concluded from these data that the introduced DGAT enzymes were able to incorporate SCFA, particularly of C4:0, into the TAG produced by the *S. cerevisiae* cells. Addition of butyrate to the growth medium tended to increase the incorporation.

Fatty Acid Composition of PL Produced in *S. cerevisiae*

The lipid extracted from the cells had been fractionated by TLC to purify the TAG molecules. That fractionation also provided a purified phospholipid (PL) fraction, which was therefore analysed for its fatty acid composition. The data showed that the PL fractions obtained from pYES2 (control) and DGAT-transformed cells had similar fatty acid composition, no significant differences were observed.

Presence of TAG (28:0) in the Extracted Lipid

Milkfat has been reported to contain TAG molecules of relatively low molecular weight, including TAG 28:0, i.e. the three acyl chains summed to 28:0 (Gresti et al., 1993). There are at least seven reported isomers in TAG 28:0 including C14-C10-C4, C16-C8-C4, C18-C6-C4, C12-C10-C6, C14-C8-C6 and C16-C6-C6 (Liu et al., 2017).

The TAG preparations purified from the lipid extracted from the yeast INVSc1::pAT003 cells grown in the presence or absence of butyrate were analysed by LC-MS. TAG 28:0 was observed to be present in both samples, at peak RT=16.24-16.37; molecular mass 544.4517. In contrast, TAG 28:0 was not detected in TAG preparations from the INVSc1::pYES2 transformed cells. The LC-MS analysis therefore confirmed the production of TAG 28:0 species in the transformed cells having the DGAT genetic constructs. This provided further evidence that SCFA, specifically C4:0 and/or C6:0, was incorporated in the TAG in the transformed yeast cells containing pAT003.

TABLE 3

Fatty acid composition of TAG produced in *S. cerevisiae* transformed with candidate DGATs, using the FAME method.

| Plasmid in *S. cerevisiae* | C4:0 added ? | C4:0 | C6:0 | C8:0 | C10:0 | C12:0 | C12:1n-9 | C14:0 | C14:1n-5 | C16:0 | C16:1n-7 | C18:0 | C18:1d9 | C18:1d11 |
|---|---|---|---|---|---|---|---|---|---|---|---|---|---|---|
| pYES2 | − | 0.0 | 0.0 | 0.0 | 0.16 | 0.43 | 0.05 | 1.16 | 0.29 | 20.4 | 43.0 | 7.20 | 25.6 | 1.7 |
| (control) | + | 0.0 | 0.0 | 0.05 | 0.27 | 0.63 | 0.21 | 0.75 | 0.43 | 10.0 | 46.7 | 8.33 | 30.1 | 2.4 |
| pAT002 - | − | 0.00 | 0.08 | 0.14 | 0.62 | 0.75 | 0.00 | 2.17 | 0.53 | 22.5 | 45.4 | 5.33 | 22.5 | 0.0 |
| ChDGAT1-X1 | + | 0.14 | 0.00 | 0.12 | 0.60 | 0.66 | 0.19 | 1.13 | 0.22 | 16.6 | 38.7 | 11.6 | 28.3 | 1.7 |
| pAT003 - | − | 0.01 | 0.01 | 0.04 | 0.24 | 0.39 | 0.02 | 1.57 | 0.25 | 22.7 | 40.6 | 7.06 | 25.7 | 1.4 |
| ChDGAT1-X2 | + | 0.15 | 0.01 | 0.04 | 0.14 | 0.20 | 0.23 | 0.39 | 0.24 | 12.0 | 40.9 | 10.1 | 32.7 | 2.9 |
| pAT004 - | − | 0.04 | 0.02 | 0.07 | 0.45 | 0.68 | 0.03 | 2.30 | 0.44 | 22.4 | 40.8 | 6.68 | 24.6 | 1.5 |
| OaDGAT1-X1 | + | 0.12 | 0.00 | 0.06 | 0.35 | 0.53 | 0.24 | 1.11 | 0.25 | 15.5 | 37.6 | 11.3 | 31.4 | 1.6 |
| pAT005 - | − | 0.00 | 0.01 | 0.00 | 0.06 | 0.15 | 0.02 | 0.43 | 0.10 | 15.5 | 49.9 | 5.42 | 26.0 | 2.4 |
| OaDGAT1-X2 | + | 0.23 | 0.00 | 0.00 | 0.11 | 0.39 | 0.52 | 0.28 | 0.00 | 8.9 | 49.0 | 6.77 | 31.7 | 2.2 |
| pAT006 - | − | 0.00 | 0.04 | 0.00 | 0.32 | 0.74 | 0.14 | 1.26 | 0.42 | 18.3 | 51.7 | 5.52 | 21.7 | 0.0 |
| BtDGAT1-X1 | + | 0.00 | 0.00 | 0.00 | 0.20 | 0.69 | 0.30 | 0.54 | 0.39 | 6.8 | 52.3 | 6.20 | 30.2 | 2.4 |
| pAT007 - | − | 0.00 | 0.03 | 0.02 | 0.36 | 0.70 | 0.07 | 1.35 | 0.37 | 18.5 | 47.7 | 6.16 | 23.0 | 1.7 |
| BtDGAT1-X2 | + | 0.25 | 0.00 | 0.10 | 0.29 | 0.79 | 0.39 | 0.64 | 0.34 | 9.4 | 47.0 | 8.98 | 29.8 | 2.1 |
| pAT008 - | − | 0.26 | 0.02 | 0.08 | 0.76 | 0.99 | 0.11 | 2.73 | 0.48 | 25.8 | 43.3 | 5.73 | 18.9 | 0.9 |
| BbDGAT1-X1 | + | 0.19 | 0.05 | 0.11 | 0.56 | 1.20 | 1.00 | 2.29 | 0.34 | 28.1 | 35.8 | 8.97 | 20.7 | 0.7 |

TABLE 3-continued

Fatty acid composition of TAG produced in *S. cerevisiae* transformed with candidate DGATs, using the FAME method.

| Plasmid in *S. cerevisiae* | C4:0 added ? | C4:0 | C6:0 | C8:0 | C10:0 | C12:0 | C12:1n-9 | C14:0 | C14:1n-5 | C16:0 | C16:1n-7 | C18:0 | C18:1d9 | C18:1d11 |
|---|---|---|---|---|---|---|---|---|---|---|---|---|---|---|
| | | | | | | | Fatty acid composition of TAG (mg fatty acid/100 mg TAG) g | | | | | | | |
| pAT009 - | – | 0.00 | 0.00 | 0.02 | 0.3 | 0.7 | 0.0 | 1.6 | 0.4 | 22.5 | 43.0 | 8.2 | 21.3 | 1.3 |
| BbDGAT1-X2 | + | 0.12 | 0.00 | 0.04 | 0.16 | 0.46 | 0.46 | 0.50 | 0.24 | 7.8 | 45.7 | 8.29 | 33.8 | 2.4 |
| pAT010 - | – | 0.01 | 0.02 | 0.07 | 0.44 | 0.63 | 0.03 | 1.90 | 0.37 | 22.0 | 41.0 | 6.61 | 25.7 | 1.2 |
| BbDGAT1-X3 | + | 0.04 | 0.01 | 0.05 | 0.32 | 0.49 | 0.24 | 0.90 | 0.24 | 13.5 | 39.3 | 10.9 | 32.2 | 1.8 |
| pAT011 - | – | 0.00 | 0.01 | 0.02 | 0.22 | 0.54 | 0.04 | 1.43 | 0.37 | 21.8 | 41.3 | 7.33 | 25.7 | 1.3 |
| BbDGAT1-X4 | + | 0.15 | 0.00 | 0.03 | 0.18 | 0.43 | 0.31 | 0.44 | 0.30 | 7.1 | 48.1 | 7.57 | 32.6 | 2.8 |
| pAT012 - | – | 0.01 | 0.01 | 0.01 | 0.08 | 0.23 | 0.03 | 0.69 | 0.15 | 18.5 | 42.3 | 5.99 | 30.2 | 1.9 |
| BtDGAT1-X5 | + | 0.07 | 0.00 | 0.00 | 0.04 | 0.19 | 0.25 | 0.24 | 0.22 | 5.1 | 39.7 | 7.57 | 44.6 | 2.0 |
| pAT013 - | – | 0.00 | 0.00 | 0.03 | 0.4 | 0.8 | 0.0 | 2.2 | 0.4 | 23.9 | 40.4 | 8.9 | 21.0 | 1.1 |
| BbDGAT1-X6 | + | 0.24 | 0.00 | 0.03 | 0.22 | 0.62 | 0.58 | 0.62 | 0.37 | 8.5 | 47.6 | 8.46 | 30.5 | 2.3 |
| pAT014 - | – | 0.00 | 0.35 | 0.00 | 0.00 | 1.41 | 0.00 | 2.40 | 0.00 | 23.1 | 50.2 | 0.00 | 22.5 | 0.0 |
| BbDGAT1-X7 | + | 0.09 | 0.00 | 0.02 | 0.10 | 0.26 | 0.24 | 0.30 | 0.16 | 5.96 | 44.5 | 8.41 | 36.8 | 3.2 |
| pAT019 - | – | 0.00 | 0.03 | 0.14 | 1.1 | 1.8 | 0.0 | 5.5 | 1.0 | 25.5 | 39.4 | 6.9 | 17.2 | 0.7 |
| BtDGAT11ac | + | 0.13 | 0.02 | 0.09 | 0.53 | 0.64 | 0.12 | 1.15 | 0.25 | 16.4 | 37.8 | 11.9 | 29.4 | 1.6 |

Larger Scale Culture of Yeast Cells Producing TAG Comprising C4:0

The transformed yeast strain INVSc1::pAT003 encoding the goat enzyme ChDGAT1-X2 was selected for further testing. The transformed cells were grown in a 3 L culture in the presence of 2 mg/ml sodium butyrate as described in Example 1, or in the absence of added sodium butyrate. The control yeast strain INVSc1::pYES2 was also grown with and without sodium butyrate under the same conditions, to determine the effect of the ChDGAT1-X2 enzyme. The cells were harvested and freeze-dried, providing about 2 g of dried cell weight from the 3 L culture, and total lipid extracted. TAG was isolated from the total lipid by fractionation by TLC as described in Example 1. The amount of purified TAG isolated from the 3 L culture of the INVSc1::pAT003 cells was 32 mg, for the culture with added butyrate, and 9 mg for the INVSc1::pYES2 culture, also with added butyrate.

Samples having small amounts of the extracted lipid were also chromatographed on TLC plates to better resolve different TAG types. Two new lipid bands were observed on the plates after primuline staining for the lipid from INVSc1::pAT003 cells grown in the presence of butyrate relative to INVSc1::pYES2 grown in the presence of butyrate. These were lipid types that were produced in the INVSc1::pAT003 cells but not in the INVSc1::pYES2 cells, so clearly the result of DGAT activity. Both new bands migrated on the TLC plate with slower mobility than the more intense band having most of the TAG from each of the cultures; the new bands were clearly resolved from the main TAG band. The two new bands migrated at about the same mobility as a C2-C10 TAG control lipid (Sigma Aldrich, Catalog No 17810-1AMP-S) which contained a triglyceride mix of triacetin, tributyrin, tricaprillin and tridecanoin, applied to an adjacent lane on the TLC plate, indicating that the new bands contained species of TAG with lower molecular weight than most of of TAG molecules in the lipid. One of those two bands also appeared in the TAG from INVSc1::pAT003 grown in the absence of added butyrate, so was the result of activity of the ChDGAT1-X2 enzyme on endogenous fatty acid substrates in the yeast cells. It was concluded that the other, new band was the result of the activity of the ChDGAT1-X2 enzyme using the added butyrate, probably together with endogenous fatty acid substrates.

This experiment demonstrated the production of a new type of TAG in the DGAT-transformed yeast cells fed with butyrate.

Fatty Acid Composition of TAG Extracted from Transformed *S. cerevisiae* Cells by FAME The fatty acid composition of the purified TAG from the 3 L cultures was analysed by methylation of the fatty acids to FAME and GC-FID. TAG preparations from the INVSc1::pYES2 cells where butyrate had been added and from a milkfat sample were also analysed in parallel using the same treatment through methylation and GC-FID. The data are presented in Table 4. It was noted that the TAG from the pAT003-transformed yeast cells fed butyrate contained the SCFA C4:0 and C6:0 and increased amounts of C8:0 fatty acid, whereas the TAG from INVSc1::pYES2 lacked C4:0 and C6:0 fatty acids. The TAG from INVSc1::pAT003 also contained increased amounts of the MCFA C10:0, C12:0 and C14:0 relative to the TAG from INVSc1:pYES2, indicating that at least some of the butyrate from the medium was being elongated in the transformed yeast cells before incorporation into TAG. It was concluded that expression of the ChDGAT1-X2 enzyme in yeast was able to produce significant amounts of TAG having at least one SCFA esterified to the glycerol backbone. Furthermore, the levels of C4:0, C6:0, C8:0 and C10:0 in the TAG from the transformed yeast cells was similar to the levels of these fatty acids in the TAG of the milkfat (Table 4). The milkfat TAG had much greater amounts of C14:0 than the yeast cell TAG, but both had large amounts of C16:0, with greater than 30% (mol %) in each sample. The amount of C16:1n-7 fatty acid (palmitoleic acid) was very different in the TAG preparations from the yeast cells and milkfat—about 36% in the TAG from INVSc1::pAT001 compared to about 2% in milkfat. The level of C16:1n-7 in the INVSc1::pYES2 was even higher at about 49%, and the level of C18:1 was also much increased in the TAG from INVSc1:pYES2 while the level of C16:0 at 11.2% was much lower than in TAG from INVSc1:pAT003 at 30.92%.

The identities of the FAME molecules observed by GC-FID were also confirmed by GC-MS (Table 5).

The TAG content of the INVSc1::pAT003 at 1.6% was increased significantly compared to that in INVSc1::pYES2 at 0.5%, each figure being on a dry cell weight (DCW) basis.

TABLE 4

| | | | | | | |
|---|---|---|---|---|---|---|
| Fatty acid composition of TAG extracted from *S. cerevisiae* INVSc1::pAT003 cells, FAME method | | | | | | |
| Sample | C4:0 | C6:0 | C8:0 | C10:0 | C12:0 | C14:0 |
| INVSc1::pYES2 | 0.0 | 0.0 | 0.1 | 0.6 | 0.8 | 0.4 |
| INVSc1::pAT003 | 0.8 | 0.51 | 1.13 | 4.99 | 2.0 | 1.48 |
| Milkfat | 0.62 | 1.69 | 1.00 | 4.85 | 5.79 | 16.6 |

| Sample | C16:0 | C16:1n-7 | C18:0 | C18:1 | C18:1d11 | % TAG |
|---|---|---|---|---|---|---|
| INVSc1::pYES2 | 11.2 | 48.8 | 7.7 | 26.1 | 4.4 | 0.5 |
| INVSc1::pAT003 | 30.9 | 36.4 | 7.88 | 12.1 | 1.92 | 1.6 |
| Milkfat | 38.0 | 1.96 | 11.3 | 15.7 | 0.87 | — |

Fatty Acid Composition by Butylation

Purified TAG from the 3 L yeast cultures fed with butyrate was also analysed for fatty acid composition using a method including butylation of the fatty acids to butyl esters (FABE) rather than methylation of the fatty acids, as described in Example 1. Briefly, TAG was purified from total lipid by TLC and extracted from the silica of the TAG spots using 600 μl chloroform/methanol (2:1 v/v), shaking the mixture for 10 min and then centrifuging the mixture. 300 μl of 0.1M KCl in water was added. The mixture was shaken for 5 min and centrifuged to separate the phases. The lower, non-polar phase containing the TAG was collected. The remaining silica/aqueous mixture was extracted a second time with 300 μl chloroform and the non-polar phases combined. The extract was spun through a filter to remove any silica particles and dried down in a GC vial with flat insert. For butylation, 60 μl of butanol-1M HCl, prepared by mixing 10 ml of 3N HCl with 20 ml of dried butanol, was added along with 5 μl of a known quantity of pentanoic acid standard (C5:0, ~23.25 μg), mixed, and heated at 80° C. for 2 h. After cooling, 30 μl of water and 30 μl of hexane were added, the mixture shaken for 5 min and spun to separate the phases. The top, organic phase was collected into a GC vial, minimising evaporation, and aliquots injected into the GC-FID for fatty acid analysis. The FABE were quantitated on the Agilent 7890A GC as described in Example 1. FABE were also quantitated using the C8C24 method as described in Example 1.

TABLE 5

| | | | | | | |
|---|---|---|---|---|---|---|
| Confirmation of fatty acid identities using GC-MS (FAME method) for the INVSc1::pYes, INVSc1::pAT003 and milkfat TAG preparations. "Yes" indicates detection of corresponding FAME; nd indicates no detection. RT = retention time (min). C5:0 and C17:0 were internal standards added for quantitation. | | | | | | |
| Fatty Acid Methyl Ester | RT (min) | m/z | Blank | pYes2 | pAT003 | milkfat |
| C4:0 | 4.4 | 43, 74, 71 | nd | nd | Yes | Yes |
| C5:0 | 5.6 | 74, 85, 57 | Yes | Yes | Yes | Yes |
| C6:0 | 6.5 | 74, 43, 87 | nd | nd | Yes | Yes |
| C8:0 | 8.1 | 74, 87, 43 | nd | Yes | Yes | Yes |
| C10:0 | 9.3 | 74, 87, 43 | nd | Yes | Yes | Yes |
| C12:0 | 10.5 | 74, 87, 43 | nd | Yes | Yes | Yes |
| C12:1d9 | — | 74, 55, 87 | nd | nd | Yes | nd |
| C14:0 | 12.2 | 74, 87, 43 | nd | Yes | Yes | Yes |
| C14:1d9 | 12.8 | 55, 74, 69 | nd | Yes | Yes | Yes |
| C16:0 | 15.0 | 74, 87, 43 | nd | Yes | Yes | Yes |
| C16:1d9 | 15.9 | 55, 69, 74 | nd | Yes | Yes | Yes |
| C17:0 | 17.2 | 74, 87, 43 | Yes | Yes | Yes | Yes |
| C18:0 | 20.2 | 74, 87, 43 | nd | Yes | Yes | Yes |

TABLE 5-continued

| | | | | | |
|---|---|---|---|---|---|
| Confirmation of fatty acid identities using GC-MS (FAME method) for the INVSc1::pYes, INVSc1::pAT003 and milkfat TAG preparations. "Yes" indicates detection of corresponding FAME; nd indicates no detection. RT = retention time (min). C5:0 and C17:0 were internal standards added for quantitation. | | | | | |
| Fatty Acid Methyl Ester | RT (min) | m/z | Blank | pYes2 | pAT003 | milkfat |
| C18:1d9 | 21.5 | 55, 69, 83 | nd | Yes | Yes | Yes |
| C18:1d11 | 21.5 | 55, 69, 83 | nd | Yes | Yes | Yes |

The fatty acid composition data (Table 6) showed that the transgenic yeast cells containing pAT003 produced 4-5% (weight %) of C4:0 in its TAG, considerably higher than the milkfat at about 2.3% (weight %). C6:0 and C8:0 were also present in the TAG of the transformed yeast cells. The saturated LCFA content (C16:0+C18:0) of the TAG produced by the transformed yeast cells at about 36% (weight %) was significantly lower than the content in the milkfat at about 52-58% (weight %). The saturated MCFA content (C10:0+C12:0+C14:0) was also significantly lower in the TAG of the yeast cells compared to the milkfat, so overall providing a reduced saturated fat content in the yeast-produced TAG of about 54% on a weight basis instead of about 82-88% in the milkfat. Since saturated fats, particularly saturated LCFA, are considered less healthy to human consumers than monounsaturated and polyunsaturated fats, the inventors concluded that the yeast-generated TAG would be healthier for consumption on a weight basis than animal fat such as milkfat. Additionally, the yeast-generated TAG comprised substantially greater levels of the monounsaturated fatty acid C16:1 (palmitoleic acid), also considered a relatively healthy fatty acid, than the milkfat.

Positional Distribution of the SCFA in TAG from Transgenic Yeast Cells.

The positional distribution of fatty acids in the TAG isolated from the 3 L cultures of yeast INVSc1::pAT003 cells grown in the presence of butyrate was analysed using the *Rhizopus* lipase assay as described in Example 1, except with conversion of the fatty acids in the isolated MAG by propylation to propyl esters (FAPE). The method thereby included the conversion of sn-2 MAG into FAPE and analysis by GC-FID. The data are shown in Table 7, on either a weight basis or on a mol % basis. The data showed that the C4:0 and C6:0 present in the TAG was almost entirely at the sn-1/3 position of the TAG molecules—the sn-1 and sn-3 positions of TAG are chemically indistinct with regard to the lipase activity even though they are biochemically distinguished during synthesis of TAG. Since the C4:0 and C6:0 were present in the TAG only as a consequence of DGAT activity from the introduced ChD-GAT1-X2 gene, this implied that almost all (>95%) of the C4:0 and C6:0 were esterified at the sn-3 position of the TAG produced in the yeast cells. The C8:0 fatty acid was also predominantly at the sn-1/3 position of TAG, again implied to be present at the sn-3 position due to the DGAT activity. Each of the saturated fatty acids C14:0 and the LCFA C16:0 and C18:0 were also predominantly at the sn-1/3 positions. This was most marked for C16:0 (palmitic acid): 39.16% of the fatty acids at the sn-1/3 positions of TAG were palmitate, whereas only 2.68% of the fatty acids at the sn-2 position of TAG molecules was palmitate. In contrast, C10:0 and C12:0 fatty acids were esterified mostly at the sn-2 position of TAG. Furthermore, the monounsaturated fatty acids C14:1, C16:1, C18:1Δ9 and C18:1Δ11 were all predominantly at the sn-2 position of TAG. Therefore many of these observed preferences at the sn-1/3 and sn-2 positions for the different fatty acids were similar to that observed for the milkfat TAG (Table 7). The inventors concluded that, with regard to the positional distribution of various fatty acids, the yeast-produced TAG had similar characteristics to milkfat TAG.

The positional distribution analysis is repeated using butylation rather than propylation in the *Rhizopus* lipase assay.

TABLE 6

| Fatty acid composition of TAG fractions - butylation method | | | | | | | | | | | | |
|---|---|---|---|---|---|---|---|---|---|---|---|---|
| Weight % | Sample | C4:0 | C6:0 | C8:0 | C10:0 | C12:0 | C14:0 | C14:1 | C16:0 | C16:1 | C18:0 | C18:1 |
| Milk fat | Milkfat (standard method) | 2.30 | 1.55 | 2.08 | 4.05 | 5.19 | 15.6 | 1.58 | 43.1 | 2.32 | 14.5 | 7.76 |
| 14.0 | Milk (C8C24 method) | 1.20 | 1.44 | 2.30 | 4.31 | 5.10 | 15.7 | 1.22 | 44.9 | 2.33 | 7.53 | 14.0 |
| Yeast | pAT003 | 4.32 | 0.91 | 2.66 | 5.64 | 1.84 | 1.19 | 0.20 | 31.2 | 39.7 | 5.16 | 7.17 |
|  | pAT003 | 5.05 | 0.72 | 2.72 | 5.19 | 1.81 | 1.51 | 0.22 | 30.4 | 38.0 | 7.21 | 7.22 |
| mol % | Sample | C4:0 | C6:0 | C8:0 | C10:0 | C12:0 | C14:0 | C14:1 | C16:0 | C16:1 | C18:0 | C18:1 |
| Milk fat | Milkfat (standard method) | 5.45 | 2.87 | 3.18 | 5.26 | 5.87 | 15.6 | 1.60 | 38.6 | 2.09 | 13.2 | 6.29 |
|  | Milkfat (C8C24 method) | 2.91 | 2.84 | 3.60 | 5.72 | 5.89 | 16.0 | 1.26 | 41.1 | 2.15 | 7.05 | 11.6 |
| Yeast | pAT003 | 10.1 | 1.67 | 4.03 | 6.82 | 1.93 | 1.11 | 0.19 | 26.0 | 33.3 | 4.40 | 5.42 |
|  | pAT003 | 11.7 | 1.31 | 4.08 | 6.63 | 2.01 | 1.48 | 0.22 | 26.7 | 33.7 | 6.48 | 5.75 |

TABLE 7

| Positional distribution of fatty acids in TAG from *S. cerevisiae* transformed with INVSc1::pAT003 - propylation method | | | | | | | | |
|---|---|---|---|---|---|---|---|---|
| Weight % | Sample | C4:0 | C6:0 | C8:0 | C10:0 | C10:1 | C12:0 | C12:1d9 |
| Yeast | pAT003 TAG (total) | 0.54 | 0.18 | 1.25 | 4.22 | 0.55 | 1.74 | 0.14 |
|  | Sn-2 MAG | 0.02 | 0.01 | 0.14 | 7.51 | 0.67 | 3.53 | 0.23 |
|  | Sn-1/3 | 0.80 | 0.26 | 1.80 | 2.57 | 0.50 | 0.85 | 0.10 |

| Weight % | C14:0 | C14:1d9 | C16:0 | C16:1d9 | C18:0 | C18:1d9 | C18:1d11 |
|---|---|---|---|---|---|---|---|
| Yeast | 1.23 | 0.27 | 27.9 | 35.8 | 9.66 | 7.17 |  |
|  | 0.42 | 0.40 | 0.00 | 2.74 | 48.22 | 0.47 | 32.10 |
|  | 1.63 | 0.20 | 0.09 | 40.52 | 29.59 | 14.26 | 5.38 |

| mol % | Sample | C4:0 | C6:0 | C8:0 | C10:0 | C10:1 | C12:0 | C12:1d9 |
|---|---|---|---|---|---|---|---|---|
| Yeast | pAT003 TAG (total) | 1.52 | 0.38 | 2.16 | 6.09 | 0.81 | 2.16 | 0.18 |
|  | Sn-2 MAG | 0.04 | 0.03 | 0.25 | 10.9 | 0.80 | 4.42 | 0.29 |
|  | Sn-1/3 | 2.25 | 0.56 | 3.10 | 3.70 | 0.81 | 1.05 | 0.12 |

| mol % | C14:0 | C14:1d9 | C16:0 | C16:1d9 | C18:0 | C18:1d9 | C18:1d11 |
|---|---|---|---|---|---|---|---|
| Yeast | 1.34 | 0.20 | 27.1 | 35.0 | 8.45 | 12.6 | 1.88 |
|  | 0.47 | 0.44 | 2.68 | 47.56 | 0.42 | 28.52 | 3.14 |
|  | 1.77 | 0.22 | 39.16 | 28.79 | 12.42 | 4.71 | 1.26 |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The present application claims priority from AU 2020900780 filed 13 Mar. 2020, the entire contents of which are incorporated herein by reference.

REFERENCES

Bansal and Durrett (2016). Biosci. Rep. 36/art:e00406/doi 10.1042/BSR20160277.

Becker et al. (1991) Methods in Enzymology 194: 182-7.

Bligh and Dyer (1959) Can. J. Biochem. Physiol. 37:911-918.

Boeke et al. (1984) Mol. Gen. Genet 197: 345-47.

Celinska et al. (2017). Microb Biotechnol 10:450-455.

Gamez et al. (2003) Food Res International 36: 721-727.

Gietz et al. (1992) Nuc Acids Res. 27: 69-74.

Gresti et al. (1993) J. Dairy Sci., 76:1850-1869.

Harayama (1998). Trends Biotechnol. 16: 76-82.

Ito et al. (1983) J. Bacteriol. 153: 163-8.

Jensen (2002) J. Dairy Sci. 85:295-350.

Kawai et al. (2010) Bioeng. Bugs 1:395-406.

Kooistra et al. (2004) Yeast 21: 781-792.

Larroude et al. (2018) Biotechnol Adv. 36:2150-2164.

Liu et al. (2017) Metabolites, 7:24.

Mannion et al. (2018) J. Agric. Food Chem. 2019, 67, 499-506.

Marshall and Knudsen (1979) Eur. J. Biochem. 94, 93-98.

Mansson (2008) Food & Nutrition Research DOI: 10.3402/fnr.v52i0.1821.

Marangoni et al. (1995) Trends in Food Sci. Technol. 6: 329-335.

Needleman and Wunsch (1970) J. Mol. Biol. 48:443-453.

Orr-Weaver et al. (1981) PNAS USA 78: 6354-58.

Patel et al. (2018) Molecules 23:1562; doi:10.3390/molecules23071562.

Qiao et al. (2015) Metab Eng. 29:56-65.

Speranza et al. (2012) Process Biochemistry.

The invention claimed is:

1. Extracted microbial lipid comprising triacylglycerol (TAG) molecules, each TAG molecule having a fatty acid esterified at each of an sn-1 position, an sn-2 position and an sn-3 position, wherein at least some of the TAG molecules comprise a short chain fatty acid (SCFA) esterified at the sn-3 position of the TAG molecule, such that at least 1% by weight or by mol %, or both, of the total fatty acid content of the extracted lipid is SCFA, and wherein the esterified SCFAs at the sn-3 position of the TAG molecules comprise a) C4:0, or b) C4:0 and C6:0, wherein the extracted lipid is extracted from a microbial cell comprising one or more exogenous polynucleotide(s) encoding a fatty acid acyl-transferase or more than one fatty acid acyltransferase, wherein at least one acyltransferase has activity on SCFA-CoA molecules as a substrate, and wherein each exogenous polynucleotide is operably linked to one or more promoters that are capable of directing expression of said polynucleotide in the cells.

2. The lipid of claim 1, which is characterised by one or more or all of:

(i) the extracted lipid comprises TAG molecules which comprise a SCFA esterified at their sn-2 position, wherein the ratio of the number of TAG molecules which comprise a SCFA esterified at the sn-2 position to the number of TAG molecules which comprise a SCFA esterified at their sn-3 position (SCFA ratio sn-2:sn-3) in the extracted lipid is less than 0.50, less than 0.30, less than 0.20, less than 0.10, less than 0.05, less than 0.04, less than 0.03 or less than 0.02, (ii) the extracted lipid comprises TAG molecules which comprise C4:0 esterified at their sn-2 position, wherein the ratio of the number of TAG molecules which comprise C4:0 esterified at the sn-2 position to the number of TAG molecules which comprise C4:0 esteri-fied at their sn-3 position (sn-2:sn-3 ratio for C4:0) in the extracted lipid is less than 0.50, less than 0.30, less than 0.20, less than 0.10, less than 0.05, less than 0.04, less than 0.03 or less than 0.02, (iii) the extracted lipid comprises TAG molecules which comprise C6:0 esterified at their sn-2 position, wherein the ratio of the number of TAG molecules which comprise C6:0 esterified at the sn-2 position to the number of TAG molecules which comprise C6:0 esteri-fied at their sn-3 position (sn-2:sn-3 ratio for C6:0) in the extracted lipid is less than 0.50, less than 0.30, less than 0.20, less than 0.10, less than 0.05, less than 0.04, less than 0.03 or less than 0.02, (iv) the sn-2:sn-3 ratio for SCFA is more than 0.005, more than 0.01, between 0.005 and 0.10, between 0.01 and 0.10, between 0.005 and 0.05 or between 0.01 and 0.05, (v) the sn-2:sn-3 ratio for C4:0 is more than 0.005, more than 0.01, between 0.005 and 0.10, between 0.01 and 0.10, between 0.005 and 0.05 or between 0.01 and 0.05, (vi) the sn-2:sn-3 ratio for C6:0 is more than 0.005, more than 0.01, between 0.005 and 0.10, between 0.01 and 0.10, between 0.005 and 0.05 or between 0.01 and 0.05, (vii) the SCFA comprises C4:0 and the SCFA ratio sn-2: sn-3 is more than 0.01 or more than 0.02, (viii) more of the TAG molecules in the extracted lipid have only one SCFA esterified to the TAG molecule than two SCFA esterified to the TAG molecule, (ix) at least 1% by weight or by mol %, or both, of the total fatty acid content of the extracted lipid is C4:0, or the sum of C4:0 and C6:0, (x) at least 10%, at least 15%, at least 20%, at least 25% or at least 30% by weight of the total fatty acid content of the extracted lipid is C16:1, and (xi) the TAG molecules of the extracted lipid comprise more C16:1 esterified at the sn-2 position than any other fatty acid esterified at the sn-2 position.

3. A composition comprising the lipid of claim 1.

4. A food, feedstuff or beverage comprising the extracted lipid of claim 1, and at least one other food, feed or beverage ingredient.

5. The food, feedstuff or beverage of claim 4 which has no components derived from an animal.

6. The food, feedstuff or beverage of claim 4, which is a dairy substitute.

7. The extracted lipid according to claim 1, wherein at least one acyltransferase has activity on at least butyryl-CoA as a substrate or at least butyryl-CoA and caproyl-CoA as substrates.

8. The extracted lipid according to claim 2, wherein at least 10%, at least 15%, at least 20%, at least 25% or at least 30% by weight of the total fatty acid content of the extracted lipid is C16:1, to a maximum of 50%.

9. The extracted lipid according to claim 2, wherein the TAG molecules of the extracted lipid comprise more C16:1 esterified at the sn-2 position than any other fatty acid esterified at the sn-2 position, and wherein at least 30% or at least 40% of the fatty acids esterified at the sn-2 position of TAG are C16:1.

* * * * *

SEQUENCE LISTING

<160> NUMBER OF SEQ ID NOS: 30

<210> SEQ ID NO 1
<211> LENGTH: 363
<212> TYPE: PRT
<213> ORGANISM: Euonymus alatus

<400> SEQUENCE: 1

```
Met Met Asp Ala His Gln Glu Ile Lys Asn Phe Ile Lys Val Trp Val
1               5                   10                  15

Gln Ala Met Val Cys Leu Ser Tyr Ala Tyr Tyr Phe Ser Ser Arg Leu
            20                  25                  30

Pro Lys Gly Leu Leu Arg Leu Leu Ser Leu Leu Pro Val Leu Tyr Leu
        35                  40                  45

Leu Leu Ile Ala Pro Leu Asn Ile Ser Ser Phe Ile Leu Ser Ser Ile
    50                  55                  60

Thr Gly Phe Phe Leu Ala Trp Leu Thr Thr Phe Lys Val Ile Ser Phe
65                  70                  75                  80

Ala Phe Asp Gln Gly Pro Leu Tyr Pro Leu Pro Gln Asn Leu Leu His
            85                  90                  95

Phe Ile Ser Ile Ala Cys Leu Pro Ile Thr Ile Lys Arg Asn Pro Ser
            100                 105                 110

Pro Lys Leu Lys Ser Thr Thr Asn Pro Ser Pro Ile Ser His Leu Leu
        115                 120                 125

Lys Lys Ala Phe Met Ser Phe Pro Ser Lys Val Leu Phe His Trp Val
    130                 135                 140

Ile Ala His Leu Tyr Gln Tyr Lys Lys Tyr Met Asp Pro Asn Val Val
145                 150                 155                 160

Leu Val Ile Tyr Cys Cys His Val Tyr Val Met Leu Asp Ile Ser Leu
            165                 170                 175

Ser Leu Cys Ala Thr Leu Ala Glu Phe Leu Cys Gly Phe Asp Val Glu
        180                 185                 190
```

```
Pro Gln Phe Lys Glu Pro Tyr Leu Ala Thr Ser Leu Gln Asp Phe Trp
        195                 200                 205

Gly Arg Arg Trp Asn Ile Ile Val Ser Ser Val Leu Arg Ser Thr Val
    210                 215                 220

Tyr Ala Pro Thr Arg Asn Ile Ala Ser Tyr Leu Ile Gly Ser Arg Trp
225                 230                 235                 240

Ala Tyr Phe Pro Ala Ile Ile Ala Thr Phe Val Val Ser Gly Val Met
                245                 250                 255

His Asp Val Val Tyr Tyr Val Tyr Met Met His Met Tyr Pro Lys Trp
                260                 265                 270

Asp Met Thr Gly His Phe Val Leu His Gly Ile Cys Glu Ala Leu Glu
        275                 280                 285

Val Glu Met Lys Cys Lys Arg Ser Arg Ser Asp Lys Trp Arg Arg His
    290                 295                 300

Pro Ala Val Asp Trp Val Met Val Met Gly Phe Val Met Gly Thr Ser
305                 310                 315                 320

Val Ser Leu Leu Phe Val Pro Leu Leu Arg Asp Asn Val Asp Gln Ile
                325                 330                 335

Val Ala Glu Glu Tyr Ser Ile Leu Phe Asn Phe Val Arg Glu Lys Ile
        340                 345                 350

Val Met Leu Gly Thr Arg Phe Val Cys Gly Asn
        355                 360
```

```
<210> SEQ ID NO 2
<211> LENGTH: 1092
<212> TYPE: DNA
<213> ORGANISM: Artificial Sequence
<220> FEATURE:
<223> OTHER INFORMATION: Nucleotide sequence of the protein coding
      region of Euonymus alatus 1,2-diacyl-sn-glycerol:acetyl-CoA
      acetyltransferase (EaDAcT) in pAT001, codon optimised for
      expression in yeast.

<400> SEQUENCE: 2
atgatggacg cccaccaaga gatcaagaac tttattaagg tttgggttca agccatggtc      60
tgtttgtctt atgcttacta cttcagctct agattgccaa aaggtttgtt gaggttgttg     120
tctttgttgc cagtcttgta cttgttgttg attgccccat tgaacatctc gtccttcatt     180
ttgtcatcta tcaccggttt tttcttggct tggttgacta ccttcaaggt tatttctttc     240
gcttttgatc agggtccatt atacccattg ccacaaaatt tgttgcactt catttccatt     300
gcctgcttgc caattaccat taagagaaat ccatctccaa agctgaagtc tactactaat     360
ccatcaccaa tctctcactt gttgaaaaag gctttcatga gcttcccatc caaggttttg     420
tttcattggg ttattgctca cctgtaccag tacaaaaagt acatggatcc aaacgttgtc     480
ttggttatct actgttgcca tgtttacgtt atgctggaca tctctttgtc attgtgtgct     540
actttggctg aattcttgtg tggttttgat gtcgaaccac agttcaaaga accatacttg     600
gctacttcat tgcaagattt ttggggtaga cgttggaaca tcatcgtttc ttcagttttg     660
agatctaccg tttacgctcc aactagaaac attgcctctt acttgattgg ttctagatgg     720
gcttatttcc cagctattat tgctaccttt gttgtctctg tgttatgca  cgatgttgtt     780 tactacgttt acatgatgca catgtaccca aagtgggata tgactggtca tttcgtttta     840
catggtattt gcgaagcctt ggaagttgag atgaagtgta aaagatccag atctgataag     900
tggcgtagac atccagctgt tgattgggta atggttatgg gttttgttat gggtacttcc     960
```

-continued

```
gtcagcttgt tgtttgttcc attattgaga gataacgtcg atcaaatcgt tgccgaagaa    1020
tactccattt tgttcaactt cgtcagggaa aagatcgtca tgttgggtac tagatttgtt    1080
tgcggtaact aa                                                        1092

<210> SEQ ID NO 3
<211> LENGTH: 489
<212> TYPE: PRT
<213> ORGANISM: Capra hircus

<400> SEQUENCE: 3

Met Gly Asp Arg Gly Gly Ala Gly Gly Ser Arg Arg Arg Arg Thr Gly
1               5                   10                  15

Ser Arg Pro Ser Ile Gln Gly Gly Ser Arg Pro Ala Ala Ala Glu Glu
            20                  25                  30

Glu Val Arg Asp Val Gly Ala Gly Gly Asp Ala Pro Val Arg Asp Thr
        35                  40                  45

Asp Lys Asp Gly Asp Val Asp Val Gly Ser Gly His Trp Asp Leu Arg
    50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Val Met Leu Ile Leu Ser
                85                  90                  95

Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
        115                 120                 125

Pro Ala Leu Cys Leu Val Ile Val Ala Asn Ile Phe Ala Val Ala Ala
    130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175

Ala Ala Val Ala Phe Leu Leu Glu Ser Ile Thr Pro Val Gly Ser Val
            180                 185                 190

Leu Ala Leu Met Val Tyr Thr Ile Leu Phe Leu Lys Leu Phe Ser Tyr
        195                 200                 205

Arg Asp Val Asn Leu Trp Cys Arg Glu Arg Arg Ala Gly Ala Lys Ala
    210                 215                 220

Lys Ala Ala Leu Ala Gly Lys Lys Ala Asn Gly Gly Ala Ala Gln Arg
225                 230                 235                 240

Thr Val Ser Tyr Pro Asp Asn Leu Thr Tyr Arg Asp Leu Tyr Tyr Phe
                245                 250                 255

Leu Phe Ala Pro Thr Leu Cys Tyr Glu Leu Asn Phe Pro Arg Ser Pro
            260                 265                 270

Arg Ile Arg Lys Arg Phe Leu Leu Arg Arg Leu Leu Glu Met Leu Phe
        275                 280                 285

Leu Thr Gln Leu Gln Val Gly Leu Ile Gln Gln Trp Met Val Pro Ala
    290                 295                 300

Ile Gln Asn Ser Met Lys Pro Phe Lys Asp Met Asp Tyr Ser Arg Ile
305                 310                 315                 320

Val Glu Arg Leu Leu Lys Leu Ala Val Pro Asn His Leu Ile Trp Leu
                325                 330                 335

Ile Phe Phe Tyr Trp Leu Phe His Ser Cys Leu Asn Ala Val Ala Glu
            340                 345                 350
```

```
Leu Met Gln Phe Gly Asp Arg Glu Phe Tyr Arg Asp Trp Trp Asn Ser
        355                 360                 365

Glu Ser Ile Thr Tyr Phe Trp Gln Asn Trp Asn Ile Pro Val His Lys
        370                 375                 380

Trp Cys Leu Arg His Phe Tyr Lys Pro Met Leu Arg Arg Gly Ser Ser
385                 390                 395                 400

Lys Trp Ala Ala Arg Thr Gly Val Phe Leu Ala Ser Ala Phe Phe His
                405                 410                 415

Glu Tyr Leu Val Ser Ile Pro Leu Arg Met Phe Arg Leu Trp Ala Phe
                420                 425                 430

Thr Gly Met Met Ala Gln Ile Pro Leu Ala Trp Ile Val Gly Arg Phe
        435                 440                 445

Phe Arg Gly Asn Tyr Gly Asn Ala Ala Val Trp Leu Ser Leu Ile Ile
        450                 455                 460

Gly Gln Pro Val Ala Val Leu Met Tyr Val His Asp Tyr Tyr Val Leu
465                 470                 475                 480

Asn Arg Glu Ala Pro Thr Ala Gly Thr
                485
```

<210> SEQ ID NO 4
<211> LENGTH: 1470
<212> TYPE: DNA
<213> ORGANISM: Artificial Sequence
<220> FEATURE:
<223> OTHER INFORMATION: Nucleotide sequence of the protein coding
      region of Capra hircus (goat) diacylglycerol O-acyltransferase 1
      isoform X1 (ChDGAT1-X1) in pAT002, codon optimised for expression
      in yeast.

<400> SEQUENCE: 4

```
atgggtgata gaggtggtgc tggtggttct agaagaagaa ggacaggttc tagaccatct      60
attcaaggtg gttcaagacc agctgctgct gaagaagagg ttagagatgt tggtgccggt     120
ggtgatgctc cagttagaga tactgataag gatggtgatg ttgatgttgg ttctggtcat     180
tgggatttga gatgtcatag attgcaggac agcttgttct cttctgattc tggttttttct    240 aactacaggg gtattttgaa ctggtgcgtt gttatgttga ttttgtctaa cgctaggctg     300
ttcttggaga acttgattaa gtacggtatc ttggttgatc caatccaggt tgtttctttg     360
ttcttgaagg atccatattc ttggccagct ttgtgtttgg ttatcgttgc taacattttt     420
gctgttgctg ccttccaagt cgaaaaaaga ttggctgttg gtgctttgac tgaacaagca     480
ggtttgttgt tgcatggtgt taacttggct accattttgt gttttccagc tgcagttgct     540
ttcttgttgg aatctattac tccagtcggt tctgttttgg ctttgatggt ttacactatc     600
ctgttcctaa agctgttctc ctacagagat gttaatttgt ggtgtagaga aagacgtgct     660
ggtgctaaag ctaaagctgc tttggctggt aaaaaagcta atggtggtgc agctcaaaga     720
actgtttctt acccagataa cttgacttac agggacttgt actactttt gttcgctcca      780 actttgtgct acgaattgaa ttttccaaga agcccaagga tcagaaagag gttttttgttg    840 agaaggttgt tggagatgtt gttttttgacc caattgcaag tcggtttgat ccaacaatgg     900
atggttccag ctattcagaa ttctatgaag ccattcaagg acatggacta ctctagaatc      960
gtcgaaagat tattgaagtt ggccgttcca aaccatttga tctggttgat ttttttctac     1020
tggctgttcc actcttgctt gaatgctgtt gcagaattga tgcaatttgg tgacagagaa    1080
ttttacagag actggtggaa ctctgaatcc attacttact tttggcagaa ctggaacatc     1140
```

-continued ccagttcata agtggtgttt gagacatttc tacaagccaa tgttgcgtag aggttcttct    1200
aaatgggctg ctagaactgg tgtttttttg gcttctgctt tcttccacga atacttggtt    1260
tctatcccat tgagaatgtt cagattgtgg gctttactg gtatgatggc tcaaattcca    1320
ttggcatgga tagttggtag attcttcaga ggtaattacg gtaatgctgc tgtttggttg    1380
tccttgatta ttggtcaacc agttgctgtt ttgatgtacg ttcatgatta ctacgtcttg    1440
aacagagaag ctccaactgc tggtacttaa                                      1470

<210> SEQ ID NO 5
<211> LENGTH: 482
<212> TYPE: PRT
<213> ORGANISM: Capra hircus

<400> SEQUENCE: 5

Met Gly Pro Leu Arg Pro Asn Leu Val Pro Gln Ala Tyr Arg Arg Leu
1               5                   10                  15

Leu Gly Leu Glu Ser Glu Ser Leu Ala Pro Gly Leu Cys Val His Ser
            20                  25                  30

Cys Ala Pro Leu Ala Ser Ala Gly Lys Leu Ser Gly Arg Leu Gly Ala
        35                  40                  45

Glu Gly Leu Leu Pro Gly Thr Pro Arg Cys His Arg Leu Gln Asp Ser
    50                  55                  60

Leu Phe Ser Ser Asp Ser Gly Phe Ser Asn Tyr Arg Gly Ile Leu Asn
65                  70                  75                  80

Trp Cys Val Val Met Leu Ile Leu Ser Asn Ala Arg Leu Phe Leu Glu
                85                  90                  95

Asn Leu Ile Lys Tyr Gly Ile Leu Val Asp Pro Ile Gln Val Val Ser
            100                 105                 110

Leu Phe Leu Lys Asp Pro Tyr Ser Trp Pro Ala Leu Cys Leu Val Ile
        115                 120                 125

Val Ala Asn Ile Phe Ala Val Ala Ala Phe Gln Val Glu Lys Arg Leu
    130                 135                 140

Ala Val Gly Ala Leu Thr Glu Gln Ala Gly Leu Leu Leu His Gly Val
145                 150                 155                 160

Asn Leu Ala Thr Ile Leu Cys Phe Pro Ala Ala Val Ala Phe Leu Leu
                165                 170                 175

Glu Ser Ile Thr Pro Val Gly Ser Val Leu Ala Leu Met Val Tyr Thr
            180                 185                 190

Ile Leu Phe Leu Lys Leu Phe Ser Tyr Arg Asp Val Asn Leu Trp Cys
        195                 200                 205

Arg Glu Arg Arg Ala Gly Ala Lys Ala Lys Ala Ala Leu Ala Gly Lys
    210                 215                 220

Lys Ala Asn Gly Gly Ala Ala Gln Arg Thr Val Ser Tyr Pro Asp Asn
225                 230                 235                 240

Leu Thr Tyr Arg Asp Leu Tyr Tyr Phe Leu Phe Ala Pro Thr Leu Cys
                245                 250                 255

Tyr Glu Leu Asn Phe Pro Arg Ser Pro Arg Ile Arg Lys Arg Phe Leu
            260                 265                 270

Leu Arg Arg Leu Leu Glu Met Leu Phe Leu Thr Gln Leu Gln Val Gly
        275                 280                 285

Leu Ile Gln Gln Trp Met Val Pro Ala Ile Gln Asn Ser Met Lys Pro
    290                 295                 300

Phe Lys Asp Met Asp Tyr Ser Arg Ile Val Glu Arg Leu Leu Lys Leu
305                 310                 315                 320

-continued

```
Ala Val Pro Asn His Leu Ile Trp Leu Ile Phe Phe Tyr Trp Leu Phe
            325             330             335

His Ser Cys Leu Asn Ala Val Ala Glu Leu Met Gln Phe Gly Asp Arg
            340             345             350

Glu Phe Tyr Arg Asp Trp Trp Asn Ser Glu Ser Ile Thr Tyr Phe Trp
            355             360             365

Gln Asn Trp Asn Ile Pro Val His Lys Trp Cys Leu Arg His Phe Tyr
    370             375             380

Lys Pro Met Leu Arg Arg Gly Ser Ser Lys Trp Ala Ala Arg Thr Gly
385             390             395             400

Val Phe Leu Ala Ser Ala Phe Phe His Glu Tyr Leu Val Ser Ile Pro
            405             410             415

Leu Arg Met Phe Arg Leu Trp Ala Phe Thr Gly Met Met Ala Gln Ile
            420             425             430

Pro Leu Ala Trp Ile Val Gly Arg Phe Phe Arg Gly Asn Tyr Gly Asn
            435             440             445

Ala Ala Val Trp Leu Ser Leu Ile Ile Gly Gln Pro Val Ala Val Leu
    450             455             460

Met Tyr Val His Asp Tyr Tyr Val Leu Asn Arg Glu Ala Pro Thr Ala
465             470             475             480

Gly Thr
```

```
<210> SEQ ID NO 6
<211> LENGTH: 1449
<212> TYPE: DNA
<213> ORGANISM: Artificial Sequence
<220> FEATURE:
<223> OTHER INFORMATION: Nucleotide sequence of the protein coding
      region of Capra hircus (goat) diacylglycerol O-acyltransferase 1
      isoform X2 (ChDGAT1-X2) in pAT003, codon optimised for expression
      in yeast.

<400> SEQUENCE: 6
atgggtcccc tgaggcctaa tttggttcca caagcctata aagattgct aggtttggaa       60 tctgaatctt tggctccagg tttgtgtgtt cattcttgtg ctccattggc ttcagctggt      120
aaattgtctg gtagattggg tgctgaaggt ttgttgccag gtactccaag atgtcataga      180
ttgcaagatt ccttgttctc ctctgattct ggtttctcta actacagagg tatttttgaac     240 tggtgcgttg tcatgttgat tttgtctaat gctaggctgt tcttggagaa cttgattaag      300
tacggtatct tggttgatcc aatccaggtt gtttctttgt tcttgaagga tccatattct      360
tggccagctt tgtgtttggt tatcgttgct aacatttttg ctgttgctgc cttccaagtc      420
gaaaaaagat tggctgttgg tgctttgact gaacaagctg gtttgttgtt gcatggtgtt      480
aacttggcta ccattttgtg ttttccagct gctgttgcat ttctgttgga atctattact      540
ccagttggtt ccgttttggc tttgatggtt tacactatcc tgttcctaaa gctgttctcc      600
tacagagatg ttaatttgtg gtgtagagaa agacgtgctg gtgctaaagc taaagctgct      660
ttggctggta aaaaagctaa tggtggtgct gctcaaagaa ctgtttctta cccagataac      720
ttgacttaca gggacttgta ctactttttg ttcgctccaa ctttgtgcta cgaattgaat      780
tttccaagaa gcccaagaat ccgtaagagg ttttttgttga aaggttgtt ggagatgttg      840 tttttgaccc aattgcaagt cggtttgatc caacaatgga tggttccagc tattcagaat      900
tctatgaagc cattcaagga catggactac tctagaatcg tcgaaagatt attgaagttg      960
gccgttccaa accatttgat ctggttgatt tttttctact ggctgttcca ctcttgcttg    1020
```

```
aatgcagttg ctgaattgat gcaatttggt gacagagaat tttacagaga ctggtggaac     1080
tccgaatcca ttacttactt ttggcaaaac tggaacatcc cagttcataa gtggtgtttg     1140
agacatttct acaagccaat gcttagaagg ggttcttcta aatgggctgc tagaactggt     1200 gttttttttgg cttctgcttt cttccacgaa tacttggttt ctatcccatt gagaatgttc    1260
agattgtggg ctttttactgg tatgatggct caaattccat tggcatggat agttggtaga    1320
ttcttcagag gtaattacgg taatgctgct gtttggttgt ccttgattat tggtcaacca     1380
gttgctgttt tgatgtacgt tcatgattac tacgtcttga acagagaagc tccaactgct     1440
ggtacttaa                                                             1449
```

<210> SEQ ID NO 7
<211> LENGTH: 489
<212> TYPE: PRT
<213> ORGANISM: Ovis aries

<400> SEQUENCE: 7

```
Met Gly Asp Arg Gly Gly Ala Gly Gly Ser Arg Arg Arg Arg Thr Gly
1               5                   10                  15

Ser Arg Pro Ser Ile Gln Gly Gly Ser Arg Pro Ala Ala Ala Glu Glu
            20                  25                  30

Glu Val Arg Asp Val Gly Ala Gly Gly Asp Ala Pro Val Arg Asp Thr
        35                  40                  45

Asp Lys Asp Gly Asp Val Asp Val Gly Ser Gly His Trp Asp Leu Arg
    50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Val Met Leu Ile Leu Ser
                85                  90                  95

Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
        115                 120                 125

Pro Ala Leu Cys Leu Val Ile Val Ala Asn Ile Phe Ala Val Ala Ala
    130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175

Ala Ala Val Ala Phe Leu Leu Glu Ser Ile Thr Pro Val Gly Ser Val
            180                 185                 190

Leu Ala Leu Met Val Tyr Thr Ile Leu Phe Leu Lys Leu Phe Ser Tyr
        195                 200                 205

Arg Asp Val Asn Leu Trp Cys Arg Glu Arg Arg Ala Gly Ala Lys Ala
    210                 215                 220

Lys Ala Ala Leu Ala Gly Lys Lys Ala Asn Gly Gly Ala Ala Gln Arg
225                 230                 235                 240

Thr Val Ser Tyr Pro Asp Asn Leu Thr Tyr Arg Asp Leu Tyr Tyr Phe
                245                 250                 255

Leu Phe Ala Pro Thr Leu Cys Tyr Glu Leu Asn Phe Pro Arg Ser Pro
            260                 265                 270

Arg Ile Arg Lys Arg Phe Leu Leu Arg Arg Leu Leu Glu Met Leu Phe
        275                 280                 285
```

```
Leu Thr Gln Leu Gln Val Gly Leu Ile Gln Gln Trp Met Val Pro Ala
    290                 295                 300

Ile Gln Asn Ser Met Lys Pro Phe Lys Asp Met Asp Tyr Ser Arg Ile
305                 310                 315                 320

Val Glu Arg Leu Leu Lys Leu Ala Val Pro Asn His Leu Ile Trp Leu
                325                 330                 335

Ile Phe Phe Tyr Trp Leu Phe His Ser Cys Leu Asn Ala Val Ala Glu
                340                 345                 350

Leu Met Gln Phe Gly Asp Arg Glu Phe Tyr Arg Asp Trp Trp Asn Ser
            355                 360                 365

Glu Ser Ile Thr Tyr Phe Trp Gln Asn Trp Asn Ile Pro Val His Lys
    370                 375                 380

Trp Cys Leu Arg His Phe Tyr Lys Pro Met Leu Arg Arg Gly Ser Ser
385                 390                 395                 400

Lys Trp Ala Ala Arg Thr Gly Val Phe Leu Ala Ser Ala Phe Phe His
                405                 410                 415

Glu Tyr Leu Val Ser Ile Pro Leu Arg Met Phe Arg Leu Trp Ala Phe
                420                 425                 430

Thr Gly Met Met Ala Gln Ile Pro Leu Ala Trp Ile Val Gly Arg Phe
            435                 440                 445

Phe Arg Gly Asn Tyr Gly Asn Ala Ala Val Trp Leu Ser Leu Ile Ile
    450                 455                 460

Gly Gln Pro Val Ala Val Leu Met Tyr Val His Asp Tyr Tyr Val Leu
465                 470                 475                 480

Asn Arg Glu Ala Pro Thr Ala Gly Thr
                485
```

<210> SEQ ID NO 8
<211> LENGTH: 1470
<212> TYPE: DNA
<213> ORGANISM: Artificial Sequence
<220> FEATURE:
<223> OTHER INFORMATION: Nucleotide sequence of the protein coding
    region of the protein coding region of Ovis aries (sheep) diacylglycerol O-acyltransferase 1
    isoform X1 (OaDGAT1-X1) in pAT004, codon optimised for expression
    in yeast.

<400> SEQUENCE: 8

```
atgggtgata gaggtggtgc tggtggttct agaagaagaa ggacaggttc tagaccatct      60
attcaaggtg gttcaagacc agctgctgct gaagaagagg ttagagatgt tggtgccggt     120
ggtgatgctc cagttagaga tactgataag gatggtgatg ttgatgttgg ttctggtcat     180
tgggatttga gatgtcatag attgcaggac agcttgttct cttctgattc tggtttttct     240
aactacaggg gtattttgaa ctggtgcgtt gttatgttga ttttgtctaa cgctaggctg     300
ttcttggaga acttgattaa gtacggtatc ttggttgatc caatccaggt tgtttctttg     360
ttcttgaagg atccatattc ttggccagct ttgtgtttgg ttatcgttgc taacattttt     420
gctgttgctg ccttccaagt cgaaaaaaga ttggctgttg gtgctttgac tgaacaagca     480
ggtttgttgt tgcatggtgt taacttggct accattttgt gttttccagc tgcagttgct     540
ttcttgttgg aatctattac tccagtcggt tctgttttgg ctttgatggt ttacactatc     600
ctgttcctaa agctgttctc ctacagagat gttaatttgt ggtgtagaga aagacgtgct     660
ggtgctaaag ctaaagctgc tttggctggt aaaaaagcta atggtggtgc agctcaaaga     720
actgtttctt acccagataa cttgacttac agggacttgg actacttttt gttcgctcca     780
actttgtgct acgaattgaa ttttccaaga agcccaagga tcagaaagag gttttttgttg     840
```

-continued

```
agaaggttgt tggagatgtt gttttttgacc caattgcaag tcggtttgat ccaacaatgg      900
atggttccag ctattcagaa ttctatgaag ccattcaagg acatggacta ctctagaatc      960
gtcgaaagat tattgaagtt ggccgttcca aaccatttga tctggttgat ttttttctac     1020
tggctgttcc actcttgctt gaatgctgtt gcagaattga tgcaatttgg tgacagagaa     1080
ttttacagag actggtggaa ctctgaatcc attacttact tttggcagaa ctggaacatc     1140
ccagttcata agtggtgttt gagacatttc tacaagccaa tgttgcgtag aggttcttct     1200
aaatgggctg ctagaactgg tgtttttttg gcttctgctt tcttccacga atacttggtt     1260
tctatcccat tgagaatgtt cagattgtgg gcttttactg gtatgatggc tcaaattcca     1320
ttggcatgga tagttggtag attcttcaga ggtaattacg gtaatgctgc tgtttggttg     1380
tccttgatta ttggtcaacc agttgctgtt ttgatgtacg ttcatgatta ctacgtcttg     1440
aacagagaag ctccaactgc tggtacttaa                                     1470
```

```
<210> SEQ ID NO 9
<211> LENGTH: 467
<212> TYPE: PRT
<213> ORGANISM: Ovis aries

<400> SEQUENCE: 9

Met Gly Asp Arg Gly Gly Ala Gly Gly Ser Arg Arg Arg Arg Thr Gly
1               5                   10                  15

Ser Arg Pro Ser Ile Gln Gly Gly Ser Arg Pro Ala Ala Ala Glu Glu
            20                  25                  30

Glu Val Arg Asp Val Gly Ala Gly Gly Asp Ala Pro Val Arg Asp Thr
        35                  40                  45

Asp Lys Asp Gly Asp Val Asp Val Gly Ser Gly His Trp Asp Leu Arg
    50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Val Met Leu Ile Leu Ser
                85                  90                  95

Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
        115                 120                 125

Pro Ala Leu Cys Leu Val Ile Val Ala Asn Ile Phe Ala Val Ala Ala
        130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175

Ala Ala Val Ala Phe Leu Leu Glu Ser Ile Thr Pro Val Gly Ser Val
            180                 185                 190

Leu Ala Leu Met Val Tyr Thr Ile Leu Phe Leu Lys Leu Phe Ser Tyr
            195                 200                 205

Arg Asp Val Asn Leu Trp Cys Arg Glu Arg Arg Ala Gly Ala Lys Ala
        210                 215                 220

Lys Ala Ala Leu Ala Asp Leu Tyr Tyr Phe Leu Phe Ala Pro Thr Leu
225                 230                 235                 240

Cys Tyr Glu Leu Asn Phe Pro Arg Ser Pro Arg Ile Arg Lys Arg Phe
                245                 250                 255
```

-continued

```
Leu Leu Arg Arg Leu Leu Glu Met Leu Phe Leu Thr Gln Leu Gln Val
        260             265                 270

Gly Leu Ile Gln Gln Trp Met Val Pro Ala Ile Gln Asn Ser Met Lys
        275             280                 285

Pro Phe Lys Asp Met Asp Tyr Ser Arg Ile Val Glu Arg Leu Leu Lys
        290             295                 300

Leu Ala Val Pro Asn His Leu Ile Trp Leu Ile Phe Phe Tyr Trp Leu
305             310                 315                 320

Phe His Ser Cys Leu Asn Ala Val Ala Glu Leu Met Gln Phe Gly Asp
                325                 330                 335

Arg Glu Phe Tyr Arg Asp Trp Trp Asn Ser Glu Ser Ile Thr Tyr Phe
            340             345                 350

Trp Gln Asn Trp Asn Ile Pro Val His Lys Trp Cys Leu Arg His Phe
            355             360                 365

Tyr Lys Pro Met Leu Arg Arg Gly Ser Ser Lys Trp Ala Ala Arg Thr
        370             375                 380

Gly Val Phe Leu Ala Ser Ala Phe Phe His Glu Tyr Leu Val Ser Ile
385             390                 395                 400

Pro Leu Arg Met Phe Arg Leu Trp Ala Phe Thr Gly Met Met Ala Gln
                405                 410                 415

Ile Pro Leu Ala Trp Ile Val Gly Arg Phe Phe Arg Gly Asn Tyr Gly
            420             425                 430

Asn Ala Ala Val Trp Leu Ser Leu Ile Ile Gly Gln Pro Val Ala Val
            435             440                 445

Leu Met Tyr Val His Asp Tyr Tyr Val Leu Asn Arg Glu Ala Pro Thr
        450             455                 460

Ala Gly Thr
465
```

```
<210> SEQ ID NO 10
<211> LENGTH: 1404
<212> TYPE: DNA
<213> ORGANISM: Artificial Sequence
<220> FEATURE:
<223> OTHER INFORMATION: Nucleotide sequence of the protein coding
      region of Ovis aries (sheep) diacylglycerol O-acyltransferase 1
      isoform X2 (OaDGAT1-X2) in pAT005, codon optimised for expression
      in yeast.

<400> SEQUENCE: 10
atgggtgata gaggtggtgc tggtggttct agaagaagaa ggacaggttc tagaccatct     60
attcaaggtg gttcaagacc agctgctgct gaagaagagg ttagagatgt tggtgccggt    120
ggtgatgctc cagttagaga tactgataag gatggtgatg ttgatgttgg ttctggtcat    180
tgggatttga gatgtcatag attgcaggac agcttgttct cttctgattc tggtttttct    240
aactacaggg gtattttgaa ctggtgcgtt gttatgttga ttttgtctaa cgctaggctg    300
ttcttggaga acttgattaa gtacggtatc ttggttgatc caatccaggt tgtttctttg    360
ttcttgaagg atccatattc ttggccagct ttgtgtttgg ttatcgttgc taacattttt    420
gctgttgctg ccttccaagt cgaaaaaaga ttggctgttg gtgctttgac tgaacaagca    480
ggtttgttgt tgcatggtgt taacttggct accattttgt gttttccagc tgcagttgct    540
ttcttgttgg aatctattac tccagtcggt tctgtttttgg ctttgatggt ttacactatc    600
ctgttcctaa agctgttctc ctacagagat gttaatttgt ggtgtagaga aagacgtgct    660
ggtgctaaag ctaaagctgc tttggctgac ttgtactact ttttgtttgc tccaaccttg    720
```

-continued

```
tgctacgaat tgaattttcc aagatctccc aggatcagaa agaggttttt gttgagaaga      780
ttgctggaaa tgctgttttt gacccaattg caagtcggtt tgattcaaca atggatggtt      840
ccagctatcc agaattctat gaagccattc aaggatatgg actactccag aatcgtcgaa      900
aggttgttga aattggcagt tccaaaccat ttgatctggc tgattttttt ctactggttg      960
ttccactctt gcttgaatgc tgttgcagaa ttgatgcaat ttggtgacag agaattttac     1020
agagactggg ggaactctga atccattact tactttggc agaactggaa catcccagtt      1080
cataagtggt gtttgagaca tttctacaag ccaatgttgc gtagaggttc ttctaaatgg      1140
gctgctagaa ctggtgtttt tttggcttct gctttcttcc acgaatactt ggtttctatc      1200
ccattgagaa tgttcagatt gtgggctttt actggtatga tggctcaaat tccattagct      1260
tggatcgttg gtagattctt cagaggtaat tatggtaatg ctgccgtttg gttgtccttg      1320
attattggtc aaccagttgc tgttttgatg tacgttcatg attactacgt cttgaacaga      1380
gaagctccaa ctgctggtac ttaa                                            1404
```

```
<210> SEQ ID NO 11
<211> LENGTH: 566
<212> TYPE: PRT
<213> ORGANISM: Bos taurus

<400> SEQUENCE: 11

Met Gly Asp Arg Gly Gly Ala Gly Gly Ser Arg Arg Arg Arg Thr Gly
1               5                   10                  15

Ser Arg Pro Ser Ile Gln Gly Gly Ser Gly Pro Ala Ala Ala Glu Glu
            20                  25                  30

Glu Val Arg Asp Val Gly Ala Gly Gly Asp Ala Pro Val Arg Asp Thr
        35                  40                  45

Asp Lys Asp Gly Asp Val Asp Val Gly Ser Gly His Trp Asp Leu Arg
    50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Val Met Leu Ile Leu Ser
                85                  90                  95

Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
        115                 120                 125

Pro Ala Leu Cys Leu Val Ile Val Ala Asn Ile Phe Ala Val Ala Ala
    130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175

Ala Ala Val Ala Phe Leu Leu Glu Ser Ile Thr Pro Val Gly Ser Val
            180                 185                 190

Leu Ala Leu Met Val Tyr Thr Ile Leu Phe Leu Lys Leu Phe Ser Tyr
        195                 200                 205

Arg Asp Val Asn Leu Trp Cys Arg Glu Arg Arg Ala Gly Ala Lys Ala
    210                 215                 220

Lys Ala Ala Leu Ala Gly Lys Ala Ala Asn Gly Gly Ala Ala Gln Arg
225                 230                 235                 240

Thr Val Ser Tyr Pro Asp Asn Leu Thr Tyr Arg Gly Glu Asp Pro Ala
                245                 250                 255
```

-continued

```
Gly Gly Trp Gly Asp Cys Pro Ala Ala Trp Pro Ala Ser Pro Ala Leu
        260             265             270

Pro Ser Arg Ser Leu Leu Leu Pro Leu Arg Pro His Pro Val Leu Arg
        275             280             285

Ala Gln Leu Pro Pro Leu Pro Pro His Pro Lys Ala Leu Pro Ala Ala
    290             295             300

Ala Thr Pro Gly Asp Ala Val Pro His Pro Ala Pro Gly Gly Ala Asp
305             310             315             320

Pro Ala Val Asp Gly Pro Gly His Pro Glu Leu His Glu Ala Leu Gln
            325             330             335

Gly His Gly Leu Leu Pro His Arg Gly Ala Pro Pro Glu Ala Gly Gly
        340             345             350

Glu Trp Pro Ala Gly Trp Gly Arg Val Gly Ala Gly Gly Ala Val Leu
        355             360             365

Ala Pro Gly Thr His Ser Pro Gln Val Pro Asn His Leu Ile Trp Leu
    370             375             380

Ile Phe Phe Tyr Trp Leu Phe His Ser Cys Leu Asn Ala Val Ala Glu
385             390             395             400

Leu Met Gln Phe Gly Asp Arg Glu Phe Tyr Arg Asp Trp Trp Trp Val
            405             410             415

Ala Leu Pro Gly Arg Gly Trp Trp Gly Pro Pro Leu Gly Leu Gly Pro
            420             425             430

Glu Pro Leu Pro Thr Leu Pro Arg Pro Arg Arg Asn Ser Glu Ser Ile
        435             440             445

Thr Tyr Phe Trp Gln Asn Trp Asn Ile Pro Val His Lys Trp Cys Ile
    450             455             460

Arg His Phe Tyr Lys Pro Met Leu Arg Arg Gly Ser Ser Lys Trp Ala
465             470             475             480

Ala Arg Thr Ala Val Phe Leu Ala Ser Ala Phe Phe His Glu Tyr Leu
            485             490             495

Val Ser Ile Pro Leu Arg Met Phe Arg Leu Trp Ala Phe Thr Gly Met
        500             505             510

Met Ala Gln Ile Pro Leu Ala Trp Ile Val Gly Arg Phe Phe Arg Gly
        515             520             525

Asn Tyr Gly Asn Ala Ala Val Trp Leu Ser Leu Ile Ile Gly Gln Pro
    530             535             540

Val Ala Val Leu Met Tyr Val His Asp Tyr Tyr Val Leu Asn Arg Glu
545             550             555             560

Ala Pro Ala Ala Gly Thr
            565
```

<210> SEQ ID NO 12
<211> LENGTH: 1701
<212> TYPE: DNA
<213> ORGANISM: Artificial Sequence
<220> FEATURE:
<223> OTHER INFORMATION: Nucleotide sequence of the protein coding
      region of Bos taurus (cattle) diacylglycerol 0-acyltransferase 1
      isoform X1 (BtDGAT1-X1) in pAT006, codon optimised for expression
      in yeast.

<400> SEQUENCE: 12
atgggtgata gaggtggtgc tggtggttct agaagaagaa ggacaggttc tagaccatct      60
attcaaggtg gttctggtcc agctgctgct gaagaagagg ttagagatgt tggtgccggt     120
ggtgatgctc cagttagaga tactgataag gatggtgatg ttgatgttgg ttcaggtcat     180

-continued

```
tgggatttga gatgtcatag attgcaggac agcttgttct cttctgattc tggttttttct      240 aactacaggg gtattttgaa ctggtgcgtt gttatgttga ttttgtctaa cgctaggctg       300
ttcttggaga acttgattaa gtacggtatc ttggttgatc caatccaggt tgtttctttg       360
ttcttgaagg atccatattc ttggccagct ttgtgtttgg ttatcgttgc taacattttt       420
gctgttgctg ccttccaagt cgaaaaaaga ttggctgttg gtgctttgac tgaacaagca       480
ggtttgttgt tgcatggtgt taacttggct accattttgt gttttccagc tgcagttgct       540
ttcttgttgg aatctattac tccagttggt tccgtttttgg ctttgatggt ttacactatc      600
ctgttcctaa agctgttctc ctacagagat gttaatttgt ggtgtagaga aagacgtgct       660
ggtgctaaag ctaaagctgc tttggctggt aaagctgcaa atggtggtgc agctcaaaga       720
actgtttctt acccagataa cttgacctac agaggtgaag atccagccgg tggttggggt       780
gattgtccag cagcttggcc tgcttctcca gctttgccat ctagatcttt gttgttacca       840
ttaagaccac atccagtttt gagagcacaa ttgccaccat tgcctccaca tccaaaggct       900
ttgcctgctg ctgctactcc aggtgatgct gttccacatc ctgctccagg tggtgccgat       960
ccagctgttg atggtccagg tcatccagaa ttgcatgaag ccttacaagg tcatggtttg      1020
ttgccacata gaggtgctcc acctgaagct ggtggtgaat ggccagcagg ttggggtaga      1080
gttggtgcag cggtgctgt ttttggctcca ggtactcatt ctccacaagt tccaaaccat       1140
ttgatctggc tgattttctt ctactggttg ttccattctt gcttgaatgc tgttgcagaa      1200
ttgatgcaat ttggtgacag agaattttac agagattggt ggtgggttgc tttgccaggt      1260
agaggatggt ggggtccacc attaggtttg ggtccagaac cattgccaac tttgccaaga      1320
ccaagaagaa actctgaatc cattacctac ttttggcaga actggaacat tcctgttcat      1380
aagtggtgca tcagacattt ctataagcca atgttgagaa ggggttcttc taaatgggct      1440
gctagaactg ctgtttttttt ggcttctgct ttcttccacg aatacttggt ttctatccca      1500
ttgagaatgt tcagattgtg ggctttttact ggtatgatgc ctcaaattcc attggcttgg      1560
atagttggta gattcttcag aggtaattac ggtaatgctg ctgtttggtt gtccttgatt      1620
attggtcaac agttgcagt tttgatgtac gttcatgatt actacgtctt gaacagagaa        1680
gctccagctg ccggtactta a                                                 1701
```

```
<210> SEQ ID NO 13
<211> LENGTH: 467
<212> TYPE: PRT
<213> ORGANISM: Bos taurus

<400> SEQUENCE: 13

Met Gly Asp Arg Gly Gly Ala Gly Gly Ser Arg Arg Arg Thr Gly
1               5                   10                  15

Ser Arg Pro Ser Ile Gln Gly Gly Ser Gly Pro Ala Ala Ala Glu Glu
            20                  25                  30

Glu Val Arg Asp Val Gly Ala Gly Gly Asp Ala Pro Val Arg Asp Thr
            35                  40                  45

Asp Lys Asp Gly Asp Val Asp Val Gly Ser Gly His Trp Asp Leu Arg
        50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Val Met Leu Ile Leu Ser
                85                  90                  95
```

```
Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
            115                 120                 125

Pro Ala Leu Cys Leu Val Ile Val Ala Asn Ile Phe Ala Val Ala Ala
            130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175

Ala Ala Val Ala Phe Leu Leu Glu Ser Ile Thr Pro Val Gly Ser Val
                180                 185                 190

Leu Ala Leu Met Val Tyr Thr Ile Leu Phe Leu Lys Leu Phe Ser Tyr
                195                 200                 205

Arg Asp Val Asn Leu Trp Cys Arg Glu Arg Arg Ala Gly Ala Lys Ala
            210                 215                 220

Lys Ala Ala Leu Ala Asp Leu Tyr Tyr Phe Leu Phe Ala Pro Thr Leu
225                 230                 235                 240

Cys Tyr Glu Leu Asn Phe Pro Arg Ser Pro Arg Ile Arg Lys Arg Phe
                245                 250                 255

Leu Leu Arg Arg Leu Leu Glu Met Leu Phe Leu Thr Gln Leu Gln Val
                260                 265                 270

Gly Leu Ile Gln Gln Trp Met Val Pro Ala Ile Gln Asn Ser Met Lys
            275                 280                 285

Pro Phe Lys Asp Met Asp Tyr Ser Arg Ile Val Glu Arg Leu Leu Lys
            290                 295                 300

Leu Ala Val Pro Asn His Leu Ile Trp Leu Ile Phe Phe Tyr Trp Leu
305                 310                 315                 320

Phe His Ser Cys Leu Asn Ala Val Ala Glu Leu Met Gln Phe Gly Asp
                325                 330                 335

Arg Glu Phe Tyr Arg Asp Trp Trp Asn Ser Glu Ser Ile Thr Tyr Phe
            340                 345                 350

Trp Gln Asn Trp Asn Ile Pro Val His Lys Trp Cys Ile Arg His Phe
            355                 360                 365

Tyr Lys Pro Met Leu Arg Arg Gly Ser Ser Lys Trp Ala Ala Arg Thr
    370                 375                 380

Ala Val Phe Leu Ala Ser Ala Phe Phe His Glu Tyr Leu Val Ser Ile
385                 390                 395                 400

Pro Leu Arg Met Phe Arg Leu Trp Ala Phe Thr Gly Met Met Ala Gln
                405                 410                 415

Ile Pro Leu Ala Trp Ile Val Gly Arg Phe Phe Arg Gly Asn Tyr Gly
                420                 425                 430

Asn Ala Ala Val Trp Leu Ser Leu Ile Ile Gly Gln Pro Val Ala Val
            435                 440                 445

Leu Met Tyr Val His Asp Tyr Tyr Val Leu Asn Arg Glu Ala Pro Ala
    450                 455                 460

Ala Gly Thr
465
```

```
<210> SEQ ID NO 14
<211> LENGTH: 1404
<212> TYPE: DNA
<213> ORGANISM: Artificial Sequence
<220> FEATURE:
<223> OTHER INFORMATION: Nucleotide sequence of the protein coding
``` region of Bos taurus (cattle) diacylglycerol O-acyltransferase 1
isoform X2 (BtDGAT1-X2) in pAT007, codon optimised for expression
in yeast.

<400> SEQUENCE: 14

```
atgggtgata gaggtggtgc tggtggttct agaagaagaa ggacaggttc tagaccatct      60
attcaaggtg gttctggtcc agctgctgct gaagaagagg ttagagatgt tggtgccggt     120
ggtgatgctc cagttagaga tactgataag gatggtgatg ttgatgttgg ttcaggtcat     180
tgggatttga gatgtcatag attgcaggac agcttgttct cttctgattc tggttttttct     240 aactacaggg gtattttgaa ctggtgcgtt gttatgttga ttttgtctaa cgctaggctg     300
ttcttggaga acttgattaa gtacggtatc ttggttgatc caatccaggt tgtttctttg     360
ttcttgaagg atccatattc ttggccagct ttgtgtttgg ttatcgttgc taacatttttt     420 gctgttgctg ccttccaagt cgaaaaaaga ttggctgttg gtgctttgac tgaacaagca     480
ggtttgttgt tgcatggtgt taacttggct accattttgt gttttccagc tgcagttgct     540
ttcttgttgg aatctattac tccagttggt tccgttttgg ctttgatggt ttacactatc     600
ctgttcctaa agctgttctc ctacagagat gttaatttgt ggtgtagaga aagacgtgct     660
ggtgctaaag ctaaagctgc ctttggctgac ttgtactact ttttgtttgc tccaaccttg     720
tgctacgaat tgaatttttcc aagatctccc aggatcagaa agaggttttt gttgagaaga     780
ttgctggaaa tgctgttttt gacccaattg caagtcggtt tgattcaaca atggatggtt     840
ccagctatcc agaattctat gaagccattc aaggatatgg actactccag aatcgtcgaa     900
aggttgttga aattggcagt tccaaaccat ttgatctggc tgattttttt ctactggttg     960
ttccactctt gcttgaatgc tgttgcagaa ttgatgcaat ttggtgacag agaatttttac    1020 agagactggt ggaactctga atccattact tactttttggc agaactggaa catcccagtt    1080
cataagtggt gtatcagaca tttctacaag ccaatgttgc gtagaggttc ttctaaatgg    1140
gctgctagaa cagcagtttt tttggcttct gctttcttcc acgaatactt ggtttctatc    1200
ccattgagaa tgttcagatt gtgggctttt actggtatga tggctcaaat tccattagct    1260
tggatcgttg gtagattctt cagaggtaat tatggtaatg ctgccgtttg gttgtccttg    1320
attattggtc aaccagttgc tgttttgatg tacgttcatg attactacgt cttgaacaga    1380
gaagctcctg ctgctggtac ttaa                                            1404
```

<210> SEQ ID NO 15
<211> LENGTH: 519
<212> TYPE: PRT
<213> ORGANISM: Bubalus bubalis

<400> SEQUENCE: 15

```
Met Cys Pro Gln Glu Gly Lys Gly Ser Pro Gly Leu Ser Pro Tyr Lys
1               5                   10                  15

Thr Gly Gly Leu Ala Gln Cys Pro Gly Trp Pro Pro Gly Gly Arg Val
            20                  25                  30

Val Gly Gly Arg Trp Gly Cys Cys Leu Glu Pro Ala Ser Gly Ala Gly
        35                  40                  45

Pro Gly Leu Ser Cys Ala Pro Pro Leu Pro Pro Ala Glu Gly Trp
    50                  55                  60

Leu Pro Ser Pro Pro Asp Pro Ala Leu Gly Ala Gly Leu Ser Glu Val
65                  70                  75                  80

Gly Ser Glu Gly Pro Leu Leu Ala Ser Ala Val Asp Ser Arg Cys His
                85                  90                  95
```

```
Arg Leu Gln Asp Ser Leu Phe Ser Ser Asp Ser Gly Phe Ser Asn Tyr
        100                 105                 110

Arg Gly Ile Leu Asn Trp Cys Val Val Met Leu Ile Leu Ser Asn Ala
        115                 120                 125

Arg Leu Phe Leu Glu Asn Leu Ile Lys Tyr Gly Ile Leu Val Asp Pro
    130                 135                 140

Ile Gln Val Val Ser Leu Phe Leu Lys Asp Pro Tyr Ser Trp Pro Ala
145                 150                 155                 160

Leu Cys Leu Val Ile Val Ala Asn Ile Phe Ala Val Ala Ala Phe Gln
                165                 170                 175

Val Glu Lys Arg Leu Ala Val Gly Ala Leu Thr Glu Gln Ala Gly Leu
            180                 185                 190

Leu Leu His Gly Val Asn Leu Ala Thr Ile Leu Cys Phe Pro Ala Ala
            195                 200                 205

Val Ala Phe Leu Leu Glu Ser Ile Thr Pro Val Gly Ser Val Leu Ala
    210                 215                 220

Leu Met Val Tyr Thr Ile Leu Phe Leu Lys Leu Phe Ser Tyr Arg Asp
225                 230                 235                 240

Val Asn Leu Trp Cys Arg Glu Arg Arg Ala Gly Ala Lys Ala Lys Ala
                245                 250                 255

Ala Leu Ala Gly Lys Lys Ala Asn Gly Gly Ala Ala Gln Arg Thr Val
            260                 265                 270

Ser Tyr Pro Asp Asn Leu Thr Tyr Arg Asp Leu Tyr Tyr Phe Leu Phe
            275                 280                 285

Ala Pro Thr Leu Cys Tyr Glu Leu Asn Phe Pro Arg Ser Pro Arg Ile
    290                 295                 300

Arg Lys Arg Phe Leu Leu Arg Arg Leu Leu Glu Met Leu Phe Leu Thr
305                 310                 315                 320

Gln Leu Gln Val Gly Leu Ile Gln Gln Trp Met Val Pro Ala Ile Gln
            325                 330                 335

Asn Ser Met Lys Pro Phe Lys Asp Met Asp Tyr Ser Arg Ile Val Glu
            340                 345                 350

Arg Leu Leu Lys Leu Ala Val Pro Asn His Leu Ile Trp Leu Ile Phe
            355                 360                 365

Phe Tyr Trp Leu Phe His Ser Cys Leu Asn Ala Val Ala Glu Leu Met
    370                 375                 380

Gln Phe Gly Asp Arg Glu Phe Tyr Arg Asp Trp Trp Asn Ser Glu Ser
385                 390                 395                 400

Ile Thr Tyr Phe Trp Gln Asn Trp Asn Ile Pro Val His Lys Trp Cys
                405                 410                 415

Ile Arg His Phe Tyr Lys Pro Met Leu Arg Arg Gly Ser Ser Lys Trp
            420                 425                 430

Ala Ala Arg Thr Ala Val Phe Leu Ala Ser Ala Phe Phe His Glu Tyr
            435                 440                 445

Leu Val Ser Ile Pro Leu Arg Met Phe Arg Leu Trp Ala Phe Thr Gly
    450                 455                 460

Met Met Ala Gln Ile Pro Leu Ala Trp Ile Val Gly Arg Phe Phe Arg
465                 470                 475                 480

Gly Asn Tyr Gly Asn Ala Ala Val Trp Leu Ser Leu Ile Ile Gly Gln
                485                 490                 495

Pro Val Ala Val Leu Met Tyr Val His Asp Tyr Tyr Val Leu Asn Arg
            500                 505                 510
```

Glu Ala Pro Ala Ala Gly Thr
        515

<210> SEQ ID NO 16
<211> LENGTH: 1560
<212> TYPE: DNA
<213> ORGANISM: Artificial Sequence
<220> FEATURE:
<223> OTHER INFORMATION: Nucleotide sequence of the protein coding
      region of Bubulus bubulis (water buffalo) diacylglycerol
      O-acyltransferase 1 isoform X1 (BbDGAT1-X1) in pAT008, codon
      optimised for expression in yeast.

<400> SEQUENCE: 16
atgtgcccac aagaaggtaa aggttctcca ggtttgtctc catacaaaac tggtggtttg       60
gctcaatgtc caggttggcc accaggtggt agagttgttg gtggtagatg gggttgttgt      120
ttggaaccag cttctggtgc tggtccaggt ttatcttgtg ctccaccacc attgccacca      180
gctgaaggtt ggttgccatc tccaccagat ccagctttag gtgccggttt gtctgaagtt      240
ggttctgaag gtcctttgtt ggcttctgct gttgattcta gatgtcacag attgcaggat      300
tccttgttct cttctgattc tggtttctct aactacaggg gtattttgaa ctggtgcgtt      360
gttatgttga ttttgtctaa cgctaggctg ttcttggaga acttgattaa gtacggtatc      420
ttggttgatc caatccaggt tgtttctttg ttcttgaagg atccatattc ttggccagct      480
ttgtgtttgt ttatcgttgc taacattttt gctgttgctg ccttccaagt cgaaaaaaga      540
ttggctgttg gtgctttgac tgaacaagct ggtttgttgt tgcatggtgt taacttggct      600
accattttgt gttttccagc tgctgttgca tttctgttgg aatctattac tccagtcggt      660
tctgttttgg ctttgatggt ttacactatc ctgttcctaa agttgttctc ctacagagat      720
gttaatttgt ggtgcagaga aagacgtgct ggtgctaaag ctaaagctgc tttggctggt      780
aaaaaagcta acggtggtgc tgctcaaaga actgtttctt atccagataa cttgacctac      840
agggacttgt actactttt gtttgctcca accttgtgct acgaattgaa ttttccaaga      900
tctcccagga tcagaaagag gtttttgttg agaagattgc tggaaatgct gtttttgacc      960
caattgcaag tcggtttgat tcaacaatgg atggttccag ctatccagaa ttctatgaag     1020
ccattcaagg atatggacta ctccagaatc gtcgaaaggt tgttgaaatt ggcagttcca     1080
aaccatttga tctggctgat ttttttctac tggttgttcc actcttgctt gaatgcagtt     1140
gctgaattga tgcaatttgg tgacagagaa ttttacagag actggtggaa ctctgaatcc     1200
attacttact tttggcagaa ctggaacatc ccagttcata agtggtgtat cagacatttc     1260
tacaagccaa tgcttagaag gggttcttct aaatgggctg ctagaacagc agttttttg      1320 gcctctgctt ttttccacga atacttggtt tctatcccat tgagaatgtt cagattgtgg     1380
gcttttactg gtatgatggc tcaaattcca ttagcttgga tcgttggtag attcttcaga     1440
ggtaattatg gtaatgctgc cgtttggttg tccttgatta ttggtcaacc agttgctgtt     1500
ttgatgtacg ttcatgatta ctacgtcttg aacagagaag ctccagctgc aggtacttaa     1560

<210> SEQ ID NO 17
<211> LENGTH: 504
<212> TYPE: PRT
<213> ORGANISM: Bubalus bubalis

<400> SEQUENCE: 17

Met Cys Pro Gln Glu Gly Lys Gly Ser Pro Gly Leu Ser Pro Tyr Lys
1               5                   10                  15

```
Thr Gly Gly Leu Ala Gln Cys Pro Gly Trp Pro Pro Gly Gly Arg Val
        20                  25                  30

Val Gly Gly Arg Trp Gly Cys Cys Leu Glu Pro Ala Ser Gly Ala Gly
        35                  40                  45

Pro Gly Leu Ser Cys Ala Pro Pro Pro Leu Pro Pro Ala Glu Gly Trp
        50                  55                  60

Leu Pro Ser Pro Pro Asp Pro Ala Leu Gly Ala Gly Leu Ser Glu Val
65                  70                  75                  80

Gly Ser Glu Gly Pro Leu Leu Ala Ser Ala Val Asp Ser Arg Cys His
                85                  90                  95

Arg Leu Gln Asp Ser Leu Phe Ser Ser Asp Ser Gly Phe Ser Asn Tyr
            100                 105                 110

Arg Gly Ile Leu Asn Trp Cys Val Val Met Leu Ile Leu Ser Asn Ala
            115                 120                 125

Arg Leu Phe Leu Glu Asn Leu Ile Lys Tyr Gly Ile Leu Val Asp Pro
        130                 135                 140

Ile Gln Val Val Ser Leu Phe Leu Lys Asp Pro Tyr Ser Trp Pro Ala
145                 150                 155                 160

Leu Cys Leu Val Ile Val Ala Asn Ile Phe Ala Val Ala Ala Phe Gln
                165                 170                 175

Val Glu Lys Arg Leu Ala Val Gly Ala Leu Thr Glu Gln Ala Gly Leu
            180                 185                 190

Leu Leu His Gly Val Asn Leu Ala Thr Ile Leu Cys Phe Pro Ala Ala
            195                 200                 205

Val Ala Phe Leu Leu Glu Ser Ile Thr Pro Val Gly Ser Val Leu Ala
        210                 215                 220

Leu Met Val Tyr Thr Ile Leu Phe Leu Lys Leu Phe Ser Tyr Arg Asp
225                 230                 235                 240

Val Asn Leu Trp Cys Arg Glu Arg Arg Ala Gly Ala Lys Ala Lys Ala
                245                 250                 255

Ala Leu Ala Gly Lys Lys Ala Asn Gly Gly Ala Ala Gln Arg Thr Val
            260                 265                 270

Ser Tyr Pro Asp Asn Leu Thr Tyr Arg Asp Leu Tyr Tyr Phe Leu Phe
        275                 280                 285

Ala Pro Thr Leu Cys Tyr Glu Leu Asn Phe Pro Arg Ser Pro Arg Ile
        290                 295                 300

Arg Lys Arg Phe Leu Leu Arg Arg Leu Leu Glu Met Leu Phe Leu Thr
305                 310                 315                 320

Gln Leu Gln Val Gly Leu Ile Gln Gln Trp Met Val Pro Ala Ile Gln
            325                 330                 335

Asn Ser Met Lys Pro Phe Lys Val Pro Asn His Leu Ile Trp Leu Ile
            340                 345                 350

Phe Phe Tyr Trp Leu Phe His Ser Cys Leu Asn Ala Val Ala Glu Leu
        355                 360                 365

Met Gln Phe Gly Asp Arg Glu Phe Tyr Arg Asp Trp Trp Asn Ser Glu
        370                 375                 380

Ser Ile Thr Tyr Phe Trp Gln Asn Trp Asn Ile Pro Val His Lys Trp
385                 390                 395                 400

Cys Ile Arg His Phe Tyr Lys Pro Met Leu Arg Arg Gly Ser Ser Lys
                405                 410                 415

Trp Ala Ala Arg Thr Ala Val Phe Leu Ala Ser Ala Phe Phe His Glu
            420                 425                 430

Tyr Leu Val Ser Ile Pro Leu Arg Met Phe Arg Leu Trp Ala Phe Thr
```

-continued

```
            435                 440                 445
Gly Met Met Ala Gln Ile Pro Leu Ala Trp Ile Val Gly Arg Phe Phe
        450                 455                 460
Arg Gly Asn Tyr Gly Asn Ala Ala Val Trp Leu Ser Leu Ile Ile Gly
465                 470                 475                 480
Gln Pro Val Ala Val Leu Met Tyr Val His Asp Tyr Tyr Val Leu Asn
                485                 490                 495
Arg Glu Ala Pro Ala Ala Gly Thr
                500
```

```
<210> SEQ ID NO 18
<211> LENGTH: 1515
<212> TYPE: DNA
<213> ORGANISM: Artificial Sequence
<220> FEATURE:
<223> OTHER INFORMATION: Nucleotide sequence of the protein coding
      region of Bubulus bubulis (water buffalo) diacylglycerol
      O-acyltransferase 1 isoform X2 (BbDGAT1-X2) in pAT009, codon
      optimised for expression in yeast.

<400> SEQUENCE: 18
atgtgcccac aagaaggtaa aggttctcca ggtttgtctc catacaaaac tggtggtttg      60
gctcaatgtc caggttggcc accaggtggt agagttgttg gtggtagatg gggttgttgt     120
ttggaaccag cttctggtgc tggtccaggt ttatcttgtg ctccaccacc attgccacca     180
gctgaaggtt ggttgccatc tccaccagat ccagctttag gtgccggttt gtctgaagtt     240
ggttctgaag gtcctttgtt ggcttctgct gttgattcta gatgtcacag attgcaggat     300
tccttgttct cttctgattc tggtttctct aactacaggg gtattttgaa ctggtgcgtt     360
gttatgttga ttttgtctaa cgctaggctg ttcttggaga acttgattaa gtacggtatc     420
ttggttgatc caatccaggt tgtttctttg ttcttgaagg atccatattc ttggccagct     480
ttgtgtttgg ttatcgttgc taacattttt gctgttgctg ccttccaagt cgaaaaaaga     540
ttggctgttg gtgctttgac tgaacaagct ggtttgttgt tgcatggtgt taacttggct     600
accattttgt gttttccagc tgctgttgca tttctgttgg aatctattac tccagtcggt     660
tctgttttgg ctttgatggt ttacactatc ctgttcctaa agttgttctc ctacagagat     720
gttaatttgt ggtgcagaga aagacgtgct ggtgctaaag ctaaagctgc tttggctggt     780
aaaaaagcta acggtggtgc tgctcaaaga actgtttctt atccagataa cttgacctac     840
agggacttgt actactttt gtttgctcca accttgtgct acgaattgaa ttttccaaga     900
tctcccagga tcagaaagag gtttttgttg agaagattgc tggaaatgct gttttttgacc     960 caattgcaag tcggttttgat tcaacaatgg atggttccag ctatccagaa ttctatgaag    1020
ccattcaagg ttcctaacca cttgatctgg ttgattttct tctactggtt gttccactct    1080
tgcttgaatg cagttgctga attgatgcaa tttggtgaca gagaaatttta cagagactgg    1140 tggaactctg aatccattac ttactttttgg cagaactgga acatcccagt tcataagtgg    1200
tgtatcagac atttctacaa gccaatgctt agaagggggtt cttctaaatg ggctgctaga    1260
acagcagttt ttttggcctc tgcttttttc cacgaatact tggtttctat cccattgaga    1320
atgttcagat gtgggctttt tactggtatg atggctcaaa ttccattagc ttggatcgtt    1380
ggtagattct tcagaggtaa ttatggtaat gctgccgttt ggttgtcctt gattattggt    1440
caaccagttg ctgtttttgat gtacgttcat gattactacg tcttgaacag agaagctcca    1500
gctgcaggta cttaa                                                       1515
```

-continued

```
<210> SEQ ID NO 19
<211> LENGTH: 499
<212> TYPE: PRT
<213> ORGANISM: Bubalus bubalis

<400> SEQUENCE: 19

Met Arg Trp Leu Trp Asp Gly Ser Ser Asp Ser Glu Trp Ala Gly Tyr
1               5                   10                  15

Gly Gly Phe Trp Ala Gly Pro Ser Ser Gly Tyr Pro His Arg Leu Ser
            20                  25                  30

Ser Trp Asp Ser Trp Ala Trp Glu Pro Cys Ser Pro Cys Gln Lys Ala
        35                  40                  45

Gly Ala Glu Ser Arg Arg Arg Gly Pro Gly Gly Ser Glu Pro His Cys
    50                  55                  60

Val Cys Ser Pro Gly Trp Thr Trp Arg Arg Cys His Arg Leu Gln Asp
65                  70                  75                  80

Ser Leu Phe Ser Ser Asp Ser Gly Phe Ser Asn Tyr Arg Gly Ile Leu
            85                  90                  95

Asn Trp Cys Val Val Met Leu Ile Leu Ser Asn Ala Arg Leu Phe Leu
            100                 105                 110

Glu Asn Leu Ile Lys Tyr Gly Ile Leu Val Asp Pro Ile Gln Val Val
            115                 120                 125

Ser Leu Phe Leu Lys Asp Pro Tyr Ser Trp Pro Ala Leu Cys Leu Val
    130                 135                 140

Ile Val Ala Asn Ile Phe Ala Val Ala Ala Phe Gln Val Glu Lys Arg
145                 150                 155                 160

Leu Ala Val Gly Ala Leu Thr Glu Gln Ala Gly Leu Leu Leu His Gly
            165                 170                 175

Val Asn Leu Ala Thr Ile Leu Cys Phe Pro Ala Ala Val Ala Phe Leu
            180                 185                 190

Leu Glu Ser Ile Thr Pro Val Gly Ser Val Leu Ala Leu Met Val Tyr
            195                 200                 205

Thr Ile Leu Phe Leu Lys Leu Phe Ser Tyr Arg Asp Val Asn Leu Trp
    210                 215                 220

Cys Arg Glu Arg Arg Ala Gly Ala Lys Ala Lys Ala Ala Leu Ala Gly
225                 230                 235                 240

Lys Lys Ala Asn Gly Gly Ala Ala Gln Arg Thr Val Ser Tyr Pro Asp
            245                 250                 255

Asn Leu Thr Tyr Arg Asp Leu Tyr Tyr Phe Leu Phe Ala Pro Thr Leu
            260                 265                 270

Cys Tyr Glu Leu Asn Phe Pro Arg Ser Pro Arg Ile Arg Lys Arg Phe
            275                 280                 285

Leu Leu Arg Arg Leu Leu Glu Met Leu Phe Leu Thr Gln Leu Gln Val
    290                 295                 300

Gly Leu Ile Gln Gln Trp Met Val Pro Ala Ile Gln Asn Ser Met Lys
305                 310                 315                 320

Pro Phe Lys Asp Met Asp Tyr Ser Arg Ile Val Glu Arg Leu Leu Lys
            325                 330                 335

Leu Ala Val Pro Asn His Leu Ile Trp Leu Ile Phe Phe Tyr Trp Leu
            340                 345                 350

Phe His Ser Cys Leu Asn Ala Val Ala Glu Leu Met Gln Phe Gly Asp
            355                 360                 365

Arg Glu Phe Tyr Arg Asp Trp Trp Asn Ser Glu Ser Ile Thr Tyr Phe
    370                 375                 380
```

Trp Gln Asn Trp Asn Ile Pro Val His Lys Trp Cys Ile Arg His Phe
385                   390               395               400

Tyr Lys Pro Met Leu Arg Arg Gly Ser Ser Lys Trp Ala Ala Arg Thr
               405             410               415

Ala Val Phe Leu Ala Ser Ala Phe Phe His Glu Tyr Leu Val Ser Ile
          420             425             430

Pro Leu Arg Met Phe Arg Leu Trp Ala Phe Thr Gly Met Met Ala Gln
        435           440             445

Ile Pro Leu Ala Trp Ile Val Gly Arg Phe Phe Arg Gly Asn Tyr Gly
     450            455             460

Asn Ala Ala Val Trp Leu Ser Leu Ile Ile Gly Gln Pro Val Ala Val
465               470             475               480

Leu Met Tyr Val His Asp Tyr Tyr Val Leu Asn Arg Glu Ala Pro Ala
          485             490             495

Ala Gly Thr

<210> SEQ ID NO 20
<211> LENGTH: 1500
<212> TYPE: DNA
<213> ORGANISM: Artificial Sequence
<220> FEATURE:
<223> OTHER INFORMATION: Nucleotide sequence of the protein coding
     region of Bubulus bubulis (water buffalo) diacylglycerol
     O-acyltransferase 1 isoform X3 (BbDGAT1-X3) in pAT010, codon
     optimised for expression in yeast.

<400> SEQUENCE: 20
atgaggtggt tgtgggatgg ttcctctgat tctgaatggg ctggttatgg tggtttttgg    60
gctggtccat cttctggtta tccacataga ttgtcatctt gggattcttg ggcttgggaa   120
ccatgttctc catgtcaaaa agctggtgct gaatctagaa gaagaggtcc aggcggttct   180
gaaccacatt gtgtttgttc tccaggttgg acttggagaa gatgtcatag attgcaagac   240
agcttgttct cttccgattc tggttttttct aactacaggg gtattttgaa ctggtgcgtt   300
gttatgttga ttttgtctaa cgctaggctg ttcttggaga acttgattaa gtacggtatc   360
ttggttgatc caatccaggt tgtttctttg ttcttgaagg atccatattc ttggccagct   420
ttgtgtttgg ttatcgttgc taacattttt gctgttgctg ccttccaagt cgaaaaaaga   480
ttggctgttg gtgctttgac tgaacaagca ggtttgttgt tgcatggtgt taacttggct   540
accattttgt gttttccagc tgctgttgca ttcttgttgg aatctattac tccagttggt   600
tccgttttgg ctttgatggt ttacactatc ctgttcctaa agctgttctc ctacagagat   660
gttaatttgt ggtgtagaga aagacgtgct ggtgctaaag ctaaagctgc tttggctggt   720
aaaaaagcta atggtggtgc tgctcaaaga actgtttctt acccagataa cttgacttac   780
agggacttgt actactttt gttcgctcca actttgtgct acgaattgaa ttttccaaga   840
tctcccagga tcagaaagag gttttgttg agaagattgc tggaaatgct gttttgacc   900 caattgcaag tcggtttgat tcaacaatgg atggtcccag ctattcagaa ttctatgaag   960 ccatcaagg acatggacta ctctagaatc gtcgaaaggt tgttgaaatt ggccgttcca  1020
aaccatttga tctggctgat tttttctac tggttgttcc actcttgctt gaatgcagtt  1080
gctgaattga tgcaatttgg tgacagagaa ttttacagag actggtggaa ctctgaatcc  1140
attacttact tttggcagaa ctggaacatc ccagttcata agtggtgtat cagacatttc  1200
tacaagccaa tgcttagaag gggttcttca aaatgggctg ctagaacagc agttttttttg  1260

-continued gcttctgctt tcttccacga atacttggtt tctatcccat tgagaatgtt cagattgtgg    1320 gctttttactg gtatgatggc tcaaattcca ttggcatgga tagttggtag attcttcaga    1380
ggtaattacg gtaatgctgc tgtttggttg tccttgatta ttggtcaacc agttgctgtt    1440
ttgatgtacg ttcatgatta ctacgtcttg aacagagaag ctccagctgc aggtacttaa    1500

<210> SEQ ID NO 21
<211> LENGTH: 497
<212> TYPE: PRT
<213> ORGANISM: Bubalus bubalis

<400> SEQUENCE: 21

Met Cys Pro Gln Glu Gly Lys Gly Ser Pro Gly Leu Ser Pro Tyr Lys
1               5                   10                  15

Thr Gly Gly Leu Ala Gln Cys Pro Gly Trp Pro Pro Gly Gly Arg Val
                20                  25                  30

Val Gly Gly Arg Trp Gly Cys Cys Leu Glu Pro Ala Ser Gly Ala Gly
            35                  40                  45

Pro Gly Leu Ser Cys Ala Pro Pro Leu Pro Pro Ala Glu Gly Trp
        50                  55                  60

Leu Pro Ser Pro Pro Asp Pro Ala Leu Gly Ala Gly Leu Ser Glu Val
65                  70                  75                  80

Gly Ser Glu Gly Pro Leu Leu Ala Ser Ala Val Asp Ser Arg Cys His
                85                  90                  95

Arg Leu Gln Asp Ser Leu Phe Ser Ser Asp Ser Gly Phe Ser Asn Tyr
                100                 105                 110

Arg Gly Ile Leu Asn Trp Cys Val Val Met Leu Ile Leu Ser Asn Ala
            115                 120                 125

Arg Leu Phe Leu Glu Asn Leu Ile Lys Tyr Gly Ile Leu Val Asp Pro
        130                 135                 140

Ile Gln Val Val Ser Leu Phe Leu Lys Asp Pro Tyr Ser Trp Pro Ala
145                 150                 155                 160

Leu Cys Leu Val Ile Val Ala Asn Ile Phe Ala Val Ala Ala Phe Gln
            165                 170                 175

Val Glu Lys Arg Leu Ala Val Gly Ala Leu Thr Glu Gln Ala Gly Leu
            180                 185                 190

Leu Leu His Gly Val Asn Leu Ala Thr Ile Leu Cys Phe Pro Ala Ala
            195                 200                 205

Val Ala Phe Leu Leu Glu Ser Ile Thr Pro Val Gly Ser Val Leu Ala
        210                 215                 220

Leu Met Val Tyr Thr Ile Leu Phe Leu Lys Leu Phe Ser Tyr Arg Asp
225                 230                 235                 240

Val Asn Leu Trp Cys Arg Glu Arg Arg Ala Gly Ala Lys Ala Lys Ala
            245                 250                 255

Ala Leu Ala Asp Leu Tyr Tyr Phe Leu Phe Ala Pro Thr Leu Cys Tyr
            260                 265                 270

Glu Leu Asn Phe Pro Arg Ser Pro Arg Ile Arg Lys Arg Phe Leu Leu
        275                 280                 285

Arg Arg Leu Leu Glu Met Leu Phe Leu Thr Gln Leu Gln Val Gly Leu
        290                 295                 300

Ile Gln Gln Trp Met Val Pro Ala Ile Gln Asn Ser Met Lys Pro Phe
305                 310                 315                 320

Lys Asp Met Asp Tyr Ser Arg Ile Val Glu Arg Leu Leu Lys Leu Ala
                325                 330                 335

-continued

```
Val Pro Asn His Leu Ile Trp Leu Ile Phe Phe Tyr Trp Leu Phe His
            340             345                 350

Ser Cys Leu Asn Ala Val Ala Glu Leu Met Gln Phe Gly Asp Arg Glu
            355             360                 365

Phe Tyr Arg Asp Trp Trp Asn Ser Glu Ser Ile Thr Tyr Phe Trp Gln
            370             375                 380

Asn Trp Asn Ile Pro Val His Lys Trp Cys Ile Arg His Phe Tyr Lys
385                 390                 395                 400

Pro Met Leu Arg Arg Gly Ser Ser Lys Trp Ala Ala Arg Thr Ala Val
                405                 410                 415

Phe Leu Ala Ser Ala Phe Phe His Glu Tyr Leu Val Ser Ile Pro Leu
            420                 425                 430

Arg Met Phe Arg Leu Trp Ala Phe Thr Gly Met Met Ala Gln Ile Pro
            435                 440                 445

Leu Ala Trp Ile Val Gly Arg Phe Phe Arg Gly Asn Tyr Gly Asn Ala
            450                 455                 460

Ala Val Trp Leu Ser Leu Ile Ile Gly Gln Pro Val Ala Val Leu Met
465                 470                 475                 480

Tyr Val His Asp Tyr Tyr Val Leu Asn Arg Glu Ala Pro Ala Ala Gly
                485                 490                 495

Thr
```

<210> SEQ ID NO 22
<211> LENGTH: 1494
<212> TYPE: DNA
<213> ORGANISM: Artificial Sequence
<220> FEATURE:
<223> OTHER INFORMATION: Nucleotide sequence of the protein coding
      region of Bubulus bubulis (water buffalo) diacylglycerol
      O-acyltransferase 1 isoform X4 (BbDGAT1-X4) in pATO11, codon
      optimised for expression in yeast.

<400> SEQUENCE: 22

```
atgtgcccac aagaaggtaa aggttctcca ggtttgtctc catacaaaac tggtggtttg      60
gctcaatgtc caggttggcc accaggtggt agagttgttg gtggtagatg gggttgttgt     120
ttggaaccag cttctggtgc tggtccaggt ttatcttgtg ctccaccacc attgccacca     180
gctgaaggtt ggttgccatc tccaccagat ccagctttag gtgccggttt gtctgaagtt     240
ggttctgaag gtcctttgtt ggcttctgct gttgattcta gatgtcacag attgcaggat     300
tccttgttct cttctgattc tggtttctct aactacaggg gtattttgaa ctggtgcgtt     360
gttatgttga ttttgtctaa cgctaggctg ttcttggaga acttgattaa gtacggtatc     420
ttggttgatc caatccaggt tgtttctttg ttcttgaagg atccatattc ttggccagct     480
ttgtgtttgg ttatcgttgc taacattttt gctgttgctg ccttccaagt cgaaaaaaga     540
ttggctgttg gtgctttgac tgaacaagct ggtttgttgt tgcatggtgt taacttggct     600
accattttgt gttttccagc tgctgttgca tttctgttgg aatctattac tccagtcggt     660
tctgttttgg ctttgatggt ttacactatc ctgttcctaa agttgttctc ctacagagat     720
gttaatttgt ggtgcagaga aagacgtgct ggtgctaaag ctaaagctgc tttggctgac     780
ttgtactact ttttgtttgc tccaaccttg tgctacgaat tgaattttcc aagatctccc     840
aggatcagaa agaggttttt gttgagaaga ttgctggaaa tgctgttttt gacccaattg     900
caagtcggtt tgattcaaca atggatggtt ccagctatcc agaattctat gaagccattc     960
aaggatatgg actactccag aatcgtcgaa aggttgttga aattggcagt tccaaaccat   1020
```

-continued

```
ttgatctggc tgattttttt ctactggttg ttccactctt gcttgaatgc agttgctgaa      1080
ttgatgcaat ttggtgacag agaatttttac agagactggt ggaactctga atccattact     1140
tacttttggc agaactggaa catcccagtt cataagtggt gtatcagaca tttctacaag      1200
ccaatgctta gaaggggttc ttctaaatgg gctgctagaa cagcagtttt tttggcctct      1260
gcttttttcc acgaatactt ggtttctatc ccattgagaa tgttcagatt gtgggctttt      1320
actggtatga tggctcaaat tccattagct tggatcgttg gtagattctt cagaggtaat      1380
tatggtaatg ctgccgtttg gttgtccttg attattggtc aaccagttgc tgttttgatg      1440
tacgttcatg attactacgt cttgaacaga gaagctccag ctgcaggtac ttaa            1494
```

<210> SEQ ID NO 23
<211> LENGTH: 474
<212> TYPE: PRT
<213> ORGANISM: Bubalus bubalis

<400> SEQUENCE: 23

```
Met Cys Pro Gln Glu Gly Lys Gly Ser Pro Gly Leu Ser Pro Tyr Lys
1               5                   10                  15

Thr Gly Gly Leu Ala Gln Cys Pro Gly Trp Pro Pro Gly Gly Arg Val
            20                  25                  30

Val Gly Gly Arg Trp Gly Cys Cys Leu Glu Pro Ala Ser Gly Ala Gly
        35                  40                  45

Pro Gly Leu Ser Cys Ala Pro Pro Pro Leu Pro Pro Ala Glu Gly Trp
    50                  55                  60

Leu Pro Ser Pro Pro Asp Pro Ala Leu Gly Ala Gly Leu Ser Glu Val
65                  70                  75                  80

Gly Ser Glu Gly Pro Leu Leu Ala Ser Ala Val Asp Ser Arg Cys His
                85                  90                  95

Arg Leu Gln Asp Ser Leu Phe Ser Ser Asp Ser Gly Phe Ser Asn Tyr
            100                 105                 110

Arg Gly Ile Leu Asn Trp Cys Val Val Met Leu Ile Leu Ser Asn Ala
        115                 120                 125

Arg Leu Phe Leu Glu Asn Leu Ile Lys Tyr Gly Ile Leu Val Asp Pro
    130                 135                 140

Ile Gln Val Val Ser Leu Phe Leu Lys Asp Pro Tyr Ser Trp Pro Ala
145                 150                 155                 160

Leu Cys Leu Val Ile Val Ala Asn Ile Phe Ala Val Ala Ala Phe Gln
                165                 170                 175

Val Glu Lys Arg Leu Ala Val Gly Ala Leu Thr Glu Gln Ala Gly Leu
            180                 185                 190

Leu Leu His Gly Val Asn Leu Ala Thr Ile Leu Cys Phe Pro Ala Ala
        195                 200                 205

Val Ala Phe Leu Leu Glu Ser Ile Thr Pro Ala Val Leu Leu Pro Gly
    210                 215                 220

Arg Gln Pro Leu Val Pro Arg Ala Gln Gly Trp Gly Gln Gly Gln Gly
225                 230                 235                 240

Cys Phe Gly Arg Ser Leu Leu Leu Pro Leu Arg Pro Asp Pro Val Leu
                245                 250                 255

Arg Ala Gln Leu Pro Pro Leu Pro Pro His Pro Lys Ala Leu Pro Ala
            260                 265                 270

Ala Ala Thr Pro Gly Asp Ala Val Pro His Pro Ala Pro Gly Gly Ala
        275                 280                 285

Asp Pro Ala Val Asp Gly Pro Gly His Pro Glu Leu His Glu Ala Leu
```

-continued

```
            290                 295                 300

Gln Gly His Gly Leu Leu Pro His Arg Gly Ala Pro Pro Glu Ala Gly
305                 310                 315                 320

Gly Pro Gln Pro Pro His Leu Ala His Leu Leu Leu Ala Leu Pro
                325                 330                 335

Leu Leu Pro Glu Arg Arg Gly Arg Ala His Ala Val Trp Arg Pro Arg
                340                 345                 350

Val Leu Pro Gly Leu Val Glu Leu Arg Val Tyr His Leu Leu Leu Ala
            355                 360                 365

Glu Leu Glu His Pro Cys Ser Gln Val Val His Gln Thr Leu Leu Gln
            370                 375                 380

Ala His Ala Pro Ala Gly Gln Gln Gln Val Gly Ser Gln Asp Gly Ser
385                 390                 395                 400

Ile Ser Gly Leu Arg Leu Leu Pro Arg Val Pro Gly Glu His Pro Pro
                405                 410                 415

Ala His Val Pro Pro Leu Gly Leu His Gly His Asp Gly Ala Asp Pro
                420                 425                 430

Ala Gly Leu Asp Ser Gly Pro Leu Leu Pro Arg Gln Leu Arg Gln Arg
            435                 440                 445

Ser Arg Val Ala Val Thr His His Trp Ala Ala Gly Gly Arg Pro Asp
            450                 455                 460

Val Arg Pro Arg Leu Leu Arg Ala Gln Pro
465                 470
```

<210> SEQ ID NO 24
<211> LENGTH: 1425
<212> TYPE: DNA
<213> ORGANISM: Artificial Sequence
<220> FEATURE:
<223> OTHER INFORMATION: Nucleotide sequence of the protein coding
    region of Bubulus bubulis (water buffalo) diacylglycerol
    O-acyltransferase 1 isoform X5 (BbDGAT1-X5) in pAT012, codon
    optimised for expression in yeast.

<400> SEQUENCE: 24

```
atgtgcccac aagaaggtaa aggttctcca ggtttgtctc catacaaaac tggtggtttg      60
gctcaatgtc caggttggcc accaggtggt agagttgttg gtggtagatg gggttgttgt     120
ttggaaccag cttctggtgc tggtccaggt ttatcttgtg ctccaccacc attgccacca     180
gctgaaggtt ggttgccatc tccaccagat ccagctttag gtgccggttt gtctgaagtt     240
ggttctgaag gtcctttgtt ggcttctgct gttgattcta gatgtcacag attgcaggat     300
tccttgttct cttctgattc tggtttctct aactacaggg gtattttgaa ctggtgcgtt     360
gttatgttga tttttgtctaa cgctaggctg ttcttggaga acttgattaa gtacggtatc     420
ttggttgatc caatccaggt tgtttctttg ttcttgaagg atccatattc ttggccagct     480
ttgtgtttgg ttatcgttgc taacattttt gctgttgctg ccttccaagt cgaaaaaaga     540
ttggctgttg gtgctttgac tgaacaagct ggtttgttgt tgcatggtgt taacttggct     600
accattttgt gttttccagc tgctgttgca tttctgttgg aatctattac tccagctgtt     660
ttgttgccag gtagacaacc attggttcca agagcacaag gttggggtca aggtcaaggt     720
tgttttggta gatctttgtt gttaccattg aggccagatc tgtttttgag agcacaattg     780 ccactttac caccacatcc aaaggctttg cctgctgctg ctactccagg tgatgctgtt     840
ccacatccag ctccaggtgg tgcagatcct gcagttgatg tcctggtca tccagaattg     900 catgaagcct acaaggtca tggtttgtta ccacatagag gtgccccacc tgaagccggt     960
```

```
ggtccacaac cacctcattt ggctcatttg ttattattgg cattgcctct gttgccagag    1020
agaagaggta gagcacatgc tgtttggagg ccaagagttt tgccaggttt ggttgaattg    1080
agagtttacc acttgttgtt ggccgaattg gaacatccat gttctcaagt tgttcaccaa    1140
actttgttgc aagctcatgc tccagctggt caacaacagg ttggttctca agatggttct    1200
atttccggtt tgagattatt gcctagagtt ccaggtgaac atccaccagc tcatgttcca    1260
ccattgggtt tacatggtca tgatggtgct gacccagctg gtttagattc tggtccatta    1320
ttgccaagac aattgagaca gagatctaga gttgctgtta ctcatcattg ggctgccggt    1380
ggtagaccag atgttagacc aagattattg agagcccaac cataa                    1425
```

<210> SEQ ID NO 25
<211> LENGTH: 467
<212> TYPE: PRT
<213> ORGANISM: Bubalus bubalis

<400> SEQUENCE: 25

```
Met Gly Asp Arg Gly Gly Ala Gly Gly Ser Arg Arg Arg Arg Thr Gly
1               5                   10                  15

Ser Arg Pro Ser Ile Gln Gly Gly Ser Gly Pro Ala Ala Val Glu Glu
            20                  25                  30

Glu Val Arg Asp Ala Gly Ala Gly Gly Asp Ala Pro Val Arg Asp Thr
        35                  40                  45

Asp Lys Asp Gly Asp Val Asp Val Gly Ser Gly His Trp Asp Leu Arg
    50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Val Met Leu Ile Leu Ser
                85                  90                  95

Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
        115                 120                 125

Pro Ala Leu Cys Leu Val Ile Val Ala Asn Ile Phe Ala Val Ala Ala
        130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
            165                 170                 175

Ala Ala Val Ala Phe Leu Leu Glu Ser Ile Thr Pro Val Gly Ser Val
            180                 185                 190

Leu Ala Leu Met Val Tyr Thr Ile Leu Phe Leu Lys Leu Phe Ser Tyr
            195                 200                 205

Arg Asp Val Asn Leu Trp Cys Arg Glu Arg Arg Ala Gly Ala Lys Ala
        210                 215                 220

Lys Ala Ala Leu Ala Asp Leu Tyr Tyr Phe Leu Phe Ala Pro Thr Leu
225                 230                 235                 240

Cys Tyr Glu Leu Asn Phe Pro Arg Ser Pro Arg Ile Arg Lys Arg Phe
            245                 250                 255

Leu Leu Arg Arg Leu Leu Glu Met Leu Phe Leu Thr Gln Leu Gln Val
            260                 265                 270

Gly Leu Ile Gln Gln Trp Met Val Pro Ala Ile Gln Asn Ser Met Lys
            275                 280                 285
```

```
Pro Phe Lys Asp Met Asp Tyr Ser Arg Ile Val Glu Arg Leu Leu Lys
    290                 295                 300

Leu Ala Val Pro Asn His Leu Ile Trp Leu Ile Phe Phe Tyr Trp Leu
305                 310                 315                 320

Phe His Ser Cys Leu Asn Ala Val Ala Glu Leu Met Gln Phe Gly Asp
                325                 330                 335

Arg Glu Phe Tyr Arg Asp Trp Trp Asn Ser Glu Ser Ile Thr Tyr Phe
                340                 345                 350

Trp Gln Asn Trp Asn Ile Pro Val His Lys Trp Cys Ile Arg His Phe
        355                 360                 365

Tyr Lys Pro Met Leu Arg Arg Gly Ser Ser Lys Trp Ala Ala Arg Thr
    370                 375                 380

Ala Val Phe Leu Ala Ser Ala Phe Phe His Glu Tyr Leu Val Ser Ile
385                 390                 395                 400

Pro Leu Arg Met Phe Arg Leu Trp Ala Phe Thr Gly Met Met Ala Gln
                405                 410                 415

Ile Pro Leu Ala Trp Ile Val Gly Arg Phe Phe Arg Gly Asn Tyr Gly
            420                 425                 430

Asn Ala Ala Val Trp Leu Ser Leu Ile Ile Gly Gln Pro Val Ala Val
        435                 440                 445

Leu Met Tyr Val His Asp Tyr Tyr Val Leu Asn Arg Glu Ala Pro Ala
    450                 455                 460

Ala Gly Thr
465
```

<210> SEQ ID NO 26
<211> LENGTH: 1404
<212> TYPE: DNA
<213> ORGANISM: Artificial Sequence
<220> FEATURE:
<223> OTHER INFORMATION: Nucleotide sequence of the protein coding
      region of Bubulus bubulis (water buffalo) diacylglycerol
      O-acyltransferase 1 isoform X6 (BbDGAT1-X6) in pAT013, codon
      optimised for expression in yeast.

<400> SEQUENCE: 26

```
atgggtgata gaggtggtgc tggtggttct agaagaagaa ggacaggttc tagaccatct      60
attcaaggtg ttctggtcc agctgctgtt gaagaagagg ttagagatgc tggtgccggt     120
ggtgatgctc cagttagaga tactgataag gatggtgatg ttgatgttgg ttcaggtcat     180
tgggatttga tgtcatag attgcaggac agcttgttct cttctgattc tggttttct     240 aactacaggg gtattttgaa ctggtgcgtt gttatgttga ttttgtctaa cgctaggctg     300
ttcttggaga acttgattaa gtacggtatc ttggttgatc caatccaggt tgtttctttg     360
ttcttgaagg atccatattc ttggccagct ttgtgtttgg ttatcgttgc taacattttt     420
gctgttgctg ccttccaagt cgaaaaaaga ttggctgttg gtgctttgac tgaacaagca     480
ggtttgttgt tgcatggtgt taacttggct accattttgt gttttccagc agcagttgct     540
ttcttgttgg aatctattac tccagttggt tccgttttgg ctttgatggt ttacactatc     600
ctgttcctaa agctgttctc ctacagagat gttaatttgt ggtgtagaga aagacgtgct     660
ggtgctaaag ctaaagctgc tttggctgac ttgtactact ttttgtttgc tccaaccttg     720
tgctacgaat tgaattttcc aagatctccc aggatcagaa agaggttttt gttgagaaga     780
ttgctggaaa tgctgttttt gacccaattg caagtcggtt tgattcaaca atggatggtt     840
ccagctatcc agaattctat gaagccattc aaggatatgg actactccag aatcgtcgaa     900
```

-continued

```
aggttgttga aattggcagt tccaaaccat ttgatctggc tgattttttt ctactggttg      960
ttccactctt gcttgaatgc tgttgcagaa ttgatgcaat ttggtgacag agaatttttac    1020 agagactggt ggaactctga atccattact tacttttggc agaactggaa catcccagtt     1080
cataagtggt gtatcagaca tttctacaag ccaatgttgc gtagaggttc ttctaaatgg      1140
gctgctagaa cagcagtttt tttggcttct gctttcttcc acgaatactt ggtttctatc     1200
ccattgagaa tgttcagatt gtgggctttt actggtatga tggctcaaat tccattagct     1260
tggatcgttg gtagattctt cagaggtaat tatggtaatg ctgccgtttg gttgtccttg     1320
attattggtc aaccagttgc tgtttttgatg tacgttcatg attactacgt cttgaacaga    1380
gaagctccag ctgcaggtac ttaa                                           1404
```

```
<210> SEQ ID NO 27
<211> LENGTH: 459
<212> TYPE: PRT
<213> ORGANISM: Bubalus bubalis

<400> SEQUENCE: 27

Met Cys Pro Gln Glu Gly Lys Gly Ser Pro Gly Leu Ser Pro Tyr Lys
1               5                   10                  15

Thr Gly Gly Leu Ala Gln Cys Pro Gly Trp Pro Pro Gly Gly Arg Val
            20                  25                  30

Val Gly Gly Arg Trp Gly Cys Cys Leu Glu Pro Ala Ser Gly Ala Gly
        35                  40                  45

Pro Gly Leu Ser Cys Ala Pro Pro Leu Pro Pro Ala Glu Gly Trp
    50                  55                  60

Leu Pro Ser Pro Pro Asp Pro Ala Leu Gly Ala Gly Leu Ser Glu Val
65                  70                  75                  80

Gly Ser Glu Gly Pro Leu Leu Ala Ser Ala Val Asp Ser Arg Cys His
                85                  90                  95

Arg Leu Gln Asp Ser Leu Phe Ser Ser Asp Ser Gly Phe Ser Asn Tyr
            100                 105                 110

Arg Gly Ile Leu Asn Trp Cys Val Val Met Leu Ile Leu Ser Asn Ala
        115                 120                 125

Arg Leu Phe Leu Glu Asn Leu Ile Lys Tyr Gly Ile Leu Val Asp Pro
    130                 135                 140

Ile Gln Val Val Ser Leu Phe Leu Lys Asp Pro Tyr Ser Trp Pro Ala
145                 150                 155                 160

Leu Cys Leu Val Ile Val Ala Asn Ile Phe Ala Val Ala Ala Phe Gln
            165                 170                 175

Val Glu Lys Arg Leu Ala Val Gly Ala Leu Thr Glu Gln Ala Gly Leu
            180                 185                 190

Leu Leu His Gly Val Asn Leu Ala Thr Ile Leu Cys Phe Pro Ala Ala
            195                 200                 205

Val Ala Phe Leu Leu Glu Ser Ile Thr Pro Ala Val Leu Leu Pro Gly
    210                 215                 220

Arg Gln Pro Leu Val Pro Arg Ala Gln Gly Trp Gly Gln Gly Gln Gly
225                 230                 235                 240

Cys Phe Gly Arg Ser Leu Leu Leu Pro Leu Arg Pro Asp Pro Val Leu
            245                 250                 255

Arg Ala Gln Leu Pro Pro Leu Pro Pro His Pro Lys Ala Leu Pro Ala
            260                 265                 270

Ala Ala Thr Pro Gly Asp Ala Val Pro His Pro Ala Pro Gly Gly Ala
            275                 280                 285
```

-continued

```
Asp Pro Ala Val Asp Gly Pro Gly His Pro Glu Leu His Glu Ala Leu
    290                 295                 300

Gln Gly Pro Gln Pro Pro His Leu Ala His Leu Leu Leu Leu Ala Leu
305                 310                 315                 320

Pro Leu Leu Pro Glu Arg Arg Gly Arg Ala His Ala Val Trp Arg Pro
                325                 330                 335

Arg Val Leu Pro Gly Leu Val Glu Leu Arg Val Tyr His Leu Leu Leu
                340                 345                 350

Ala Glu Leu Glu His Pro Cys Ser Gln Val Val His Gln Thr Leu Leu
            355                 360                 365

Gln Ala His Ala Pro Ala Gly Gln Gln Gln Val Gly Ser Gln Asp Gly
    370                 375                 380

Ser Ile Ser Gly Leu Arg Leu Leu Pro Arg Val Pro Gly Glu His Pro
385                 390                 395                 400

Pro Ala His Val Pro Pro Leu Gly Leu His Gly His Asp Gly Ala Asp
                405                 410                 415

Pro Ala Gly Leu Asp Ser Gly Pro Leu Leu Pro Arg Gln Leu Arg Gln
                420                 425                 430

Arg Ser Arg Val Ala Val Thr His His Trp Ala Ala Gly Gly Arg Pro
            435                 440                 445

Asp Val Arg Pro Arg Leu Leu Arg Ala Gln Pro
    450                 455
```

```
<210> SEQ ID NO 28
<211> LENGTH: 1380
<212> TYPE: DNA
<213> ORGANISM: Artificial Sequence
<220> FEATURE:
<223> OTHER INFORMATION: Nucleotide sequence of the protein coding
      region of Bubulus bubulis (water buffalo) diacylglycerol
      O-acyltransferase 1 isoform X7 (BbDGAT1-X7) in pAT014, codon
      optimised for expression in yeast.

<400> SEQUENCE: 28
atgtgcccac aagaaggtaa aggttctcca ggtttgtctc catacaaaac tggtggtttg     60
gctcaatgtc caggttggcc accaggtggt agagttgttg gtggtagatg gggttgttgt    120
ttggaaccag cttctggtgc tggtccaggt ttatcttgtg ctccaccacc attgccacca    180
gctgaaggtt ggttgccatc tccaccagat ccagctttag gtgccggttt gtctgaagtt    240
ggttctgaag gtcctttgtt ggcttctgct gttgattcta gatgtcacag attgcaggat    300
tccttgttct cttctgattc tggtttctct aactacaggg gtattttgaa ctggtgcgtt    360
gttatgttga ttttgtctaa cgctaggctg ttcttggaga acttgattaa gtacggtatc    420
ttggttgatc aatccaggt tgtttctttg ttcttgaagg atccatattc ttggccagct    480
ttgtgtttgg ttatcgttgc taacattttt gctgttgctg ccttccaagt cgaaaaaaga    540
ttggctgttg gtgctttgac tgaacaagct ggttgttgt tgcatggtgt taacttggct    600
accattttgt gttttccagc tgctgttgca tttctgttgg aatctattac tccagctgtt    660
ttgttgccag gtagacaacc attggttcca agagcacaag gttggggtca aggtcaaggt    720
tgttttggta gatctttgtt gttaccattg aggccagatc ctgttttgag agcacaattg    780
ccacctttac caccacatcc aaaggctttg cctgctgctg ctactccagg tgatgctgtt    840
ccacatccag ctccaggtgg tgcagatcct gcagttgatg tcctggtca tccagaattg    900 catgaagcct acaaggtcc acaaccacct catttggctc acttgttgtt gttagctttg    960
```

-continued

```
ccattattgc cagagagaag aggtagagca catgctgttt ggaggccaag agttttgcca      1020
ggtttggttg aattgagagt ttaccatttg ttgctggccg aattggaaca tccatgttct      1080
caagttgttc accaaacttt gttgcaagct catgctccag ctggtcaaca acaggttggt      1140
tctcaagatg gttctatttc cggtttgaga ttgctaccaa gagttccagg tgaacatcca      1200
ccagctcatg ttccaccatt gggtttacat ggtcatgatg gtgctgaccc agctggttta      1260
gattctggtc cattattacc aagacagttg agacagagat ctagagttgc tgttactcat      1320
cattgggctg ccggtggtag accagatgtt agaccaagat tattgagagc ccaaccataa      1380
```

```
<210> SEQ ID NO 29
<211> LENGTH: 489
<212> TYPE: PRT
<213> ORGANISM: Bos taurus

<400> SEQUENCE: 29

Met Gly Asp Arg Gly Gly Ala Gly Gly Ser Arg Arg Arg Arg Thr Gly
1               5                   10                  15

Ser Arg Pro Ser Ile Gln Gly Gly Ser Gly Pro Ala Ala Ala Glu Glu
            20                  25                  30

Glu Val Arg Asp Val Gly Ala Gly Gly Asp Ala Pro Val Arg Asp Thr
        35                  40                  45

Asp Lys Asp Gly Asp Val Asp Val Gly Ser Gly His Trp Asp Leu Arg
    50                  55                  60

Cys His Arg Leu Gln Asp Ser Leu Phe Ser Ser Asp Ser Gly Phe Ser
65                  70                  75                  80

Asn Tyr Arg Gly Ile Leu Asn Trp Cys Val Val Met Leu Ile Leu Ser
                85                  90                  95

Asn Ala Arg Leu Phe Leu Glu Asn Leu Ile Lys Tyr Gly Ile Leu Val
            100                 105                 110

Asp Pro Ile Gln Val Val Ser Leu Phe Leu Lys Asp Pro Tyr Ser Trp
        115                 120                 125

Pro Ala Leu Cys Leu Val Ile Val Ala Asn Ile Phe Ala Val Ala Ala
    130                 135                 140

Phe Gln Val Glu Lys Arg Leu Ala Val Gly Ala Leu Thr Glu Gln Ala
145                 150                 155                 160

Gly Leu Leu Leu His Gly Val Asn Leu Ala Thr Ile Leu Cys Phe Pro
                165                 170                 175

Ala Ala Val Ala Phe Leu Leu Glu Ser Ile Thr Pro Val Gly Ser Val
            180                 185                 190

Leu Ala Leu Met Val Tyr Thr Ile Leu Phe Leu Lys Leu Phe Ser Tyr
        195                 200                 205

Arg Asp Val Asn Leu Trp Cys Arg Glu Arg Arg Ala Gly Ala Lys Ala
    210                 215                 220

Lys Ala Ala Leu Ala Gly Lys Ala Ala Asn Gly Gly Ala Ala Gln Arg
225                 230                 235                 240

Thr Val Ser Tyr Pro Asp Asn Leu Thr Tyr Arg Asp Leu Tyr Tyr Phe
                245                 250                 255

Leu Phe Ala Pro Thr Leu Cys Tyr Glu Leu Asn Phe Pro Arg Ser Pro
            260                 265                 270

Arg Ile Arg Lys Arg Phe Leu Leu Arg Arg Leu Leu Glu Met Leu Phe
        275                 280                 285

Leu Thr Gln Leu Gln Val Gly Leu Ile Gln Gln Trp Met Val Pro Ala
    290                 295                 300
```

-continued

```
Ile Gln Asn Ser Met Lys Pro Phe Lys Asp Met Asp Tyr Ser Arg Ile
305             310             315             320

Val Glu Arg Leu Leu Lys Leu Ala Val Pro Asn His Leu Ile Trp Leu
            325             330             335

Ile Phe Phe Tyr Trp Leu Phe His Ser Cys Leu Asn Ala Val Ala Glu
            340             345             350

Leu Met Gln Phe Gly Asp Arg Glu Phe Tyr Arg Asp Trp Trp Asn Ser
        355             360             365

Glu Ser Ile Thr Tyr Phe Trp Gln Asn Trp Asn Ile Pro Val His Lys
    370             375             380

Trp Cys Ile Arg His Phe Tyr Lys Pro Met Leu Arg Arg Gly Ser Ser
385             390             395             400

Lys Trp Ala Ala Arg Thr Ala Val Phe Leu Ala Ser Ala Phe Phe His
            405             410             415

Glu Tyr Leu Val Ser Ile Pro Leu Arg Met Phe Arg Leu Trp Ala Phe
            420             425             430

Thr Gly Met Met Ala Gln Ile Pro Leu Ala Trp Ile Val Gly Arg Phe
        435             440             445

Phe Arg Gly Asn Tyr Gly Asn Ala Ala Val Trp Leu Ser Leu Ile Ile
    450             455             460

Gly Gln Pro Val Ala Val Leu Met Tyr Val His Asp Tyr Tyr Val Leu
465             470             475             480

Asn Arg Glu Ala Pro Ala Ala Gly Thr
            485
```

<210> SEQ ID NO 30
<211> LENGTH: 1470
<212> TYPE: DNA
<213> ORGANISM: Artificial Sequence
<220> FEATURE:
<223> OTHER INFORMATION: Nucleotide sequence of the protein coding
      region of Bos taurus (cattle) diacylglycerol O-acyltransferase 1
      lactation isoform X1 (BtDGAT1lac) in pAT019, codon optimised for
      expression in yeast.

<400> SEQUENCE: 30

```
atgggtgata gaggtggtgc tggtggttct agaagaagaa ggacaggttc tagaccatct      60
attcaaggtg ttctggtcc agctgctgct gaagaagagg ttagagatgt tggtgccggt     120
ggtgatgctc cagttagaga tactgataag gatggtgatg ttgatgttgg ttcaggtcat     180
tgggatttga gatgtcatag attgcaggac agcttgttct cttctgattc tggttttct      240 aactacaggg gtattttgaa ctggtgcgtt gttatgttga ttttgtctaa cgctaggctg     300
ttcttggaga acttgattaa gtacggtatc ttggttgatc caatccaggt gtttctttg      360 ttcttgaagg atccatattc ttggccagct ttgtgtttgg ttatcgttgc taacattttt     420
gctgttgctg ccttccaagt cgaaaaaaga ttggctgttg gtgctttgac tgaacaagca     480
ggtttgttgt tgcatggtgt taacttggct accattttgt gttttccagc tgcagttgct     540
ttcttgttgg aatctattac tccagttggt tccgttttgg ctttgatggt ttacactatc     600
ctgttcctaa agctgttctc ctacagagat gttaatttgt ggtgtagaga aagacgtgct     660
ggtgctaaag ctaaagctgc tttggctggt aaagctgcaa atggtggtgc agctcaaaga     720
actgtttctt acccagataa cttgacttac agggacttgt actacttttt gttcgctcca     780
actttgtgct acgaattgaa ttttccaaga agcccaagga tcagaaagag gttttttgttg     840 agaaggttgt tggagatgtt gtttttgacc caattgcaag tcggtttgat ccaacaatgg     900
```

-continued

```
atggttccag ctattcagaa ttctatgaag ccattcaagg acatggacta ctctagaatc      960
gtcgaaagat tattgaagtt ggccgttcca aaccatttga tctggttgat tttttttctac    1020 tggctgttcc actcttgctt gaatgctgtt gcagaattga tgcaatttgg tgacagagaa     1080
ttttacagag actggtggaa ctctgaatcc attacttact tttggcagaa ctggaacatc     1140
ccagttcata agtggtgtat cagacatttc tacaagccaa tgttgcgtag aggttcttct     1200
aaatgggctg ctagaactgc tgtttttttg gcttctgctt tcttccacga atacttggtt     1260
tctatcccat tgagaatgtt cagattgtgg gcttttactg gtatgatggc tcaaattcca     1320
ttagcttgga tcgttggtag attcttcaga ggtaattatg gtaatgctgc cgtttggttg     1380
tccttgatta ttggtcaacc agttgctgtt ttgatgtacg ttcatgatta ctacgtcttg     1440
aacagagaag ctcctgctgc tggtacttaa                                      1470
```